(12) United States Patent
Vuyisich et al.

(10) Patent No.: US 12,040,053 B2
(45) Date of Patent: Jul. 16, 2024

(54) METHODS FOR GENERATING SEQUENCER-SPECIFIC NUCLEIC ACID BARCODES THAT REDUCE DEMULTIPLEXING ERRORS

(71) Applicants: BlueDot LLC, Bellevue, WA (US); TRIAD NATIONAL SECURITY, LLC, Los Alamos, NM (US)

(72) Inventors: Momchilo Vuyisich, Los Alamos, NM (US); Jason Gans, Los Alamos, NM (US); Patrick Chain, Los Alamos, NM (US); Andrew Hatch, Los Alamos, NM (US)

(73) Assignees: BLUEDOT, LLC, Bellevue, WA (US); TRIAD NATIONAL SECURITY, LLC, Los Alamos, NM (US)

( * ) Notice: Subject to any disclaimer, the term of this patent is extended or adjusted under 35 U.S.C. 154(b) by 287 days.

(21) Appl. No.: 16/621,998

(22) PCT Filed: Jun. 21, 2018

(86) PCT No.: PCT/US2018/038855
§ 371 (c)(1),
(2) Date: Dec. 12, 2019

(87) PCT Pub. No.: WO2018/237209
PCT Pub. Date: Dec. 27, 2018

(65) Prior Publication Data
US 2020/0131506 A1    Apr. 30, 2020

Related U.S. Application Data
(60) Provisional application No. 62/523,208, filed on Jun. 21, 2017.

(51) Int. Cl.
G16B 35/10    (2019.01)
C12Q 1/6811   (2018.01)
(Continued)

(52) U.S. Cl.
CPC ............ *G16B 35/10* (2019.02); *C12Q 1/6811* (2013.01); *G16B 20/00* (2019.02); *G16B 25/20* (2019.02);
(Continued)

(58) Field of Classification Search
None
See application file for complete search history.

(56) References Cited

U.S. PATENT DOCUMENTS

| | | | |
|---|---|---|---|
| 2002/0015955 A1 | 2/2002 | Meyerson | |
| 2015/0080266 A1* | 3/2015 | Volkmuth | ............ C12Q 1/6869 702/19 |

(Continued)

FOREIGN PATENT DOCUMENTS

| | | |
|---|---|---|
| WO | 2016176091 A1 | 11/2016 |

OTHER PUBLICATIONS

Galanti, L.; Shasha, D.; Gunsalus, K. C. Pheniqs: Fast and Flexible Quality-Aware Sequence Demultiplexing. bioRxiv Apr. 19, 2017. https://doi.org/10.1101/128512.*

(Continued)

*Primary Examiner* — Soren Harward
(74) *Attorney, Agent, or Firm* — Morgan, Lewis & Bockius LLP

(57) ABSTRACT

Provided herein are compositions and methods for analyzing nucleic acids in a sample. Compositions include simple barcode sets having reduced DNA sequencing instrument-specific error rates. Methods include methods to deconvolute sequence reads from different samples.

30 Claims, 21 Drawing Sheets
Specification includes a Sequence Listing.

(51) Int. Cl.
  *G16B 20/00* (2019.01)
  *G16B 25/20* (2019.01)
(52) U.S. Cl.
  CPC ............. *C12Q 2537/165* (2013.01); *C12Q 2563/179* (2013.01)

(56) References Cited

U.S. PATENT DOCUMENTS

2015/0087537 A1* 3/2015 Hubbell ............. C40B 70/00
  506/4
2016/0314242 A1 10/2016 Schnall-Levin et al.

OTHER PUBLICATIONS

Schober, S.; Mir, K.; Neuhaus, K.; Bossert, M. Design of Short Barcodes for next Generation Sequencing of DNA and RNA. In Proceedings 2012 IEEE International Workshop on Genomic Signal Processing and Statistics (GENSIPS); IEEE: Washington, DC, USA, 2012; pp. 31-34.*

Huang, W.; Li, L.; Myers, J. R.; Marth, G. T. ART: A next-Generation Sequencing Read Simulator. Bioinformatics 2012, 28 (4), 593-594.*

McElroy, K. E.; Luciani, F.; Thomas, T. GemSIM: General, Error-Model Based Simulator of next-Generation Sequencing Data. BMC Genomics 2012, 13 (1), 74:1-9.*

Charul Gijavanekar et al: "Rare target enrichment for ultrasensitive PCR detection using co-rehybridization and duplex-specific nuclease", Analytical Biochemistry, vol. 421, No. 1, Feb. 1, 2012 (Feb. 1, 2012, pp. 81-85.

European Patent Office, "International Search Report and Written Opinion" for PCT/US18/38855, dated Nov. 20, 2018, 21 pages.

Tilo Buschmann et al., "Levenshtein error-correcting barcodes for multiplexed DNA sequencing", BMC Bioinformatics, vol. 14, No. 1, Jan. 1, 2013, 11 pages.

D'Amore, Rosalinda, et al. A comprehensive benchmarking study of protocols and sequencing platforms for 16S rRNA community profiling, BMC Genomics (2016) 17:55.

Illumina, "Effects of index misassignment on multiplexing and downstream analysis," 2017.

Hatch, Andrew, et al. A Robust Metatranscriptomic Technology for Population-Scale Studies of Diet, Gut Microbiome, and Human Health, Hindawi International Journal of Genomics vol. 2019, Article ID 1718741, 9 pages.

Huang, Weichen et al. ART: a next-generation sequencing read simulator, Bioinformatics, vol. 28 No. 4 2012, pp. 593-594 (Supplementary Material).

Mcelroy, Kerensa E. et al. GEMSIM: General, Error-Model based simulator of next generation sequencing data. BMC Genomics 2012, 13(1), 74:1-9.

Sinha, Rahul et al. Index switching causes "spreading-of-signal" among multiplexed samples in illumina HiSeq 4000 DNA sequencing, 2017.

* cited by examiner

RNR process applied to human blood: Sequencing reads mapping to the human 45S transcripts with (red) and without (black) RNR applied.

Empowering the Development of Genomics Expertise (EDGE) platform:
- Genomic Origins Through Taxonomic Challenge (GOTTCHA)
- Burrows-Wheeler Aligner (BWA)

Analyses:
- Read trimming
- Data QC before and after trimming
- De-hosting
- Multiple metagenomic analyses
- Multiple data outputs Species level classification of sequencing reads from a human blood sample spiked with *Salmonella enterica*

Species level classification of sequencing reads from a respiratory sample (the person had upper respiratory tract infection).

Strain level classification of sequencing reads from a human stool sample (Norovirus suspected but tested negative by PCR). Symptoms consistent with *C. difficile*.

SRS analysis of a human sputum sample

Species level classification of sequencing reads from a human sputum sample (sample validated and provided by New Mexico Department of Health).

Species and strain level classification of sequencing reads from a human urine sample provided via LANL OccMed.

- Universal process for all clinical samples
- Inexpensive (custom reagents, declutter)
- Efficient (throughput, data storage)
- Rapid
- Automatable
- Multiplexible
- Easy data analysis that is accurate *or* sensitive (or both)
- Fully customizable

|⎯⎯⎯⎯⎯⎯⎯⎯⎯ 24-36 hours from samples to result ⎯⎯⎯⎯⎯⎯⎯⎯⎯|

METHODS FOR GENERATING SEQUENCER-SPECIFIC NUCLEIC ACID BARCODES THAT REDUCE DEMULTIPLEXING ERRORS

REFERENCE TO RELATED APPLICATIONS

This application claims the benefit of U.S. Provisional Application No. 62/523,208, filed Jun. 21, 2017, which application is incorporated herein by reference.

STATEMENT REGARDING FEDERALLY SPONSORED RESEARCH OR DEVELOPMENT

The United States government has certain rights in this invention pursuant to Contract No. DE-AC52-06NA25396 between the United States Department of Energy and Los Alamos National Security, LLC for the operation of Los Alamos National Laboratory.

THE NAMES OF PARTIES TO A JOINT RESEARCH AGREEMENT

Certain inventions disclosed herein were made by one or more parties to a joint research agreement. The parties to the joint research agreement are Los Alamos National Security, LLC and BlueDot, LLC.

SEQUENCE LISTING

The instant application contains a Sequence Listing which has been submitted electronically in ASCII format and is hereby incorporated by reference in its entirety. Said ASCII copy, created on Nov. 23, 2020, is named VIOM-001_NTL-US.txt and is 1,553 bytes in size.

BACKGROUND

Next generation sequencing (NGS) has become a powerful tool for detection, quantification and characterization of microorganisms in complex communities. The main advantage of NGS is its non-biased approach that identifies all organisms in a sample. This is in contrast to traditional molecular assays that limit the analysis of a sample to a set of specific microorganisms. In clinical samples, the relative abundance of nucleic acids from particular microbes, such as pathogen or gut microbiome nucleic acids (DNA or RNA), is vanishingly small relative to the native nucleic acids in a sample, and accurate selection and identification of true microbial (including pathogenic) nucleic acids amidst sample and sequencing errors is challenging, if at all possible. Therefore, it is currently necessary to generate and analyze vast amounts of sequence data in order to identify rare or previously unidentified microbial (including pathogen and gut microbiome) sequences.

Emerging research is showing that the gut microbiome can be particularly important when managing a host of factors that impact health and wellbeing. For example, the gut microbiome may impact nutrition, weight loss, diabetes, mental health, autoimmune disorders and more. Such information about the nucleic acids present in a sample can be useful in identifying the bacteria present in the samples. In addition, when looking at RNA, the information can also be useful in determining what those bacteria are doing by analyzing their gene expression.

It is often cost effective to run multiple samples at the same time. It can be difficult, however, to distinguish between samples being analyzed using modern sequencing techniques, often called "next-generation" sequencing. Nucleic acids from a sample can be barcoded, but such barcodes are prone to sequencing errors that lead to mistakes when demultiplexing samples sequenced at the same time. Therefore, it is necessary to generate barcode sequences and molecules that reduce demultiplexing errors.

SUMMARY

In one aspect provided herein is a method of analyzing nucleic acids in one or more samples from one or more subjects, the method comprising: purifying nucleic acids from the sample; removing non-informative RNA (RNR) from the purified nucleic acids using a sample-specific set of oligonucleotides to form RNR-processed nucleic acids; preparing a library of nucleic acid fragments from the RNR-processed nucleic acids; attaching sequence instrument-specific barcode oligonucleotides to the nucleic acid fragments in the library to form a barcoded library of nucleic acid fragments; sequencing the barcoded library of nucleic acid fragments to obtain sequence data; and analyzing the sequence data using at least one algorithm or database for genomic classification to identify and/or quantify and/or functionally characterize microbes in the sample. In one embodiment the sample from a subject is selected from stool, blood, throat swab, nasopharyngeal swab, sputum, cerebrospinal fluid, serum, plasma, and/or urine. In another embodiment preparing the library of nucleic acid fragments and attaching barcode oligonucleotides to the nucleic acid fragments comprises one amplification reaction. Methods of attaching barcode oligonucleotides to the nucleic acids fragments include ligating the barcode oligonucleotides to the nucleic acid fragments. Alternatively or in addition, methods of attaching barcode oligonucleotides to the nucleic acid fragments include amplifying the nucleic acid fragments using primers comprising the barcode oligonucleotides.

In another embodiment the subject is a human. In another embodiment non-informative RNA includes ribosomal RNA and/or transfer RNA. In another embodiment removing the non-informative RNA comprises removing mRNA species that account for at least 50%, at least 75%, at least 90%, at least 95%, or at least 99% of the mRNA species in the sample. Removing the non-informative RNA can comprise removing mRNA species that account for at least 50%, at least 75%, at least 90%, at least 95%, or at least 99% of the total mRNA in the sample. In another embodiment the method comprises analyzing a plurality of samples, wherein each different sample is provided with a different sequence instrument-specific nucleotide barcode sequence. In another embodiment the method further comprises quantifying sample-to-sample contamination. In another embodiment quantifying sample to sample contamination comprises using synthetic DNA or RNA oligonucleotides (SDROs).

In another aspect provided herein is a method for generating a plurality of barcode sequences of length N, comprising: generating, by a processor, a set of some or all possible sequences of length N; for each starting barcode sequence in the set of some or all possible sequences: add a starting barcode to a candidate pool of barcode sequences; identify a candidate sequence in the set of some or all possible sequences that minimizes an objective function $\Theta$ representing a probability of observing any sequence in the candidate pool when an actual sequence is the candidate sequence; add the candidate sequence to the candidate pool; compare the best computed $\Theta$ to the $\Theta$ computed for the candidate pool; and output the candidate pool having the best computed Θ. The actual sequence can include detected, sequenced, or observed sequences.

In another aspect provided herein is a method for generating a plurality of barcode sequences of length N, comprising: generating, by a processor, a set of sequences of length N; identifying in the set of sequences a candidate sequence that reduces an objective function Θ representing the probability of observing the candidate sequence in a candidate pool; comparing the computed Θ to the Θ computed for the candidate pool; and outputting a candidate pool comprising a plurality of barcode sequences of length N having reduced computed Θ.

A variety of next-generation methods and devices exist for sequencing large nucleic acid samples. Each type of next-generation sequencer or method varies in the amount and types of sequencing errors it makes. In one embodiment the barcode sequences are customized to a sequencer, and wherein the objective function is computed in accordance with an error model associated with the sequencer. Minimizing the objective function can comprise reducing or minimizing errors associated with demultiplexing sequences. This can include minimizing the likelihood that errors will cause one of the barcode sequences to appear to be more similar to a different barcode sequence in the same set. Thus, in some instances, minimizing the objective function includes minimizing or reducing the probability that members of a set of barcodes are mistaken for one another. Alternatively or in addition, minimizing the objective function includes increasing or maximizing the probability that the barcodes within a candidate pool will be identified with confidence. Minimizing the objective function can comprise generating a plurality of sequences wherein a first barcode of the barcode candidate pool will not be incorrectly identified as a different barcode in the barcode candidate pool when a sequence read of the first barcode differs from a corresponding barcode sequence from the candidate pool by one nucleotide, two nucleotides, three nucleotides, or four nucleotides.

In another embodiment the error model is computed by: sequencing a plurality of training barcode sequences of length N using the sequencer to generate a plurality of sequenced reads; and for each position in the training barcode sequences of length N and for each actual nucleotide in the training barcode sequences, counting the number of occurrences of each nucleotide in the sequenced reads.

In another embodiment the error model is computed by: sequencing a plurality of training barcode sequences of length N using the sequencer to generate a plurality of sequenced reads, wherein the sequences of the training barcode sequences are known; and counting the number of occurrences of each nucleotide in each position of each sequence read corresponding to a training barcode sequence. In some embodiments, the method further comprises determining the probability that a nucleotide at a position in a barcode sequence will be detected accurately. In some embodiments, the determining is computed according to an objective function. In another embodiment the objective function is:

$$\Theta = \sum_{i=0}^{M-1} \sum_{j=i+1}^{M-1} \rho(\sigma_i | \sigma_j),$$

wherein $$\rho(\sigma_i | \sigma_j) = \sum_{k=0}^{N-1} \ln[P(\sigma_{ik} | \sigma_{jk}, k)],$$

and
wherein $\rho(\sigma_i|\sigma_j)$ is the natural log of the probability of observing sequence $\sigma_i$ when the actual barcode sequence supplied to the sequencer is $\sigma_j$, M is the number of barcodes, $\sigma_{ik}$ refers to the nucleotide at the kth position in the ith barcode sequence, and $P(\sigma_{ik}|\sigma_{jk}, k)$ is the error model associated with the sequencer.

In one embodiment, reads from a collection of barcodes are sorted based on barcode sequences in the collection. This process can be performed tolerating an error of one edit distance, that is, a read differs from a barcode sequence in the set by one base. For reads assigned to any particular barcode, at any position in the barcode, the number of errors is calculated, either as total incorrect reads at a position, or errors on a per-base basis (e.g., reading "A" instead of "G"). The error rate at any position for the entire collection of barcodes can be calculated. This calculation also can be for total errors or particular errors. For example, one may calculate the probability of any error at all, or the probability that a particular nucleotide will be misread (e.g., the chance that a read of "A" is actually a "G" in the actual barcode).

In another aspect provided herein is a method of generating an instrument specific DNA sequencing error model comprising: providing a training set of barcode oligonucleotides, each member of the training set comprising a barcode N nucleotides in length, wherein N is or comprises at least 5, is or comprises at least 6, is or comprises at least 7, is or comprises at least 8, is or comprises at least 9, is or comprises at least 10, is or comprises at least 11, is or comprises at least 12, is or comprises at least 13, is or comprises at least 14, or is or comprises or at least 15; sequencing, together or separately, members of the training set on a DNA sequencing instrument to generate an output comprising sequence reads; and generating an instrument or method specific sequencing error model from the sequencing instrument output, wherein the model comprises, for each position in the barcode, a number of observed nucleotides for each actual nucleotide at position. In one embodiment sequencing comprises generating a plurality of sequence reads for each member of the training set. In some embodiments, throughout the training set, each nucleotide (A, T, G, or C) appears at least once in each position of the barcode. In another embodiment throughout the training set, each nucleotide pair (AA, AT, AG, AC, TA, TT, TG, TC, GA, GT, GG, GC, CA, CT, CG, CC,) appears at least once in each position of the barcode. In another embodiment the training set comprises no more than 4, 8, 16, 32, 64 or 128 different members. In another embodiment the training barcode sequences are sequenced together and sequence reads are sorted into groups by identifying the closest matching training barcode sequence in the training set. In another embodiment the sequencing instrument uses massively parallel signature sequencing (MPSS), DNA cluster sequencing (e.g., Illumina), polony sequencing (e.g., Church), pyrosequencing (e.g., Roche), sequencing by ligation (e.g., SOLiD sequencing, Thermo) semiconductor sequencing (e.g., DNA nanoball sequencing (e.g., Complete Genomics), single molecule sequencing (e.g., Helicos), single molecule real time (SMRT) sequencing, or nanopore DNA sequencing (e.g., PacBio).

In another aspect provided herein is a method of preparing oligonucleotides for use with a DNA sequencing instrument, wherein the oligonucleotides comprise M different nucleotide barcode sequences of at least N nucleotides in length, wherein M is at least five, at least 10, at least 20, at least 40, at least 50, at least 75, or at least 100. M can also be less than 5, less than 10, less than 20, less than 40, less than 50, less than 75, or less than 100. In some embodiments, the method comprises generating a set of some or all possible nucleotide sequences of length N, wherein N is or comprises at least 5, is or comprises at least 6, is or comprises at least 7, is or comprises at least 8, is or comprises at least 9, is or comprises at least 10, is or comprises at least 11, is or comprises at least 12, is or comprises at least 13, is or comprises at least 14, or is or comprises at least 15; generating a plurality of groups of M nucleotide barcode sequences selected from the set; determining for each group, by using a sequencing error model for the DNA sequencing instrument, a probability of sequencing error for the nucleotide barcode sequences; selecting a group from the plurality of groups having a probability of sequencing error in the lowest 50%, lowest 25%, lowest 10%, lowest 5%, lowest 1%, or absolute lowest of the groups; and synthesizing oligonucleotides comprising the nucleotide barcode sequences of the selected group. N can also be or be less than 15, be or be less than 14, be or be less than 13, be or be less than 12, be or be less than 11, be or be less than 10, be or be less than 9, be or be less than 8, be or be less than 7, be or be less than 6, or be or be less than 5.

In one embodiment the oligonucleotides further comprise an amplification primer sequence. In another embodiment the method further comprises attaching the synthesized oligonucleotides to polynucleotide molecules in a plurality of different samples, wherein polynucleotides in each of the samples comprise the same oligonucleotide barcode and different samples comprise different oligonucleotide barcode. In another embodiment the method further comprises attaching the synthesized oligonucleotides to polynucleotide molecules in a plurality of different samples, wherein polynucleotides in the same sample comprise the same oligonucleotide barcode and polynucleotides in different samples comprise different oligonucleotide barcodes.

In another aspect provided herein is a method comprising: a) generating an initial set of some or all possible nucleotide sequences of length N (4N sequences); b) in a first iteration, performing a selection process comprising: i) partitioning the initial set into a first subset of one or more sequences selected from the initial set and a second subset of remainder sequences of the initial set; ii) generating pairs of candidate pools and remainder pools, wherein: 1) a candidate pool comprises polynucleotide(s) having the sequence(s) in the first subset and a polynucleotide having the sequence of a different member of the second subset, 2) a remainder pool comprises polynucleotides having sequences of the second subset less the different member added to the candidate pool; iii) sequencing the candidate pools; iv) determining, for each sequenced candidate pool, a sequencing error rate; and v) selecting a sequenced candidate pool having an acceptably low error rate or the lowest error rate; c) in X subsequent iterations, performing a selection process comprising: i) providing the selected sequenced candidate pool and its paired remainder pool from the previous iteration as a first subset and a second subset, respectively; ii) generating pairs of candidate pools and remainder pools, wherein: 1) each candidate pool comprises the sequences in the first subset and a different member of the second subset, 2) each remainder pool comprises sequences of the second subset less the different member added to the candidate pool; iii) sequencing the candidate pools; iv) determining, for each sequenced candidate pool, a sequencing error rate; and v) selecting a sequenced candidate pool having an acceptably low error rate or the lowest error rate. In another aspect provided herein is a kit comprising a plurality of M containers, each container comprising an ensemble of oligonucleotide molecules comprising nucleotide barcode sequences of length N, wherein: the predominant nucleotide barcode sequences in each ensemble is different from the other ensembles; and the nucleotide barcode sequences in the kit have a probability of sequencing error, when sequenced by a selected DNA sequencing instrument, that is below a designated error threshold. In another embodiment the probability of sequencing error is determined by a probability model as described herein. In another embodiment the designated threshold is less than a probability sequencing error for the selected DNA sequencing instrument of a set of M control nucleotide sequences of length N having collective edit distance of at least one, at least two, at least three, at least four or at least five. The threshold value can be an error tolerance rate, wherein sequence reads of the barcode candidate pool comprising a single error are still correctly identified as a corresponding barcode in the barcode candidate pool. The threshold value can be an error tolerance rate, wherein sequence reads of the barcode candidate pool comprising two, three, four, five, or six errors are still correctly identified as a corresponding barcode in the barcode candidate pool. Types of errors include amplification errors, oligonucleotide synthesis errors, mutations, or read errors caused by the sequencer.

In another aspect provided herein is a method for determining sample-to-sample cross-contamination comprising: originally introducing into each of a plurality of containers, a different sample comprising polynucleotides, wherein at least one sample comprises a polynucleotide having a nucleotide sequence unique to that sample; sequencing the polynucleotides in each of the containers to produce sequence reads; determining from the sequence reads, the presence and/or amount of the unique nucleotide in containers into which the unique nucleotide sequence was not originally introduced.

In one embodiment the containers are comprised as individual tubes, tubes in a strip, or wells in a multi-well plate. In another embodiment the method further comprises, before sequencing, processing the samples, in parallel, to perform at least one of biochemical reaction on polynucleotides in the containers. In another embodiment at least one of biochemical reaction comprises DNA primer extension or DNA application. In another embodiment the unique nucleotide sequence is a non-natural sequence that is not natural to organisms for polynucleotides in the other containers originated. In another embodiment a plurality of the samples comprise a polynucleotide having a nucleotide sequence unique to that sample.

In another aspect provided herein is a method comprising: attaching different barcodes and barcode set to polynucleotides and each of a plurality of different samples wherein the barcode set is generated using a method as described herein to create tag polynucleotides; sequencing the tagged polynucleotides to produce sequence reads; and assigning the sequence reads to one of the different samples based on the attached barcode.

In another aspect provided herein is a method comprising: sequencing a set of polynucleotides, each tagged with a sample-specific nucleotide barcode sequence, to produce a set of sequence reads of polynucleotides; assigning, by executing a computer program, the sequence reads into different groups representing different samples using a plurality of different stringencies to assign barcode to a sample; generating a receiver operating curve indicating a read at a different stringencies; and selecting a stringency that provides a selected level of sensitivity and specificity.

In another aspect provided herein is a method comprising: A method of sequencing a plurality of nucleic acid samples comprising: attaching oligonucleotides comprising barcodes to nucleic acids in a plurality of nucleic acid samples, wherein the oligonucleotides added to a sample comprise the same sequence and oligonucleotides added to different samples comprise different sequences; sequencing the plurality of nucleic acid samples to produce a plurality of sequence reads; and assigning the sequence reads to a samples corresponding to the attached barcode, wherein a sequence read comprising a single error is still correctly assigned to the sample corresponding to the attached barcode.

In another aspect provided herein is a method for determining sample-to-sample cross-contamination comprising: originally introducing into each of a plurality of containers, a different sample comprising polynucleotides, wherein at least one sample comprises a polynucleotide having a nucleotide sequence unique to that sample; sequencing the polynucleotides in each of the containers to produce sequence reads; determining from the sequence reads, the presence and/or amount of the unique nucleotide in containers into which the unique nucleotide sequence was not originally introduced. In one embodiment the containers are comprised as individual tubes, tubes in a strip, or wells in a multi-well plate. In another embodiment method further comprises, before sequencing, processing the samples, in parallel, to perform at least one of biochemical reaction on polynucleotides in the containers. In another embodiment, at least one of biochemical reaction comprises DNA primer extension or DNA application. In another embodiment, the unique nucleotide sequence is a non-natural sequence that is not natural to organisms for polynucleotides in the other containers originated. In another embodiment, a plurality of the samples comprise a polynucleotide having a nucleotide sequence unique to that sample.

In another aspect provided herein is a method of reducing cross-contamination in a collection comprising a collection of oligonucleotide samples, the method comprising: a) providing a set of different nucleotide sequences; b) performing a plurality of oligonucleotide synthesis reactions, each reaction in the plurality producing a synthesis product in which oligonucleotides having a selected nucleotide sequence from the set of nucleotide sequences comprise a predominant oligonucleotide species, wherein: (1) different synthesis reactions are performed in parallel, wherein reactants and products in each different synthesis reaction travel along different flow paths, or (2) different synthesis reactions are performed in series, wherein reactants and products in a synthesis reaction follow a flow path and wherein, for each synthesis reaction in the series, conduits in the flow path are replaced or cleaned with a nucleic acid destroying agent; and c) assembling a collection comprising a plurality of samples, each sample containing a different synthesis product. In another embodiment, each sample is comprised in a different container. In another embodiment, the containers are contained together in a package as a kit. In another embodiment, nucleotide coupling efficiency in each synthesis reaction is greater than 99.5%, 99.6% 99.7% 99.8% 99.9% or 99.97%. In another embodiment each synthesis reaction comprises nucleotide double coupling reactions.

In another aspect provided herein is a method of reducing cross-contamination of polynucleotides between polynucleotide samples in a collection of samples, the method comprising: a) for each of a plurality of different nucleotide sequences, preparing a sample comprising double-stranded polynucleotides in which one of the nucleotide sequences is a predominant sequence, wherein the double-stranded polynucleotides in each sample are synthesized from a set of partially overlapping oligonucleotides that tile across the nucleotide sequence and that hybridize at overlapping regions; d) assembling the samples into a collection. In one embodiment, the collection comprises a package containing a plurality of containers, each container containing one of the samples. In another embodiment the collection comprises at least 12 samples, at least 24 samples, at least 48 samples or at least 96 samples. In another embodiment the nucleotide sequences are not natural nucleotide sequences. In another embodiment the nucleotide sequences are between 4 nucleotides and 1500 nucleotides in length, between 100 nucleotides and 800 nucleotides in length, or between 250 nucleotides and 500 in length. In another embodiment the oligonucleotides, when hybridize to one another, span the nucleotide sequence with gaps between oligonucleotides on the same street, and wherein synthesizing comprises filling in gaps between oligonucleotides (e.g., by klenow or PCR).

In another aspect provided herein is a method of determining cross-contamination of barcode oligonucleotides between different oligonucleotide samples, comprising: a) providing a plurality of control samples, each control sample comprising one or more predominant control polynucleotide species and having a polynucleotide contamination rate between samples of less than one part per 10,000, one part per 100,000, or one part per 1 million; b) providing a collection of oligonucleotide barcode samples, each sample comprising one or more predominant barcode oligonucleotides and contaminating barcode oligonucleotides, wherein the one or more predominant barcodes define a barcode tag; c) pairing each barcode symbol with a different control sample, and attaching the barcode oligonucleotides and the test polynucleotides in each pairing to produce sets of barcoded control polynucleotides; d) pooling the sets of barcoded control polynucleotides; e) sequencing the barcoded control polynucleotides in the pool to produce sequence information; f) using the sequence information, quantifying combinations of each barcode tag with each control polynucleotide in a barcoded control polynucleotide. In another embodiment, the number of sets is at least 12, at least 24, at least 48 or at 96.

In another embodiment, method further comprises determining, for each of one or more barcode samples, a probability that, in a plurality of barcoding reactions in which the oligonucleotide barcode samples are each paired with a different test sample, a test polynucleotide barcoded with the predominant barcode tag in the barcode sample is a contaminant.

In another aspect provided herein is a sample comprising a collection of polynucleotides, each polynucleotide comprising a nucleotide barcode sequence, wherein the collection comprises a predominant nucleotide barcode sequence and contaminant nucleotide barcode sequences, wherein the contaminants are present in an amount less than one part per 10,000, less than one part per 100,000, less than one part per 1 million or less than one part per 10 million.

In another aspect provided herein is a kit comprising a plurality of containers, each container comprising a collection of polynucleotides, each polynucleotide comprising a nucleotide barcode sequence, wherein the collection comprises a predominant nucleotide barcode sequence and contaminant nucleotide barcode sequences, wherein the contaminants are present in an amount less than one part per 10,000, less than one part per 100,000, less than one part per 1 million or less than one part per 10 million and wherein a plurality of the containers comprise a different predominant nucleotide barcode sequence.

DETAILED DESCRIPTION

Figure 1:
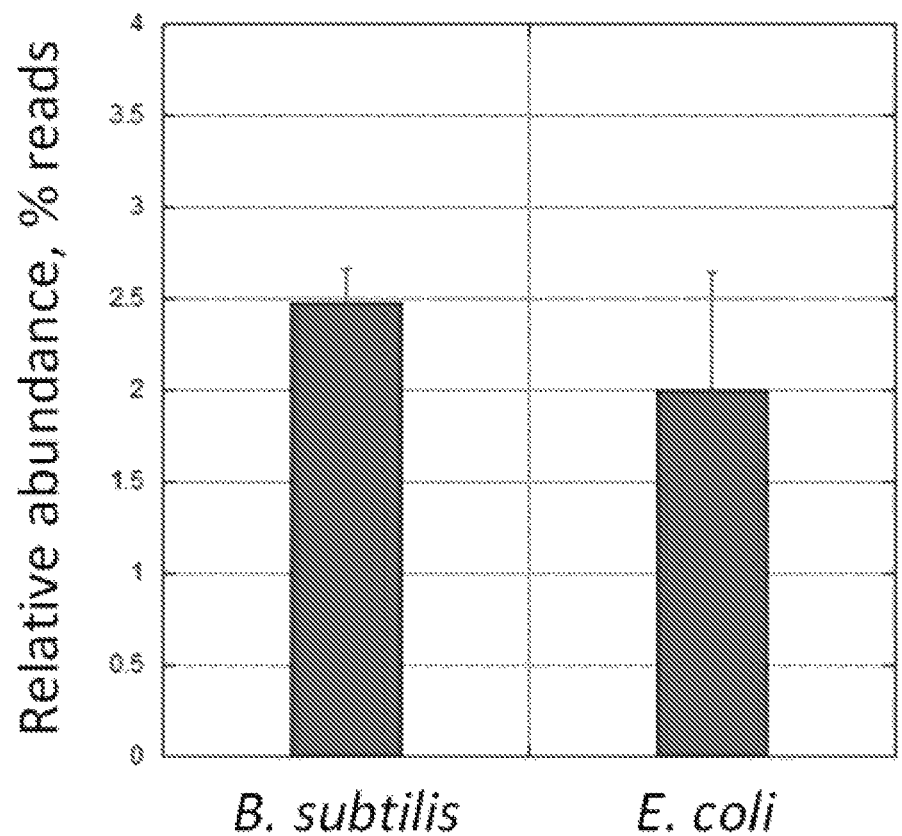
FIG. 1 is graph of the number of sequencing reads as a percentage of total reads that align to each type of bacterium (Gram (+) *Bacillus subtilis* (*B. subtilis*) and Gram (−) *Escherichia coli* (*E. Coli*) that were added to a blood sample, in which the results shown indicate that sample lysis according to embodiments of the present invention is equally efficient for both Gram (+) and Gram (−) bacteria.

For detection, quantification and characterization of organisms, e.g., pathogens or microbes in a subject's gut microbiome, in a sample taken from a subject using next generation sequencing (NGS), aspects of embodiments of the present invention include sample cell lysis followed by an RNA and/or DNA purification process. As used herein, "sample" refers to any biological matter, obtained, e.g., from a subject, from a clinical setting or from the environment. As used herein, "subject" or "host" are used interchangeably to refer to any human or animal for which analysis of some or all microorganisms (e.g., pathogens) is being performed. By implementing efficient laboratory steps, analysis of microorganisms may be performed on any suitable type of sample from a human or animal subject. Suitable types of samples include blood, stool, throat swab, nasopharyngeal swab, sputum, urine, cerebral spinal fluid (CSF), serum, and/or plasma, samples. In some embodiments, a sample from a subject may include any liquid from the subject, e.g., synovial fluid or a homogenized tissue sample. As used herein, an environmental sample can be, e.g., a water sample, a soil sample, an air sample. A clinical sample can be, e.g., a sample taken from a hospital or clinic. An agricultural sample can be from farmland or farm animals.

As used herein, the terms "isolation," "purification," and "extraction" with respect to nucleic acids (e.g., RNA and/or DNA) are used interchangeably to refer to the separation of the nucleic acids from a particular sample. As used herein RNA refers to ribonucleic acid and DNA refers to deoxyribonucleic acid. In some embodiments of the present invention, RNA is isolated from a sample. In other embodiments, DNA is isolated from a sample, and in still other embodiments, both DNA and RNA are isolated from a sample. The type of nucleic acid to be isolated from a sample may depend on the type of sample. For example, there is an abundance of non-pathogenic native DNA (DNA from both the subject and the subject's native bacteria) in stool, blood, and respiratory samples (respiratory samples including sputum, nasopharyngeal swab, and throat swab), and therefore, the isolation and sequencing of pathogenic or microbiome DNA from a sample having an abundance of non-pathogenic DNA may not be an efficacious approach. Furthermore, as bacteria have 10-fold more RNA than DNA, the isolation of RNA with removal of DNA from stool, blood, and respiratory samples will increase the relative amount of bacterial RNA for more effective amplification and sequencing.

As used herein, an "ensemble" refers to a collection of individual items which may be the same or different. For example, an ensemble of barcode molecules refers a collection of individual molecules that may have the same chemical structure or different chemical structures.

A nucleotide sequence "predominates" or is "predominant" if it represents the most common species in a sample or represents more than 50%, 90%, 99% or 99.9% of the species or nucleic acid molecules in a sample.

In some embodiments of the present invention, the sample is urine, which when uninfected, would not contain any cells from the subject or bacteria and would therefore not contain any nucleic acids. As such, for a urine sample, as there should not be an abundance of any type of nucleic acid in a healthy subject, both DNA and RNA may be isolated and amplified for sequencing and microorganism (e.g., pathogen) identification.

In some embodiments, the sample obtained from a subject may be immediately processed. Processing of the sample includes isolation (i.e., purification or extraction) of the nucleic acids present in the sample for sequencing and identification.

In some embodiments, the sample from a subject is stored until processing. In some embodiments, the sample is stored at −20° C. to −80° C. In some embodiments, all types of samples are stored at −80° C. In some embodiments, all types of samples, except urine, are stored at −20° C. to −80° C. Accordingly, samples including blood, stool, throat swab, nasopharyngeal swab, cerebral spinal fluid (CSF), serum, plasma, and/or sputum samples may be stored at −20° C. to −80° C. In some embodiments, urine samples are stored in a refrigerator, for example, at 4° C.

In some embodiments, samples are pre-treated prior to isolation of nucleic acids. In some embodiments, if the sample is frozen (at −20° C. to −80° C.), the sample is first thawed prior to pretreatment. As used herein, "pre-treatment," "pre-treating," and like terms, refers to processing of the sample for preservation of the molecular components of the sample prior to nucleic acid isolation. For example, in some embodiments, the samples are pretreated with a nucleic acid preservative (e.g., TRIzol®, Life Technologies). In some embodiments, for a urine sample, the urine is first centrifuged to pellet any microorganisms (e.g., bacteria) and the pellet is resuspended in a nucleic acid preservative. After pretreatment with a nucleic acid preservative, the sample may be stored at −20° C. to −80° C. or in the case of urine, the sample is stored at 4° C.

In some embodiments, in order to isolate RNA and/or DNA from the sample, the sample is first processed for lysis of some or all cells in the sample. In some embodiments, the sample is a pretreated sample suspended in a nucleic acid preservative. If the sample has been stored at −20° C. to −80° C., the frozen sample is first thawed on ice. A thawed sample or a sample on ice is vortexed until thoroughly homogenous. A portion of the homogenous sample is lysed. In some embodiments, the sample portion is lysed by bead beat lysis or homogenization. For example, a portion of the sample may be placed in a bead beat lysis tube with lysis beads and homogenized according to any suitable protocol. For example, bead beat lysis of the sample may include following a Fast Prep (MP Biomedicals, LLC) protocol. After homogenization, the sample is centrifuged, and the supernatant containing the lysed cellular material is collected into a separate tube for further processing.

In some embodiments of the present invention, nucleic acids including DNA and/or RNA are purified from the lysed cellular material of the sample. Purification (i.e., isolation or extraction) of DNA and/or RNA from the lysed cellular material is carried by any suitable DNA or RNA purification material. For example, nucleic acid purification may be carried using a Zymo Research DNA or RNA purification kit and protocol. Purification of DNA and/or RNA from lysed cellular material of a non-urine sample results in the purification of some or all types of RNAs (ribosomal RNA (rRNA), transfer RNA (tRNA), and messenger RNA (mRNA) from the subject's (e.g., human) cells, from healthy (non-pathogenic) bacterial cells, as well any from the pathogenic (viral or bacterial) RNA to be identified.

Following the processing and lysis steps according to embodiments of the present invention, both Gram positive (+) and Gram negative (−) bacteria are effectively lysed, and as such, RNA and/or DNA from both types of bacteria may be effectively purified and sequenced. For example, as shown in FIG. 1, sequencing of total RNA from a blood sample spiked with equal amounts of both *Bacillus subtilis* (Gram +) and *Escherichia coli* (Gram −) resulted in comparable sequencing reads.

Figure 2:
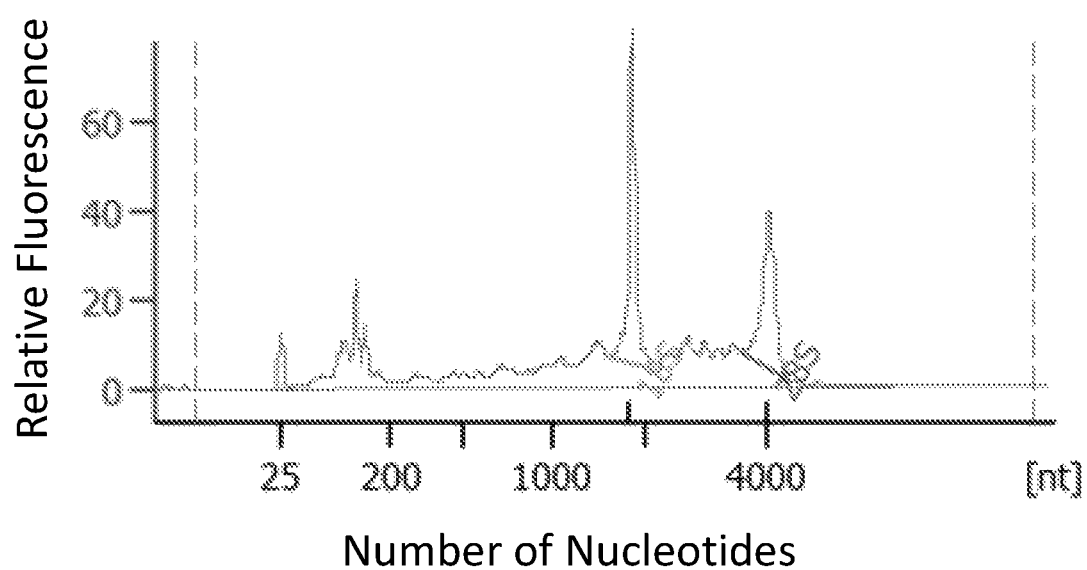
FIG. 2 is a graph of relative fluorescence as a function of the number of nucleotides (nt) obtained from an Agilent BioAnalyzer 2100 instrument and Agilent RNA Pico Chips from total RNA purified from a blood sample that was stored in a freezer (−80° C.) for a year, the peaks representing the 18S ribosomal RNA and 28S ribosomal RNA are labeled, according to embodiments of the present invention.

Following the processing and lysis steps according to embodiments of the present invention, high yields of RNA and/or DNA are obtained with high integrity. For example, as shown in FIG. 2, RNA was purified according to embodiments of the present invention, from a blood sample that was processed and then stored in a freezer (−20° C. to −80° C.) for a year according to embodiments of the present invention.

In some embodiments of the present invention, after purification of DNA and/or RNA from blood, stool, or respiratory samples (including sputum, nasopharyngeal swabs, and throat swabs), the DNA and/or RNA sample is further processed to remove RNA. This process of removal of non-informative RNA (RNR) allows for the removal of human ribosomal RNA (rRNA), human transfer RNA (tRNA), human messenger RNA (mRNA), bacterial rRNA, and bacterial tRNA, thereby leaving bacterial mRNA and/or viral RNA for further amplification and sequencing.

Removal of Non-informative RNA (RNR)

Figure 3:
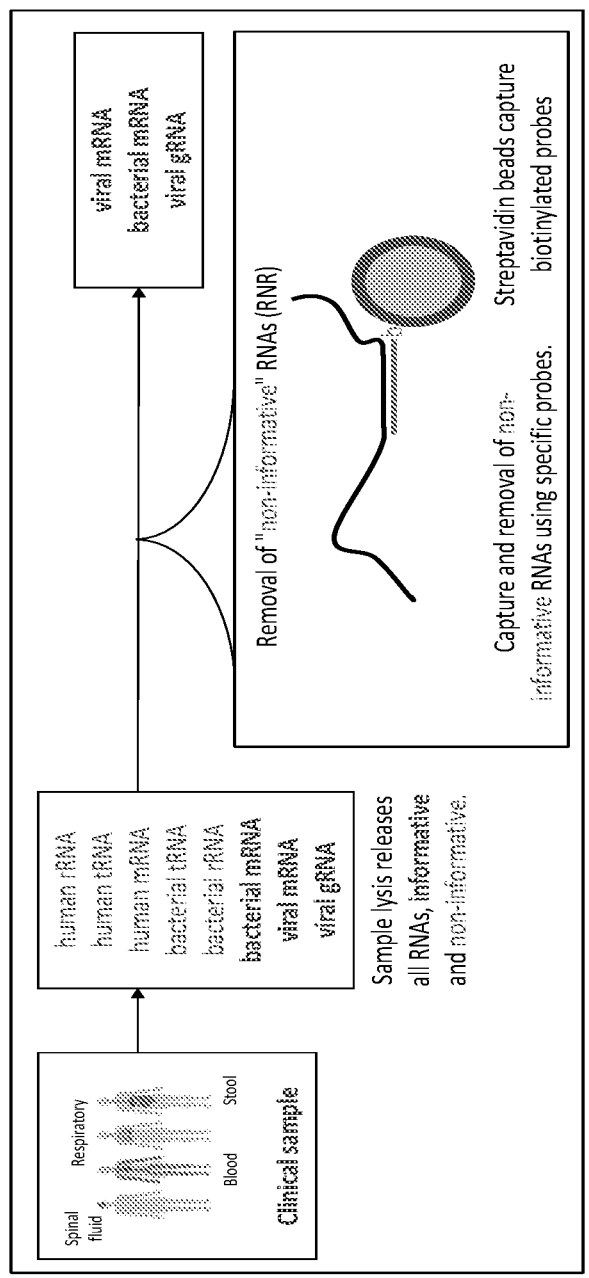
FIG. 3 is a schematic depicting the removal of non-informative RNAs (RNR) as a laboratory method that physically removes non-informative RNAs from the total RNA using nucleic acid probes designed to hybridize to non-informative RNAs followed by removal of the probe and probe-RNA complex, according to embodiments of the present invention.

As depicted in FIG. 3, total RNA isolated from any type of sample is largely made up of RNAs, including eukaryotic host ribosomal RNA (host rRNA), commensal bacterial ribosomal RNA (non-pathogenic bacterial rRNA), the host's transfer RNA (tRNA) and the host's messenger RNA (mRNA) in addition to the RNA from the pathogen (viral or bacterial) to be identified. In some embodiments of the present invention, RNA representing the subject's (i.e., host's) native RNA and non-pathogenic or microbiome RNA is removed from the total purified RNA or from the total combination of both the purified DNA and RNA isolated from the lysed cellular material of a non-urine sample. As such, the removal of non-informative RNA (RNR) process allows for a concentration and selection of the RNA that originates from less abundant microorganisms, such as pathogens. This concentration step may also be referred to as a "decluttering" step.

In some embodiments of the present invention, the RNR process is performed on the sample using substrate-linked oligonucleotide probes (e.g., bound to a solid substrate such as a bead or a column matrix) that hybridize specifically to the background RNA found in the purified RNA or purified DNA and RNA from a sample. For example, the RNR process may be used to remove background RNA found in stool, blood, or respiratory samples that contain an abundance of human and non-pathogenic bacterial RNA.

In generic terms, RNA extracted from any sample that contains microorganisms (e.g., from a subject, soil, water, clinical, etc.) will mostly be made up of non-informative RNAs (e.g., rRNA), that is, RNA that are not specific to the microorganisms in question. RNR method can be used to remove the non-informative RNAs from any sample type, using different or universal RNR probes. Applications of this technology extend to agriculture, food safety, forensics, environmental remediation, biofuel production, biomanufacturing, algal blooms, health and monitoring of aquatic environments, etc.

In some embodiments of the present invention, the RNR probes are designed for a specific sample type. For example, the human RNA and non-pathogenic bacterial RNA in a stool sample will differ from the human RNA and non-pathogenic bacterial RNA. Accordingly, the set of RNR oligonucleotides used for a human stool sample are different from the set of RNR oligonucleotides used for a human blood sample. In some embodiments, the set of RNR oligonucleotides used for a human respiratory sample includes the sets of RNR oligonucleotides for human stool and for human blood samples.

In some embodiments of the present invention, the RNR process on RNA or both DNA and RNA purified from a human respiratory sample (e.g., sputum, nasopharyngeal swab, and throat swab) includes removing RNA using the oligonucleotide probes used for both the human stool and blood samples.

In some embodiments of the present invention, the RNR probe oligonucleotides include an isolation tag for easy removal of the hybridized RNR probe and background RNA. For example the RNR probe oligonucleotide may be biotinylated at the 3' end for effective removal through binding of the biotin to streptavidin. For example, after hybridization of a purified RNA or DNA and RNA sample with a set of RNR probe oligonucleotides specific to the sample, the hybridized non-informative RNA is removed from the sample using streptavidin-coated magnetic beads.

The RNR process according to embodiments of the present invention is inexpensive, requires approximately 30 minutes of time, and may be automated. RNR may be customized with corresponding oligonucleotide RNR probes for many if not all relevant samples from a subject with a cost of approximately $10 per sample.

Figure 4:
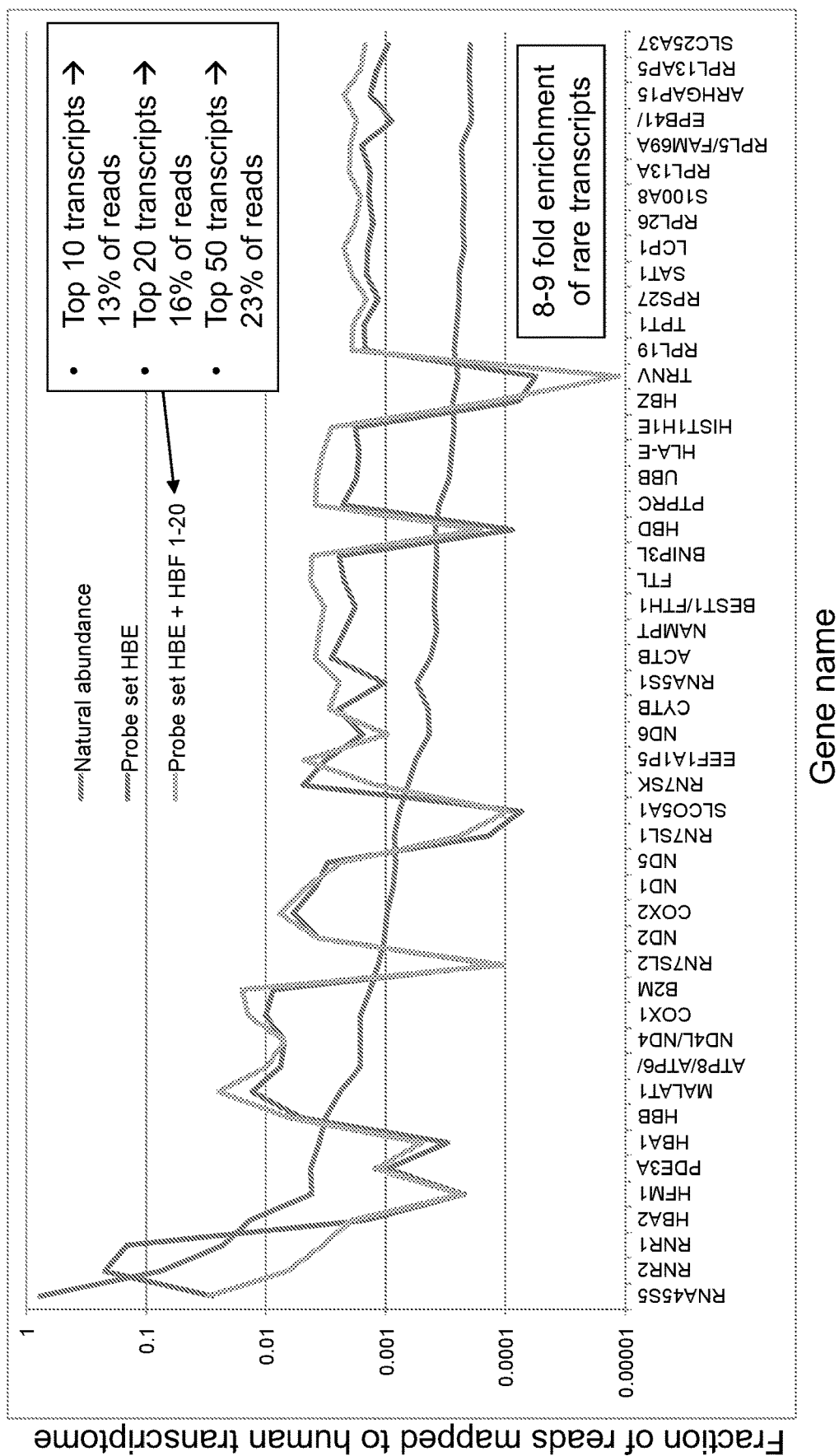
FIG. 4 is a graph of the RNR process applied to human blood, the graph showing relative abundance (Y axis) of the most abundant human blood transcripts (indexed along X axis) in which natural abundance of human blood RNAs are shown in blue (in this case, the line that starts at the top left of the graph); the graph shows that RNR removes abundant host RNAs while increasing the relative abundance of RNAs that come from less abundant microorganisms (e.g., pathogens), where HBE (human blood group E) set of RNR probes (shown in red, in this case, the line that starts in the middle on the left of the graph) and HBE and HBF (human blood group F) RNR probes (shown in green, in this case, the line that starts on the bottom from the left of the graph) enrich rare sequences (e.g., from pathogens) by approximately 8 to 9 fold, according to embodiments of the present invention.
Figure 5:
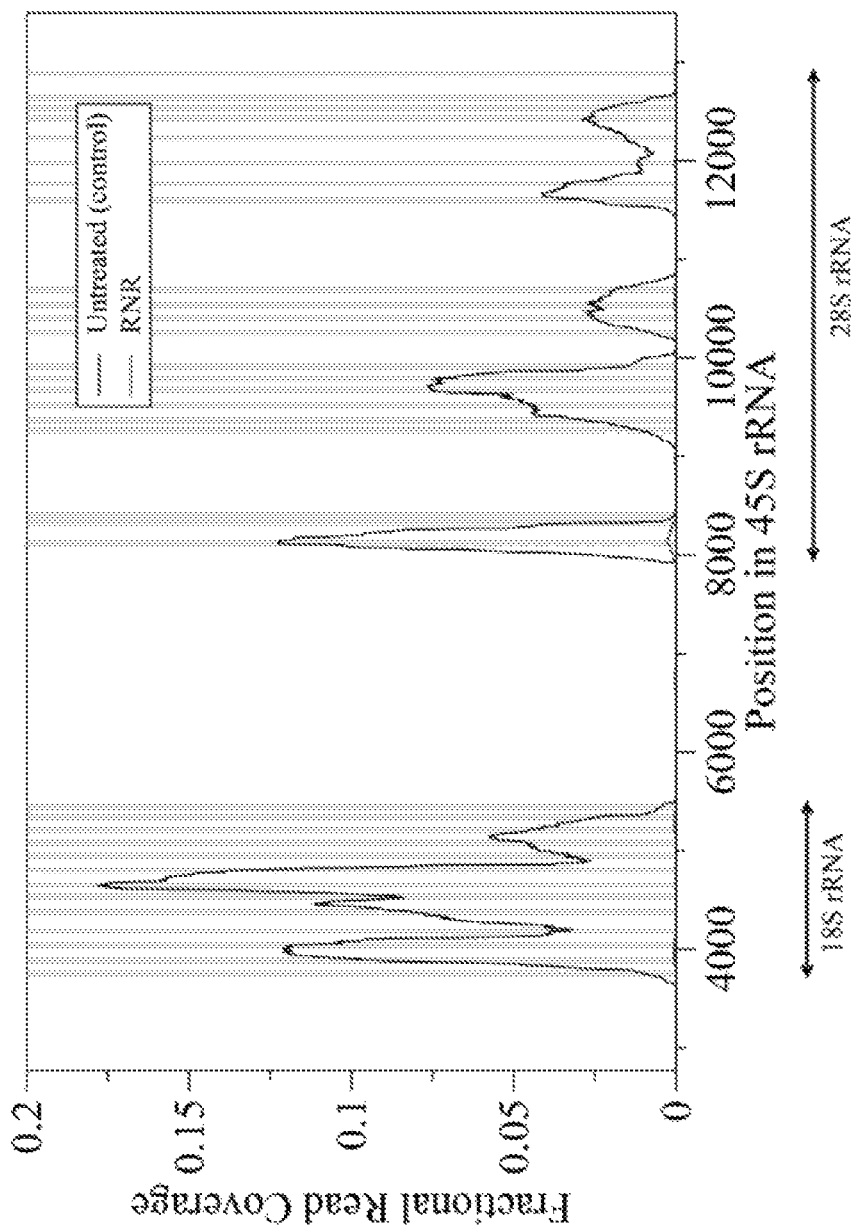
FIG. 5 is a spectrum of a sequencing read of the RNR process applied to human blood in which the sequencing reads that map to the human 45S RNA transcripts are shown with (small peak at approximately position 8000) and without (in black, large peaks) the RNR process, according to embodiments of the present invention.

As shown in FIGS. 4 and 5, the RNR process according to embodiments of the present invention removes abundant host RNAs (e.g., 45S RNA in FIG. 5) while increasing the relative abundance of RNAs that come from less abundant microorganisms.

Library Preparation of RNR-processed RNA.

Using the RNR-processed enriched RNA from a subject's sample, further embodiments of the present invention include methods for converting this enriched RNA into Illumina sequencing libraries.

The methods according to embodiments of the present invention as described in Example 4 provide an easy, rapid, inexpensive, sensitive, and automatable process for preparing a DNA fragment library of the enriched RNA sample for sequencing and subsequent analysis. The library preparation process includes fragmenting the RNR-processed RNA and synthesizing double stranded (ds) complementary DNA (ds cDNA). This cDNA is then cleaned and size-selected prior to polymerase chain reaction (PCR) amplification. The cDNA is amplified with a selected barcode oligonucleotide during the PCR process. The PCR product is then cleaned and validated (e.g., the concentration and average size of the library is determined) prior to sequencing.

Barcodes can be attached to the polynucleotide fragments by any method known in the art. This includes, for example, performing a primer extension reaction on a primer comprising the barcode that is hybridized to the polynucleotide fragment of interest. It also includes, ligating polynucleotide comprising barcodes to blunt or sticky ends of the polynucleotide fragments.

Figure 6:
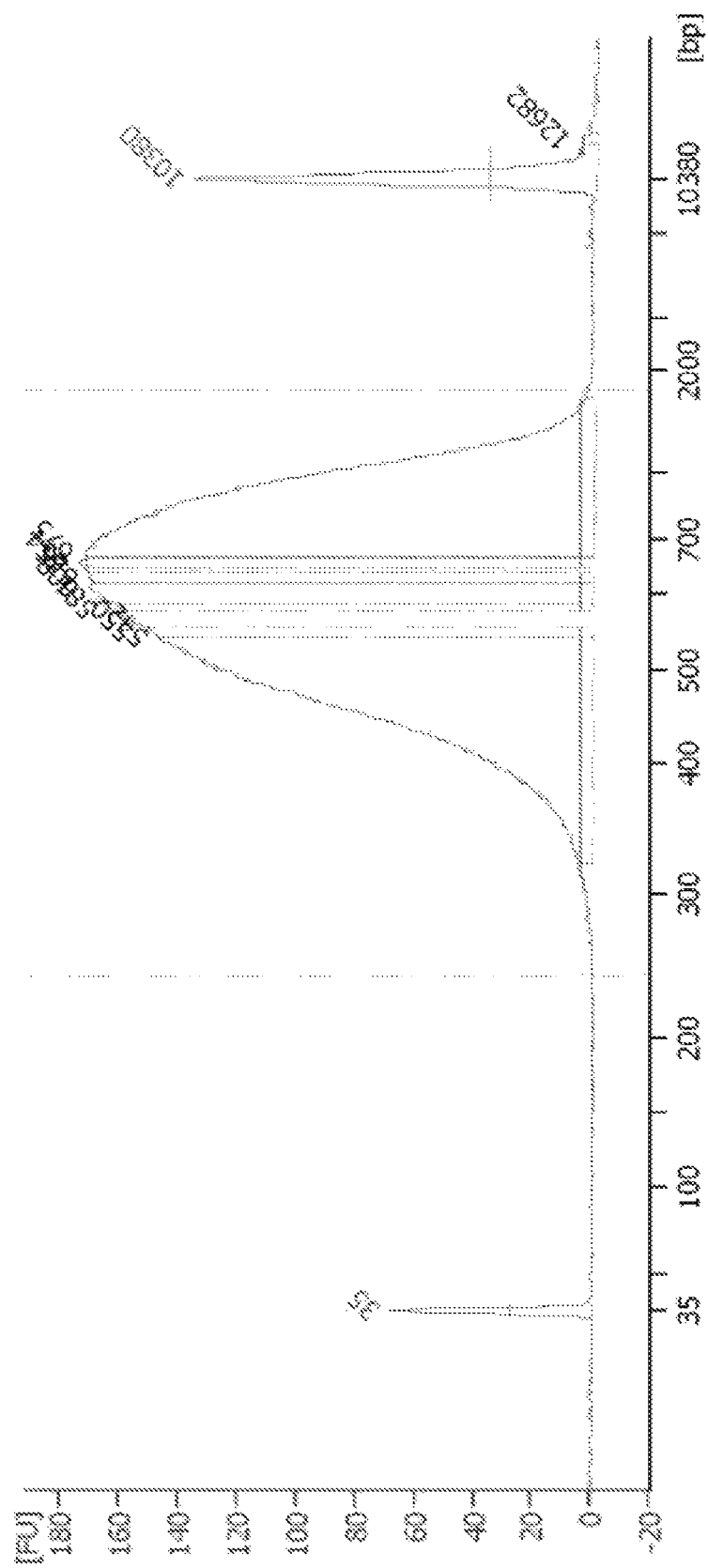
FIG. 6 is a representative graph of the relative amount and size (base pairs, bp) cDNA fragments in a library prepared from 10 ng human blood RNA, according to embodiments of the present invention.

The DNA library preparation process according to embodiments of the present invention generates high quality libraries from as low as 1-10 nanograms of RNA. DNA libraries prepared according to embodiments of the present invention including methods disclosed herein, do not contain primer-dimers or adapter-dimers, and their average size (approximately 600 base pairs (bp)) is suitable for sequencing on Illumina platforms with few if any overlapping reads. The DNA fragments from a library made from 10 ng of RNA processed from human blood according to embodiments of the present invention is shown in FIG. 6.

Sequencer-Customized Barcode Design

As discussed above, the microbial RNAs isolated from the sample are amplified and sequenced. Amplification can be performed using a technique such as reverse transcriptase polymerase chain reaction (RT-PCR) to generate sequencing libraries. Sequencing can be performed by a DNA sequencer produced by companies such as Illumina® Inc. of San Diego, California.

Figure 7A:
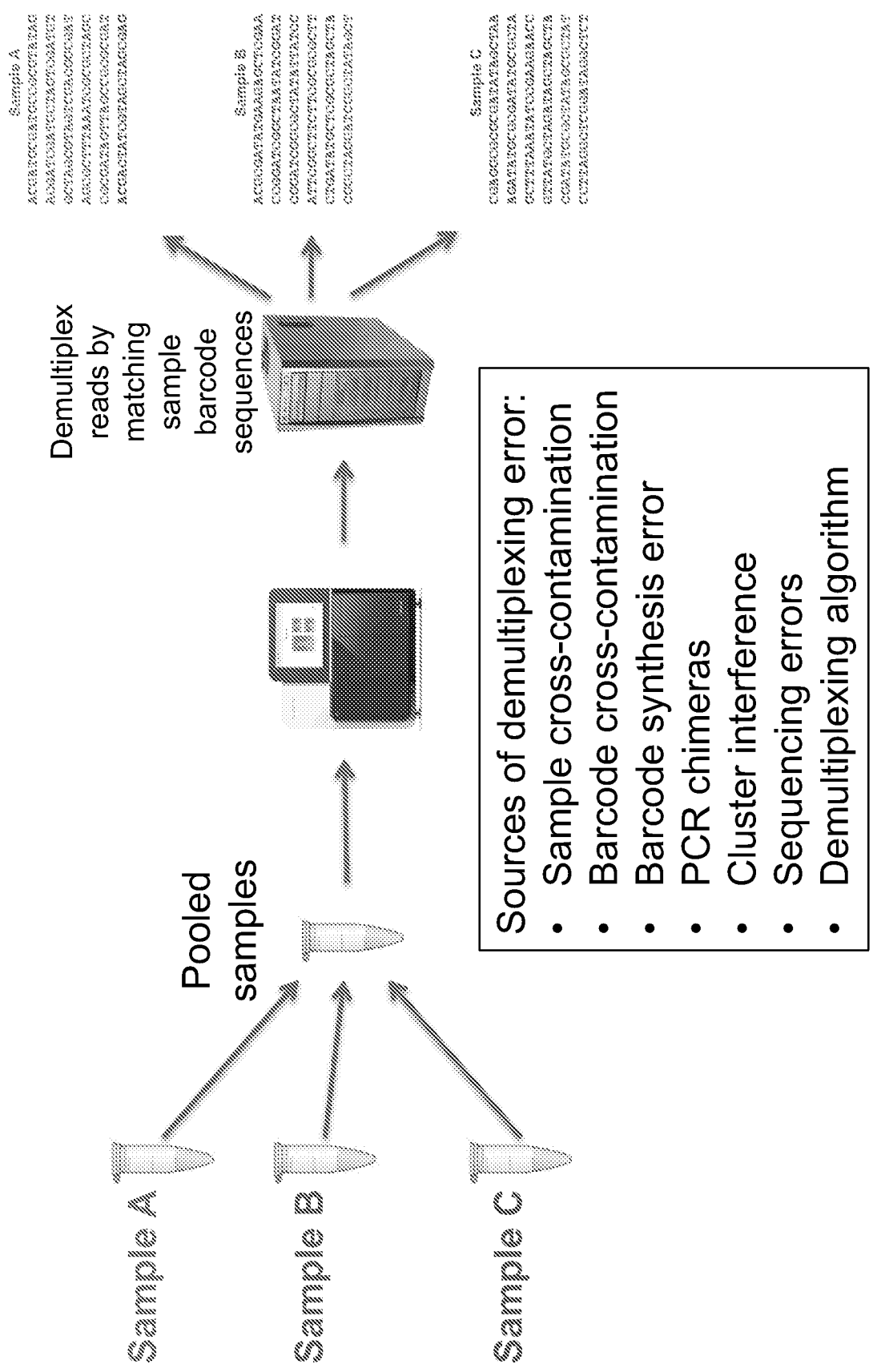
FIG. 7A is a schematic of sample multiplexing and demultiplexing of pooled samples using barcode sequences, according to embodiments of the present invention. Sequences are provided for Sample A (SEQ ID NO: 1), Sample B (SEQ ID NO: 2), and Sample C (SEQ ID NO: 3).

FIG. 7A is a schematic of sample multiplexing and demultiplexing of pooled samples using barcode sequences, according to embodiments of the present invention.

As shown in FIG. 7A, in order to reduce the time and cost associated with amplification and sequencing of microbial RNA collected from a single sample, multiple samples can be pooled (multiplexed) into the same run of the sequencing instrument. These multiple samples may be collected from different subjects. After sequencing, the sequenced reads are separated (demultiplexed) into sample-specific data files by sorting each read according to a sample-specific barcode sequence that was integrated into the amplified strands. The process of applying barcodes is independent of sequencing platform and chemistry.

Generally, if there were no errors in reading the barcode sequences, the demultiplexing process would be error-free and the barcode design process would be trivial. However, in practice, errors can arise in various parts of the process, including barcode oligonucleotide synthesis, barcode oligonucleotide purification, sample preparation (including PCR amplification), the sequencing, and demultiplexing process. These errors can complicate the process of sample demultiplexing and can cause demultiplexing errors (e.g., a sequenced read belonging to Sample A is incorrectly assigned to Sample B because the various errors have caused its barcode to appear more like the barcode for Sample B than the barcode for Sample A). Demultiplexing errors can be thought of as a source of sample cross-contamination that must be avoided in applications that require high accuracy (e.g., clinical diagnostics).

In barcode synthesis any product of the synthesis reaction may not have an entirely homogenous ensemble of oligonucleotides. Typically, oligonucleotides with the intended sequence predominate, that is, the most common species of oligonucleotide in the sample. However, other oligonucleotides can be present as contaminants. During the manufacture of sample barcodes, barcode samples may be contaminated at a rate of, e.g., 0.2 to 0.4% contamination. These contaminants can include products of synthesis error as well as products of other sequencing reactions performed, for example, on the same equipment. Both of these types of contaminants can be reduced so as to be present in a sample in less than one part per thousand, less than one part per 10,000, less than one part 100,000, or less than one part per million.

Synthesis errors can include failure to add a nucleotide to every molecule in the ensemble at each step. Sometimes, additions to certain molecules in the ensemble may be terminated. This results in some molecules being shorter than others and, consequently, having different sequences. Methods of decreasing contaminants due to synthesis error can include increasing nucleotide coupling efficiency during the synthesis process. For example, coupling efficiency can typically be 99%. Accordingly, the methods can be used that increase coupling efficiency to greater than 99.5%, 99.6% 99.7% 99.8% 99.9% or 99.97%.

One such method to achieve this is the use of nucleotide double coupling reactions. Double coupling reactions involve addition of a nucleotide phosphoramidite, coupling it to the growing polynucleotide chain, washing away the uncoupled nucleotide, and then repeating the coupling process with a fresh batch of the same nucleotide phosphoramidite.

Contaminants from other synthesis reactions can occur when reactants and products of synthesis reactions travel along the same flow paths in instrument. This includes, for example, fluid conduits connecting liquids from a synthesizer to an isolation column (e.g., a C18 column,), the isolation column itself and fluid conduits being purified samples away from the isolation column. One method of decreasing such contaminants is to make each barcode on a different synthesis system and to dedicate each system to a single barcode. Another method of decreasing such contaminants is to wash some or all surfaces into which reactants and products come into contact with a chemical that degrades nucleic acids. One such chemical is bleach. In certain cases, such as isolation columns, destruction of contaminating oligonucleotides can be difficult. In this case, the elements can be replaced between synthesis runs, in particular, runs producing different sequence barcodes.

Samples constituting a set of barcodes can be assembled into a collection and packaged as a kit in which each sample is contained in a different container in the collection of containers is packaged together. The container can be, for example, a box, package, bag, tube or jar.

Sample-to-sample cross contamination may result in confusion when molecules found to be present in one sample actually are contaminants from another sample, as can happen via aerosol contamination.

Random and systemic sequencing errors during the sequencing process introduce further errors. In some instances, different positions along the length of a nucleic acid can be more prone than others to particular read errors or read errors in general. For example, each position can have a systematic error, which can be detected and quantified. In one position, a T may be more likely to be misread as an A than at another position. In another example, the probability that a T at one position is misread as an A may be higher than the probability that the T is misread as a G.

Some barcode positions are more prone to errors than others. Surprisingly, the first few nucleotides of a barcode can be less accurate than the rest of the barcode. This is counter to some expectations about massively parallel sequencing methods in which the accuracy of a base call is thought to decrease as the read progresses.

The methods described herein can account for errors and biases at various positions to minimize the chance that one barcode will be misidentified as another barcode or that the barcode cannot be identified with confidence.

In some instances, the error can be caused by a polymerase used in a sequencing reaction, including sequencing by synthesis reaction, introducing an incorrect base. Nucleotides used during sequencing reactions are often labeled with a fluorescent label. Such labels can interfere with an enzyme's, such as a polymerase's, ability to attach the nucleotide to the growing copy strand. For example, the fluorophore may interfere with the nucleotide's ability to fit into the active site of the enzyme.

In another example, the enzyme may be more error prone when adding a particular base (e.g., A, T, G, or C) the preceding nucleotide on the copy strand. Such errors can be due to the identity of the added base, the preceding base, or a combination of the two. For example, certain pairs of bases may be more error prone than others. In another example, the fluorophore can interfere with certain pairs of nucleotides more than others. Errors in synthesizing the copy strand can include particular biases. These biases can be measured and used to design instrument-specific barcodes that account for the particular machine and/or the particular enzymes, chemistry, and reagents used in a sequencing reaction.

For these reasons, it is important to design barcodes that account for error-based misidentification. Barcodes that minimize read errors can offer several advantages. On exemplary advantage is the ability to improve sequencing yields. In many demultiplexing methods, sequence reads that include a sample barcode that cannot be identified with confidence are often discarded. The ability to tailor the barcodes to reduce such errors increase efficiency because a larger percentage of reads can be identified as belonging to one sample or another with confidence. As a result, more reads can be classified for a given amount of DNA. Alternatively or in addition, a sample can be analyzed with a certain read depth with fewer total reads. This can allow for higher read depth and/or the analysis of more samples in a single sequencing run.

Existing barcode design techniques merely consider that the barcodes are distinct from one another by a specified minimum edit distance, where the edit distance is the number of base substitutions required to transform one sequence to another. (For example, the edit distance of the sequences AGGTC and ACGAC is 2, because the first G of the first sequence is substituted with a C in the second sequence, and the T of the first sequence is substituted with an A in the second sequence.) These approaches implicitly assume that all of the sources of error in the measured barcode sequences are uniform in both base position and base composition. However, in practice, barcode errors are both position dependent and composition dependent.

Aspects of embodiments of the present invention are directed to systems and methods for designing and synthesizing barcode sequences that reduce demultiplexing errors by explicitly accounting for the position dependence and composition dependence of barcode errors. Aspects of embodiments of the present invention are also directed to methods for characterizing the error rates of a sequencer. The systems and methods for designing barcodes may then customize barcodes for a particular sequencer based on its error characteristics.

In the below discussion, estimates of sequencing errors will be expressed as follows: the probability of observing a particular base obs (e.g., a sequencer outputting a particular base) at a given position pos in a barcode sequence of length N and given the actual base act at position pos in the actual barcode sequence is written as $$P_{error}(obs|act,pos)$$

where:
obs∈{A,T,G,C}
act∈{A,T,G,C}
0≤pos<N

Because all of the parameters of $P_{error}$ are or can be finite sets (e.g., there are four possible observed bases, four possible actual bases, and N possible positions), the probability function Perror can be expressed as a three dimensional (4×4×N) matrix, such that evaluating the error probability function amounts to looking up the value in the matrix that corresponds to some given (obs, act, pos) parameters.

The values of the probability function Perror, in other words, the 4×4×N cells of the matrix, can be experimentally estimated for a given sample preparation method and sequencing platform by analyzing a set of raw training data collected by using the sequencer to sequencing a set of training barcode sequences.

In some embodiments, error rate, as it applies to demultiplexing barcode sequences, refers to the probability that a barcode having a first nucleotide sequence will be read in a sequencing protocol as another, different barcode sequence in the set. Error can arise during synthesis of the barcodes in the barcode set and from laboratory operations, including errors introduced during sample preparation, e.g., amplification, and errors made by the sequencing instrument. Barcode reads in a sequencing protocol can be treated in a number of ways. In one embodiment, a barcode read that does not correspond to any barcode in the set of barcodes is discarded. In another embodiment, a barcode read that differs from a barcode in the set by an edit distance of no more than 1, no more than 2, no more than 3 or no more than 4 can be assigned to that barcode, in some cases as long as there no other barcode in set to which the read has a closer edit distance.

Instrument-specific refers to a specific sequencing instrument and can also include operations in a sequencing protocol used to prepare a sample for sequencing, for example, adapter ligation or DNA amplification, for example, as provided in kits to be used with a particular sequencing instrument. For any sequencing protocol, a set of barcodes will have a demultiplexing error rate. A barcode set can be selected such that, for any specific sequencing instrument and/or sequencing protocol, the barcode set has a demultiplexing error rate less than or no more than a threshold value. The threshold can be, for example, no more than or less than any of 5/1000, 1/1000, 1/10,000, 1/100,000, 1/1,000,000 1/10,000,000 or 1/100,000,000.

Accordingly, instrument-specific barcodes can be a set of barcodes which, for a specific sequencing instrument and, typically, with specific reagents used to prepare a sample for sequencing, produces a demultiplexing error rate below a selected threshold value.

Figure 7B:
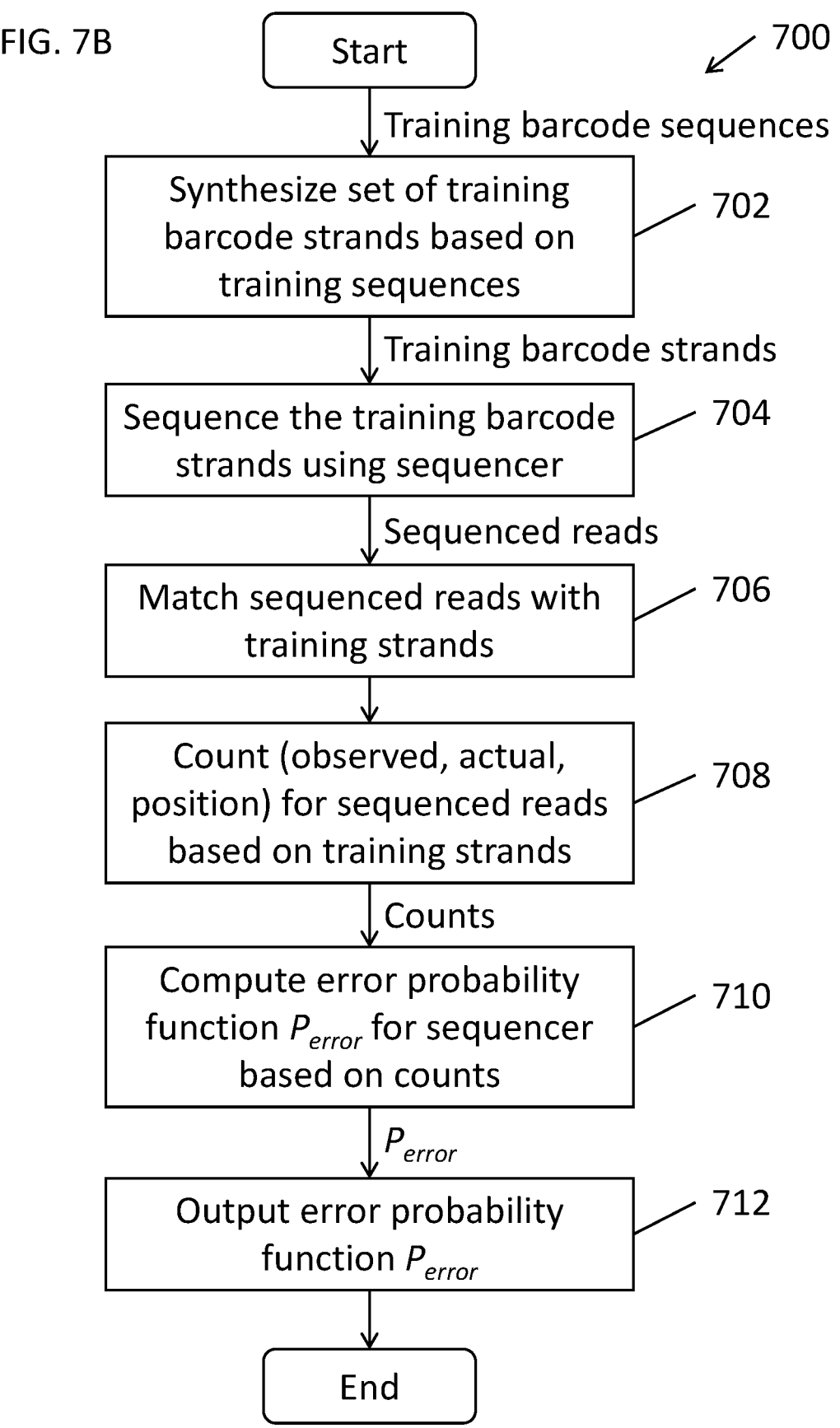
FIG. 7B is a flowchart illustrating a method according to one embodiment of the present invention for characterizing the sequencing error probabilities of a sequencer to generate an error probability function.

FIG. 7B is a flowchart illustrating a method 700 according to one embodiment of the present invention for characterizing the sequencing error probabilities of a sequencer to generate an error probability function. In operation 702, a set of training barcode sequences are synthesized to form a set of training barcode strands.

According to some embodiments of the present invention, four different training barcode sequences are used, where each nucleotide (A, T, G, or C) appears at each position pos in at least one of the training barcode sequence. For example, for N=6, one set of training barcode sequences is:

```
ATTGCG

TACTGA

GGAATT

CCGCAC
```

As seen in the example sequences above, each nucleotide appears at least once in any given column, where each column corresponds to the same position pos within the training barcode sequence. As such, a minimum of four distinct barcode sequences are required to fully characterize the matrix.

However, because the errors made by the sequencer also depend on higher order combinations of adjacent nucleotides (e.g., pairs of bases AA, AT, AG, . . . ), in other embodiments of the present invention, more than four distinct barcode sequences are used to generate the training data. For example, when accounting for pairs of bases, at least 16 barcodes can be used to characterize the matrix. These additional distinct barcode sequences can average out the differences that arise from the various additional combinations of nucleotides.

In operation 704, the training barcode strands are sequenced using a sequencer to generate a sequencer output, referred to as sequenced reads. These sequenced reads are digital information (e.g., a text file). In some embodiments of the present invention, each distinct barcode sequence is sequenced separately by the sequencer. In other embodiments of the present invention, the set of barcode sequences are sequenced together. As described below, the method generally includes sequencing a plurality of molecules for each barcode sequence and counting the number of occurrences of each nucleotide in each position of that particular barcode in order to detect patterns in read errors.

After sequencing the set of training barcode sequences using the sequencer in operation 704, the sequencer output can then be analyzed to fill in the cells of the 4×4×N matrix by counting the number of occurrences of each (obs, act, pos) tuple for each of the sixteen combinations of pairs of nucleotides at each position of the barcode. Thus, the method can include comparing the observed or detected nucleotide at each position to the actual or expected nucleotide at that position.

Embodiments of the present invention may implement the analysis using, for example, a computer system including a processor and memory that stores instructions to be executed by the processor. In various embodiments, the processor may be a general purpose central processing unit or a microprocessor, a vector processor such as a graphical processing unit (GPU), customized hardware such as a field programmable gate array (FPGA), or an application specific integrated circuit (ASIC). In some embodiments of the present invention, various parts of the process may be spread across multiple different processors and/or different types of processors, where data may be communicated between the different processors.

In embodiments where the training barcode sequences are sequenced together, in operation 706, the processor sorts the sequenced reads found in the raw sequencer output into groups by identifying the closest matching training barcode sequence. This match may be based on similarity in accordance with edit distance. In other embodiments, the sequence of the actual training barcode corresponding to a given observed barcode is inferred by restricting the counting analysis to only those observed barcodes that are either zero or one edit away from an actual training barcode. Because the barcode sequences typically are not included in standard FASTQ sequencer output, the raw sequencer output may be used instead for this analysis.

In operation 708, the processor counts the number of times a nucleotide is observed (obs) in the sequenced reads for a given actual nucleotide (act) in the corresponding (matched) training barcode sequence at each position (pos). Through this counting, the processor fills the 4×4×N matrix.

The 4×4×N matrix can be thought of as N 4×4 sub-matrices, where each sub-matrix corresponds to one position pos, and each sub-matrix has rows and columns labeled with nucleotides. The different rows may represent the different actual bases act, and the different columns represent the different bases observed obs in the output of the sequencer. The values in the matrix correspond to the counts. The below table is one example of a 4×4 sub-matrix for one position pos. The first row corresponds to the case where the actual training barcode sequence has an "A" nucleotide at position pos, and the set of sequenced reads shows 11000 occurrences of the correct nucleotide "A". The first row also shows that the actual "A" nucleotide was incorrectly observed 30 times as "T", incorrectly observed 60 times as "G", and incorrectly observed 10 times as "C".

|   | A | T | G | C |
|---|---|---|---|---|
| A | 11000 | 30 | 60 | 10 |
| T | 40 | 9940 | 60 | 110 |
| G | 86 | 15 | 10190 | 80 |
| C | 61 | 10 | 140 | 9809 |

According to one embodiment of the present invention, the processor iterates over the set of sequenced reads corresponding to a given training barcode sequence and updates the output matrix by incrementing (adding one) to the locations in the matrix given by the tuples of the form (obs, act, pos). In the case where each run of the sequencer uses only a single training barcode sequence, all of the sequenced reads will correspond to the single training barcode sequence. In the case where multiple are run, the closest matching training sequence may be used.

For example, if the training barcode sequence is ATTGCG and the sequenced read is ACTGGG, then the processor increments the counts at locations (A, A, 0), (C, T, 1), (T, T, 2), (G, G, 3), (G, C, 4), and (G, G, 5). As a part of the counting-based estimation process, a pseudo-count of one is added to each element of the matrix $P_{error}$(obs|act, pos) in order to set a lower bound greater than zero on the value of each probability value, which has an effect when computing the logarithm of the probability, as described in more detail below.

As a result, in operation 710, the processor computes the full 4×4×N matrix for the estimated function $P_{error}$ by counting the (obs, act, pos) values for some or all of the sequenced reads across some or all of the training barcode sequences, and, in operation 712, outputs the error characteristics of the sequencer $P_{error}$ (obs|act, pos) for use in designing barcode sequences. (These counts can be normalized by dividing each value by the sum of the counts for a given actual base act.)

This method can also be performed using more than four training barcodes. In such cases, each nucleotide (A, T, G, or C) can appear at each position pos in at least one of the training barcode sequences. The use of more than four barcodes can allow for various combinations of nucleotides to be assessed at a variety of positions. Error reads at various positions can be assessed with greater depth. In some instances, pairs of nucleotides in adjacent positions can be assessed. In such cases, pairs of nucleotides can be positioned along the length of the barcode and sequenced to quantify the error rate.

The length of the training barcodes (N) can be or can be at least 5, 6, 7, 8, 9, 10, 11, 12, 13, 14, or 15 nucleotides long. In other cases, the length of the training barcodes can be less than 5, 6, 7, 8, 9, 10, 11, 12, 13, 14, or 15 nucleotides long.

According to one embodiment of the present invention, a method for designing a set of barcodes includes selecting a set of barcodes that reduces or minimizes the demultiplexing error by reducing or minimizing the likelihood that errors will cause one of the barcode sequences to appear to be more similar to a different barcode sequence in the same set.

Formally, the barcode design process may be considered an optimization problem that explores the space of possible barcode sequences to minimize the probability of experimental errors that will cause one barcode to appear as another. In one embodiment, the objective function to be minimized is:

$$\Theta = \sum_{i=0}^{M-1} \sum_{j=i+1}^{M-1} \rho(\sigma_i | \sigma_j) \quad (1)$$

$$\rho(\sigma_i | \sigma_j) = \sum_{k=0}^{N-1} \ln[P(\sigma_{ik} | \sigma_{ik}, k)] \quad (2)$$

where $\rho(\sigma_i|\sigma_j)$ is the natural log of the probability of observing sequence $\sigma_i$ when the actual barcode sequence is $\sigma_j$, M is the number of barcodes, N is the length of each barcode sequence or a portion thereof, $\sigma_{ik}$ refers to the nucleotide at the kth position in the ith barcode sequence, and $P(\sigma i_k|\sigma_{jk}, k)$ is the $P_{error}$(obs|act, pos) error function estimated for the sequencer, as described above.

The natural log of the probability can be used in the equation (2) above in order to avoid numerical underflow in calculating the minimum $\Theta$ in equation (1) above. For example, for typical barcode lengths of N≥6, and barcode set sizes M of about 50, the number of distinct combinations of barcodes (4NM) is 4×10180, which is too large to evaluate by brute force in current systems (e.g., it would take too much time to find the minimum $\Theta$ by evaluating all 4×10180 combinations of possible sets of barcodes).

As such, in some embodiments of the present invention, a greedy technique is used to evaluate $\Theta$, as shown below: for each barcode$_0$ in set of all possible sequences of length N{

```
for each barcode₀ in set of all possible sequences of length N{
    for(i = 1;i < M;++i){
        for each barcodeᵢ in set of all possible sequences of length N{
            Evaluate Θ from Eq(1) for all barcodesⱼ; j < i
            if(Θ < Θ_best){
                Θbest = T;
                Best barcode = barcodeᵢ
            }
            Add Best barcode to the pool of barcodes
        }
        if(Θ_best < previous Θ_best){
            output set of candidate barcodes
        }
    }
}
```

Figure 7C:
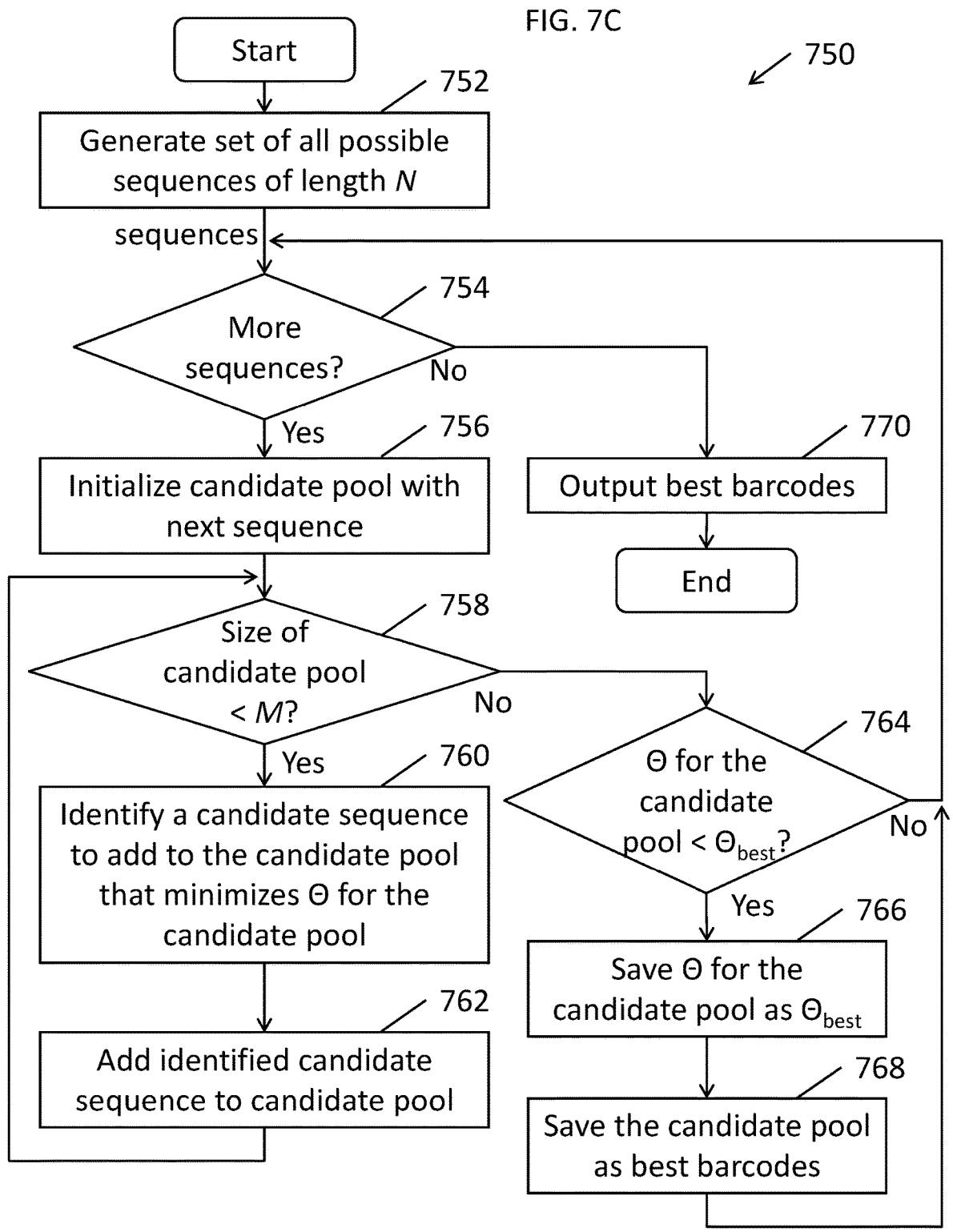
FIG. 7C is a flowchart illustrating a method according to one embodiment of the present invention for generating a set of barcode sequences customized for a sequencer based on the error probability function of the sequencer.

FIG. 7C is a flowchart illustrating a method 750 according to one embodiment of the present invention for generating a set of barcode sequences customized for a sequencer based on the error probability function of the sequencer. The flowchart corresponds to the above pseudocode description of the process.

Referring to FIG. 7C and the above pseudocode, the processor tests some or all possible starting barcode sequences barcode$_0$ of length N by adding M−1 additional barcodes to a pool of barcodes, one at a time. In operation 752, the processor generates, or iterates over, some or all possible sequences of length N (e.g., some or all $4^N$ possible combinations of A, T, G, and C). In operation 754, the processor determines if there are more sequences to consider. If so, then in operation 756 the next sequence is used to initialize a candidate pool (e.g., the next sequence is made the only member of a new collection of barcode sequences). In operation 758, the processor determines if the size of the candidate pool is less than the target size of M for the candidate pool. If so, then the processor identifies a new candidate sequence in operation 760 and adds the identified sequence to the pool in operation 762. The choice of which additional barcode to add is made by selecting a barcode that minimizes $\Theta$ for the current candidate pool of barcodes.

So, for example, the process can begin with any first selected one of the $4^N$ possible barcodes. Next, some or all possible sets of two barcodes of the $4^N$ possible barcodes, in which one of the barcodes is the first selected barcode, are generated. The error rate of each set is determined. A set with the lowest error rate or an acceptably low error rate is selected as a second barcode set. Next, some or all possible sets of three barcodes of the $4^N$ possible barcodes, in which two of the barcodes are the second set of barcodes, are generated. The error rate of each set is determined. A set with the lowest error rate or an acceptably low error rate is selected as a third barcode set. This process is repeated until a set of M barcodes with acceptably low error is identified, M representing the number of samples to be multiplexed. In some cases, M is a multiple of the number of wells in a sample plate, such as 6, 12, 24, 48, 96, 384, or 1536. In some instances, M is or is about 4, 5, 6, 7, 8, 9, 10, 11, 12, 18, 24, 36, 48, 72, 96, 120, 128, 144, 168, 192, 216, 240, 264, 288, 312, 336, 360, 384, 408, 432, 456, 480, 504, 528, 552, 576, 600, 624, 648, 672, 696, 720, 744, 768, 792, 816, 840, 864, or more. As the size of M increases, the size of N may also need to increase to allow for enough diversity between the resulting barcodes while maintaining the ability to identify sequenced barcodes with confidence. In some cases, N is or is at least 5, 6, 7, 8, 9, 10, 11, 12, 13, 14, or 15 nucleotides long. In other cases, N is less than 5, 6, 7, 8, 9, 10, 11, 12, 13, 14, or 15 nucleotides long. As the length of the barcode, or N, grows, the length of the portion of the attached analyte molecule that is detected or detected with confidence can decrease. This is because some sequencing technologies have limited read lengths. Alternatively or in addition, the accuracy of detecting a particular nucleotide decreases depending on its position in the sequence. Generally, nucleotides that are further along the read are read less accurately than nucleotides that are at the beginning of a read. As such, the length of the barcode can balance the desire to accurately discriminate between samples using longer barcodes with the desire to read as much of the analyte nucleic acid as possible or practical.

It may not be necessary to generate all possible sequences of length N to obtain a barcode set with an acceptably low error rate. The number of possible sequences of length N is $4^N$. At large numbers, it may require large amounts of computing power or unacceptably long waits to generate all possible sequences. In this case, it may suffice to generate fewer than all possible sequences, for example, for a sequence of length N, generating a least or no more than any of $4^{N-1}$, $4^{N-2}$, $4^{N-3}$, $4^{N-4}$, $4^{N-5}$, $4^{N-6}$, $4^{N-7}$, $4^{N-8}$, $4^{N-9}$, $4^{N-10}4^{N-11}$, $4^{N-12}$, $4^{N-13}$, $4^{N-14}$ or $4^{N-15}$ of the possible sequences.

An acceptably low error rate among the error rates can be, for example, less than the worst error rate, a less than average error rate, error rate in the bottom quintile, and error rate in the bottom 10%, and error rate in the bottom 5%, an error rate in the bottom 3%, an error rate in the bottom 2%, an error rate in the bottom 1%, an error rate in the bottom 0.5% or the lowest or least error rate. An acceptably low error rate among the error rates can also be, for example, an error rate that is or is predicted to be lower than 90%, 95%, 96%, 97%, 98%, 99%, or 99.5% of the expected combinations of barcode sets or tested barcode sets.

This entire process can be iterated, each iteration using a different one of the $4^N$ different nucleotide barcode sequences as the first selected barcode. Now, among the $4^N$ different sets generated, a set with acceptably low error rate, e.g. lowest error rate, can be selected as the barcode set to be used.

After adding the M−1 additional barcodes to the pool, in operation 764 the processor compares the computed Θ for the candidate pool based on the current barcode0 against the best (lowest) Θ computed so far (Θbest), and the better set of barcodes is retained as the best candidate set of barcodes. In other words, the new lowest Θ is saved as the new Θbest in operation 766, and the candidate pool corresponding to that new Θ best is saved as the best set of barcodes in operation 768. The process then returns to operation 754 to proceed with the next starting barcode sequence from some or all possible sequences. After iterating through some or all possible starting barcode sequences, there are no more sequences to consider in operation 754, and, in operation 770, the processor outputs best candidate pool (e.g., having lowest Θ) across all possible starting barcodes tested as the set of barcode sequences tailored for the sequencer.

Alternatively or in addition, the sequences can be generated in silico to increase or maximize the likelihood that the barcodes in the set can be identified with accuracy and confidence. In some of such methods, a barcode is added to the candidate pool by analyzing the barcodes already in the candidate pool and using the 4×4×N matrix to generate a barcode sequence that is unlikely to be misidentified as other barcodes in the candidate set. In some cases, the barcode generated minimizes the chance of being misidentified as another barcode in the set. The methods can take into account the likelihood that a particular position or particular nucleotides at a particular position can be more susceptible than others to be misidentified. In such methods, the use of particular nucleotides at that position can be weighted to reduce or minimize the likelihood that the nucleotide will be misread. For example, an A at a position may be more likely to be misread as a T than either a G or a C at that position. As such, the use of A and/or T nucleotides at that position might be reduced or minimized. Alternatively or in addition, the use of A or T nucleotides at that position might also be accompanied by sufficient other diversity throughout the barcode to ensure that the likelihood of the barcode being misidentified is reduced or minimized. Alternatively or in addition, the use of an A might be paired with another nucleotide at a different position such that some or all of the barcode in which an A appears at that position include the paired nucleotide at a different position in order to provide some redundancy or error checking.

In such instances, the use of such methods can also include the minimization or elimination of nucleotides that are prone to errors in certain positions. This can be done to reduce or minimize the likelihood that an individual barcode will include read errors. The methods can also include varying the use of combinations of nucleotides with higher and lower likelihoods of being identified with confidence in order to improve or maximize the ability to identify the barcodes in or across a candidate pool with confidence.

Figure 8:
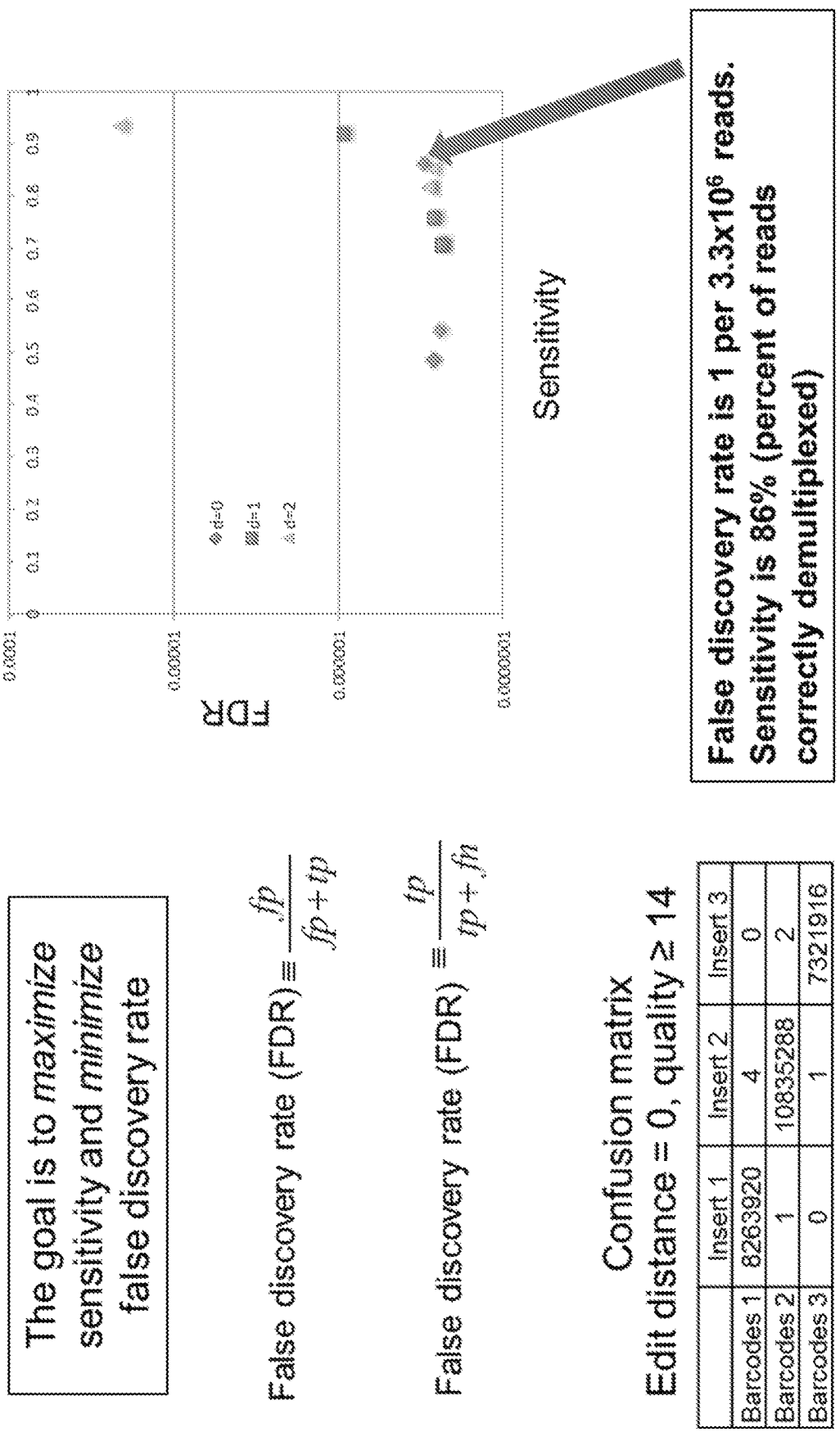
FIG. 8 depicts demultiplexing results using False Discovery Rate (FDR), according to embodiments of the present invention.

As such, embodiments of the present invention are directed to generating a set of barcodes that is optimized for the error characteristics of a particular sequencer, thereby significantly reducing the probability of cross-contamination between separate samples by improving the reliability of separating reads based on the barcodes. The optimization can be across FIG. 8 depicts demultiplexing results using False Discovery Rate (FDR), according to embodiments of the present invention. As shown in FIG. 8, through the use of customized sequences, the false discovery rate can be reduced to 1 per $3.3 \times 10^6$ reads, with a sensitivity as high as 86%. In addition, as shown in the confusion matrix in FIG. 8, the three sets of barcodes (Barcodes 1, Barcodes 2, and Barcodes 3) applied to three corresponding samples (Insert 1, Insert 2, and Insert 3) provide a high level of matching where millions of sequenced reads are correctly sorted by sample, with only single digit counts or zero incorrectly sorted sequenced reads.

Quantitation of Sample-to-Sample Cross-Talk Using Synthetic Oligonucleotides with Unique Sequences.

In some embodiments of the present invention, a method for accurate quantification of sample-to-sample cross-contamination during a laboratory process includes the use of synthetic DNA or RNA oligonucleotides (SDROs). The SDROs have unique and non-natural sequences, and are easy to distinguish from other nucleic acid sequences in samples.

A lab process may be performed in individual tubes, tube strips, multi-well plates, or any other format. Examples of a lab process include the methods disclosed in Examples 2-4. SDROs are dissolved in water or buffer, and used as external control samples (ECS). At the end of the lab process, all samples are sequenced using next generation sequencing technology, quantified with real-time PCR, or any other sensitive method. If no sample-to-sample contamination occurred, the non-ECS samples should contain no SDROs. If the sequence of the SDROs is present in the non-ECS samples, their level can be quantified, and routes of sample-to-sample contamination inferred. This method also enables one to assign confidence values to the relative abundance of the organisms found in clinical (or any complex) samples.

For example, if multiple clinical samples are to be analyzed in parallel by a sequencing technology, sample-to-sample contamination may occur at multiple steps in the process; for example: while processing the samples in the lab or sequencing the samples on the same instrument run. This occurs even when all individual samples are barcoded, due to poor laboratory practices or use of leaky barcodes. In addition, run-to-run carryover may occur on the sequencing instruments. By using SDROs as ECS samples (one or more per run), sample-to-sample contamination may be very accurately quantified.

As another example, to automate a process from one to 96 samples at a time, a liquid-handling robot is utilized. To test the level of sample-to-sample contamination, SDROs are placed at various positions on the 96 well plate. Following the laboratory process, each sample is sequenced and relative abundance of the SDROs is determined, from which the level of sample-to-sample contamination can be computed.

According to one method, levels of cross-contamination can be determined by pairing samples of different control polynucleotides with a set of barcodes such that sample control polynucleotides is barcoded with a different member of the set of barcodes. Preferably, samples containing control polynucleotides are, themselves, highly pure, having contamination levels less than one part per 10,000, one part per 100,000, or one part per 1 million. Methods of making having pure control polynucleotides can involve assembling the control polynucleotides from a set of overlapping fragments of oligonucleotides. The possibility of error using multiple oligonucleotides is the product of the contamination rate of each polynucleotide product used. The length of the control polynucleotides can be suited to the preferred length of the sequencing system used. For example, for Illumina sequencing control polynucleotides can be about 100 to 800 nucleotides in length.

In certain embodiments, barcodes are pooled in pairs such that in a barcode reaction polynucleotide there's a different barcode at each end. The barcodes can be attached in a directional manner in order to favor attaching a first barcode at a first end and a second barcode at a second end. In one example, adding the barcodes in a directional manner can include the use of single stranded molecules, such as RNA, as the analyte molecule to which the barcodes are added. In such cases, the power to demultiplex molecules from different samples can also be increased. This is because the barcodes at both ends of tagged molecules can be different among different samples. In some cases, the barcodes are selected because they independently have a high probability of being correctly identified with confidence. In other cases, the barcode pairs are selected because the pair has a high probability of being correctly identified with confidence. Optionally, a barcode at one end of an analyte nucleic acid molecule can be unique to a particular sample and a second barcode at the other end can be less than unique. In some of such instances, the second barcode can identify groups of samples. Such a barcode combination is referred to as a barcode tag. In some instances, a single barcode, used alone, can be the barcode tag.

After pairing barcode samples with control samples, the barcoded samples are pooled and sequenced. After sequencing, sequencing data can be analyzed to quantify the barcode, the number of reads containing that barcode and each control sequence. This generates an error or grid in which one expects the large quantities to be consistent with the original barcode-control sample pairing. For example, if there are 96 barcodes then, they will be paired 96 samples and a 96×96 grid will be created. The number of non-perfect pairings represents a measure of cross-contamination between samples.

This measure is useful in determining the likelihood of confidence of whether in a test, sequences bearing a certain barcode tag are actually present in the test sample for example, if a cross-contamination test shows that the sample-to-sample cross-contamination is at a certain level, e.g., 0.1%, then, in a collection of reads bearing the same barcode tag, tagged molecules having a frequency in the collection of around that level, e.g., 0.1%, or less are presumed to represent noise or cross-contamination and not actual sequence is in the original sample.

The methods can also include the detection of barcodes that should not be present in certain samples or in particular assays or lanes. For example, different barcodes or sets of barcodes can be used in different lanes during the same sequencing run. The detection of a barcode from a first set in a lane that includes a different set of barcodes can represent a measure of cross-contamination between samples. The number of samples per lane can vary depending on the number of reads the instrument can obtain and the desired read depth for each sample. In some cases, the number of samples per lane can be or can be about 1, 2, 3, 4, 5, 6, 7, 8, 9, 10, 11, 12, 24, 48, 96, 120, 128, 144, 168, 192, 216, 240, 264, 288, 312, 336, 360, 384, 408, 432, 456, 480, 504, 528, 552, 576, 600, 624, 648, 672, 696, 720, 744, 768, 792, 816, 840, 864, or more. Alternatively or in addition, the number of samples processed per sequencing run can be 1, 2, 3, 4, 5, 6, 7, 8, 9, 10, 11, 12, 24, 48, 96, 120, 128, 144, 168, 192, 216, 240, 264, 288, 312, 336, 360, 384, 408, 432, 456, 480, 504, 528, 552, 576, 600, 624, 648, 672, 696, 720, 744, 768, 792, 816, 840, 864, 960, 1056, 1152, 1248, 1344, 1440, 1536, 1632, 1728, 1824, 1920, 2840, 7680, 15360, or more.

Where it is found that cross-contamination of barcodes in a set is at unacceptable levels, adjustments can be made to the manufacturing process to reduce the cross-contamination.

Sequencing

The present methods are generally compatible with any high-throughput or next-generation sequencing systems, methods, instruments, and machines. The systems, methods, instruments, and machines described herein may have reproducible biases in the read errors they produce. As such, instrument-specific barcodes can be produced for each system, method, instrument, or machine.

In some cases, the sequencing method includes classic Sanger sequencing methods, which are well known in the art. In other cases, the sequencing method includes those performed by high-throughput systems. Some high-throughput systems allow detection of a sequenced nucleotide immediately after or upon its incorporation into a growing strand. Such systems can provide detection of sequence information in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour. In some cases, the sequencing reads are at least about 50, about 60, about 70, about 80, about 90, about 100, about 120, about 150, about 180, about 210, about 240, about 270, about 300, about 350, about 400, about 450, about 500, about 600, about 700, about 800, about 900, about 1000, about 1500, about 2000, about 2500, about 3000, about 4000, about 5000, about 6000, about 7000, about 8000, about 9000, or about 10000 bases per read.

In some embodiments, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 1000 machines. These machines use reversible terminator-based sequencing by synthesis chemistry. These machines can do 200 billion DNA reads or more in eight days. Smaller systems may be utilized for runs within 3, 2, 1 days or less time.

In some embodiments, high-throughput sequencing involves the use of technology available by ABI Solid System. This genetic analysis platform that enables massively parallel sequencing of clonally-amplified DNA fragments linked to beads. The sequencing methodology is based on sequential ligation with dye-labeled oligonucleotides.

The next generation sequencing can comprise ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high-density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an ION-PROTON™ Sequencer is used to sequence nucleic acid. In some cases, an IONPGM™ Sequencer is used. The Ion Torrent Personal Genome Machine (PGM). The PGM can do 10 million reads in two hours.

In some embodiments, high-throughput sequencing involves the use of technology available by Helicos BioSciences Corporation (Cambridge, Massachusetts) such as the Single Molecule Sequencing by Synthesis (SMSS) method. SMSS is unique because it allows for sequencing the entire human genome in up to 24 hours. Finally, SMSS is described in part in US Publication Application Nos. 20060024711; 20060024678; 20060012793; 20060012784; and 20050100932.

In some embodiments, high-throughput sequencing involves the use of technology available by 454 Lifesciences, Inc. (Branford, Connecticut) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density picolitre reactors", Nature, doi:10.1038/nature03959; and well as in US Publication Application Nos. 20020012930; 20030068629; 20030100102; 20030148344; 20040248161; 20050079510, 20050124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

The next generation sequencing technique can comprise real-time (SMRT™) technology by Pacific Biosciences. In SMRT, each of four DNA bases can be attached to one of four different fluorescent dyes. These dyes can be phospholinked. A single DNA polymerase can be immobilized with a single molecule of template single stranded DNA at the bottom of a zero-mode waveguide (ZMW). A ZMW can be a confinement structure which enables observation of incorporation of a single nucleotide by DNA polymerase against the background of fluorescent nucleotides that can rapidly diffuse in an out of the ZMW (in microseconds). It can take several milliseconds to incorporate a nucleotide into a growing strand. During this time, the fluorescent label can be excited and produce a fluorescent signal, and the fluorescent tag can be cleaved off. The ZMW can be illuminated from below. Attenuated light from an excitation beam can penetrate the lower 20-30 nm of each ZMW. A microscope with a detection limit of 20 zeptoliters (10-21 liters) can be created. The tiny detection volume can provide 1000-fold improvement in the reduction of background noise. Detection of the corresponding fluorescence of the dye can indicate which base was incorporated. The process can be repeated.

In some cases, the next generation sequencing is nanopore sequencing (See, e.g., Soni GV and Meller A. (2007) Clin Chem 53: 1996-2001). A nanopore can be a small hole, of the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridION system. A single nanopore can be inserted in a polymer membrane across the top of a microwell. Each microwell can have an electrode for individual sensing. The microwells can be fabricated into an array chip, with 100,000 or more microwells (e.g., more than 200,000, 300,000, 400,000, 500,000, 600,000, 700,000, 800,000, 900,000, or 1,000,000) per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., SiNx, or SiO2). The nanopore can be a hybrid pore (e.g., an integration of a protein pore into a solid-state membrane). The nanopore can be a nanopore with integrated sensors (e.g., tunneling electrode detectors, capacitive detectors, or graphene based nano-gap or edge state detectors (see e.g., Garaj et al. (2010) Nature vol. 67, doi: 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

The next generation sequencing can in some cases comprise DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adaptors (Adl) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., Acul), and the DNA can be cleaved by Acul 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Adl adapter. A restriction enzyme (e.g., Acul) can be applied, and the DNA can be cleaved 13 bp to the left of the Adl to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flow cell). The flow cell can be a silicon wafer coated with silicon dioxide, titanium and hexamehtyldisilazane (HMDS) and a photoresist material. Sequencing can be performed by unchained sequencing by ligating fluorescent probes to the DNA. The color of the fluorescence of an interrogated position can be visualized by a high-resolution camera. The identity of nucleotide sequences between adaptor sequences can be determined.

In some embodiments, high-throughput sequencing can take place using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication No. 20030044781 and 2006/0078937. Overall such systems involve sequencing a target nucleic acid molecule having a plurality of bases by the temporal addition of bases via a polymerization reaction that is measured on a molecule of nucleic acid, such as the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In some embodiments of the present invention, sequencing of the barcoded library DNA may be performed on any Illumina® platform.

Data Analysis

Figure 9:
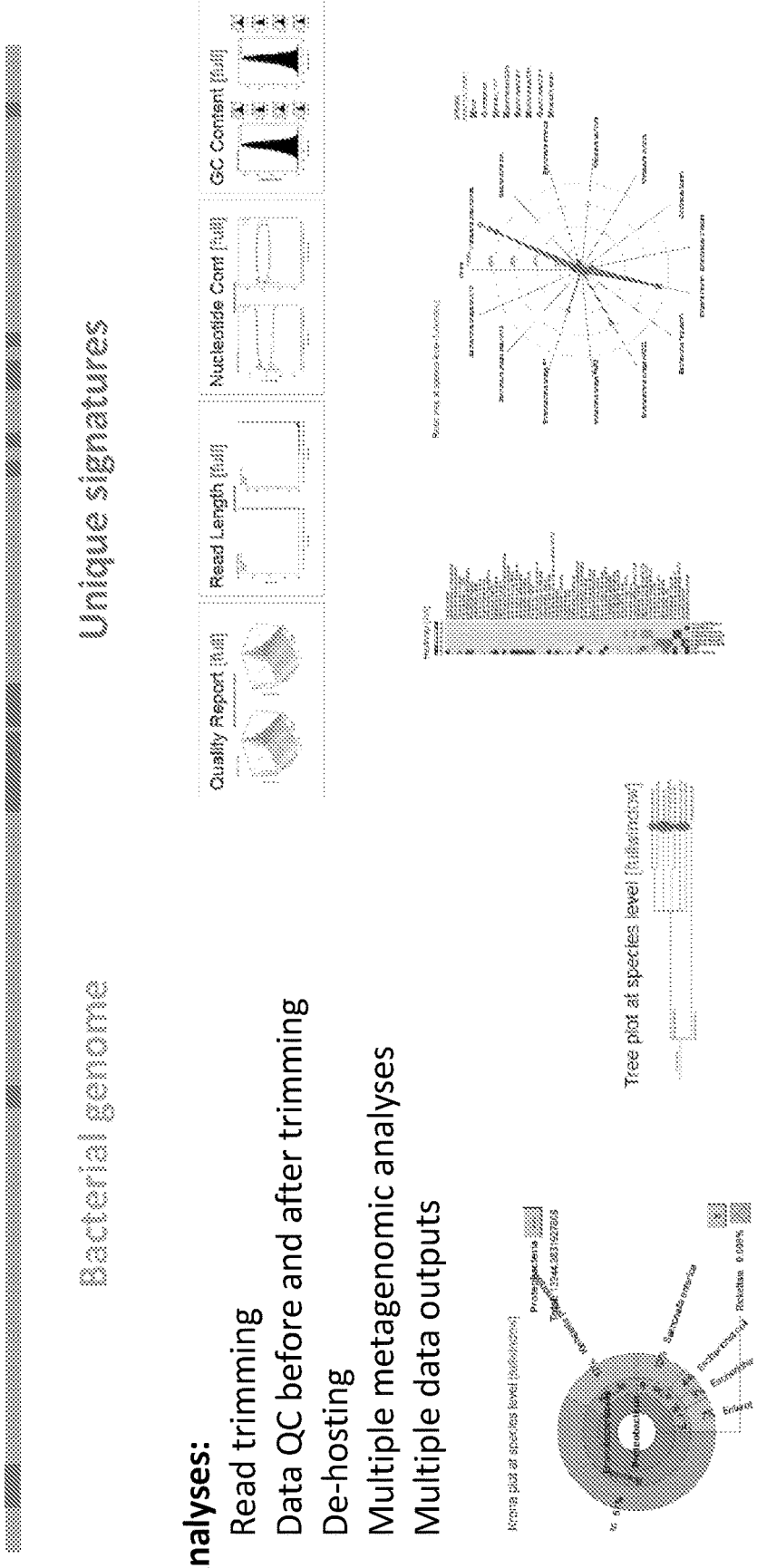
FIG. 9 outlines the data analysis according to embodiments of the present invention for identifying unique signature sequences in the analyzed sample.
Figure 10A:
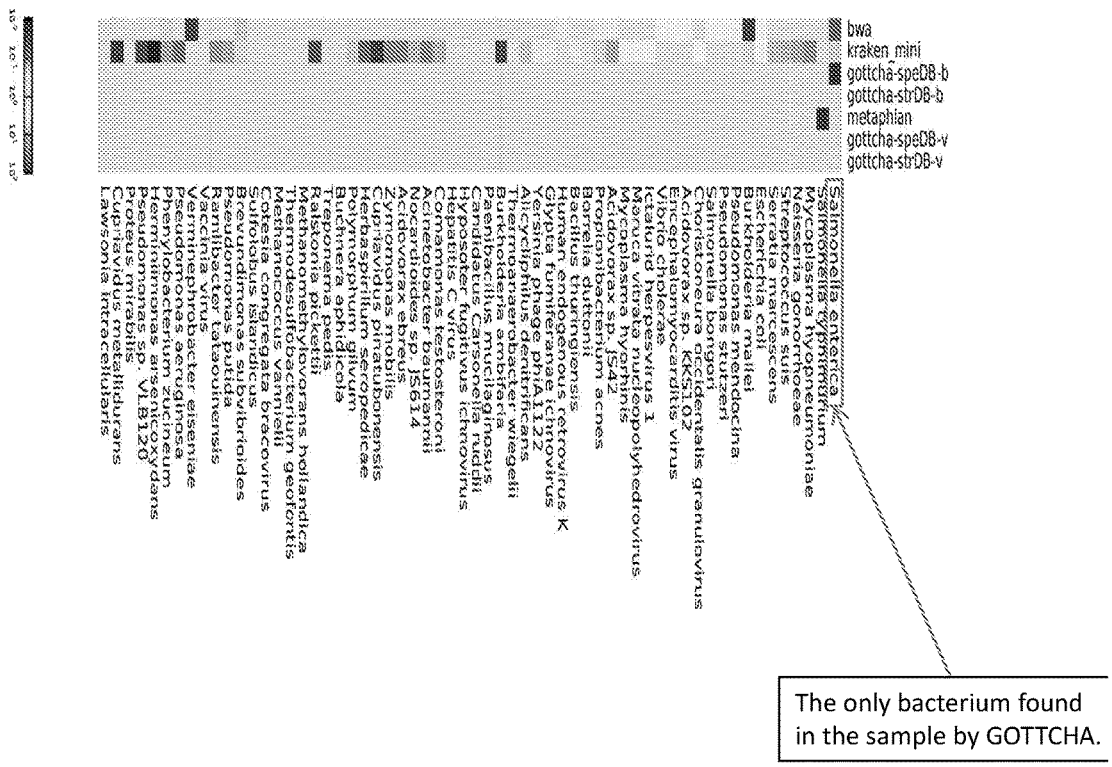
FIG. 10A shows species level classification of sequencing reads from a human blood sample spiked with *Salmonella enterica*, the sample processed according to embodiments of the present invention.
Figure 10B:
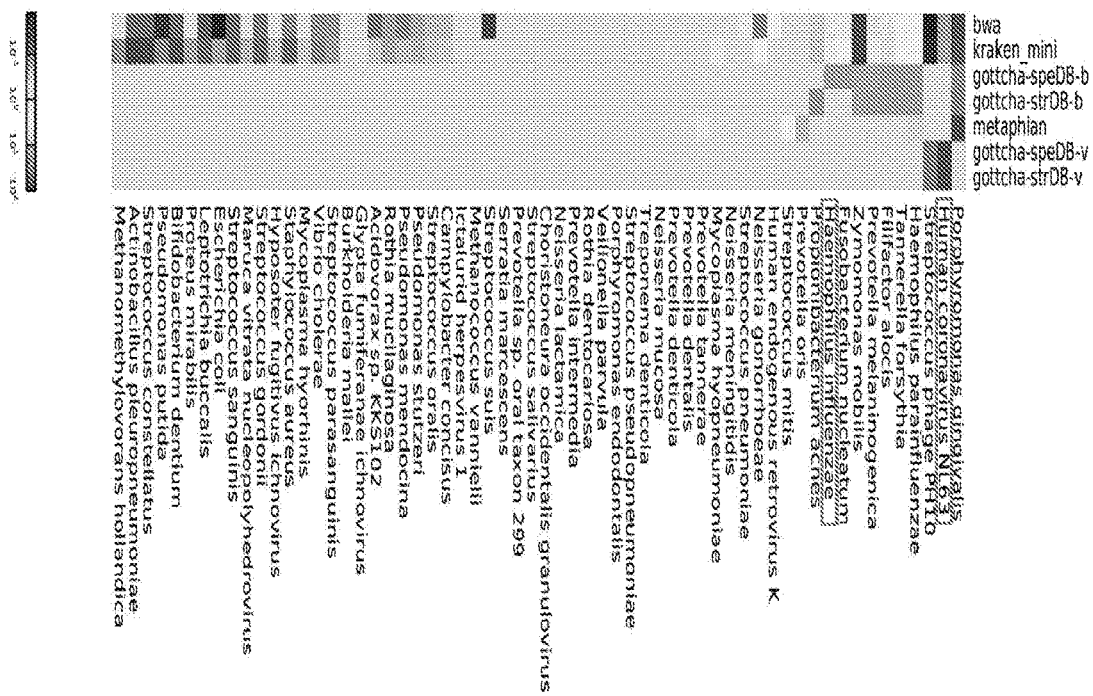
FIG. 10 B shows species level classification of sequencing reads from a respiratory sample from a human subject with an upper respiratory tract infection, the sample processed according to embodiments of the present invention.
FIG. 10C shows species level classification of sequencing reads from a human stool sample, showing symptoms consistent with *C. difficile* infection, the sample processed according to embodiments of the present invention.
FIG. 10D shows species level classification of sequencing reads from a human sputum sample processed according to embodiments of the present invention.
FIG. 10E shows species level classification of sequencing reads from a human urine sample processed according to embodiments of the present invention.
Figure 10C:
Figure 10D:
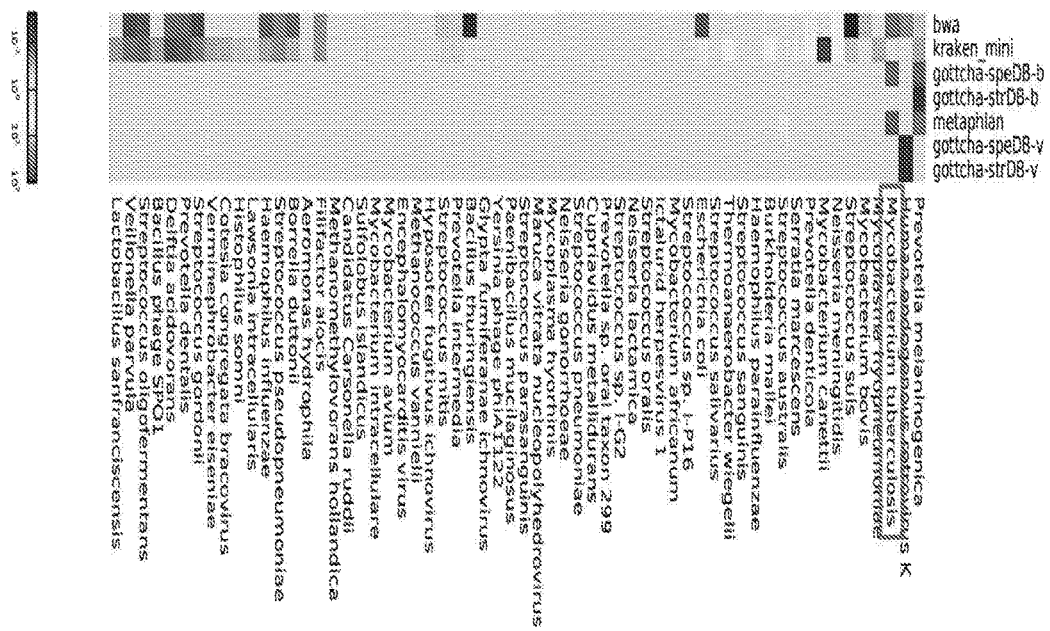
Figure 10E:
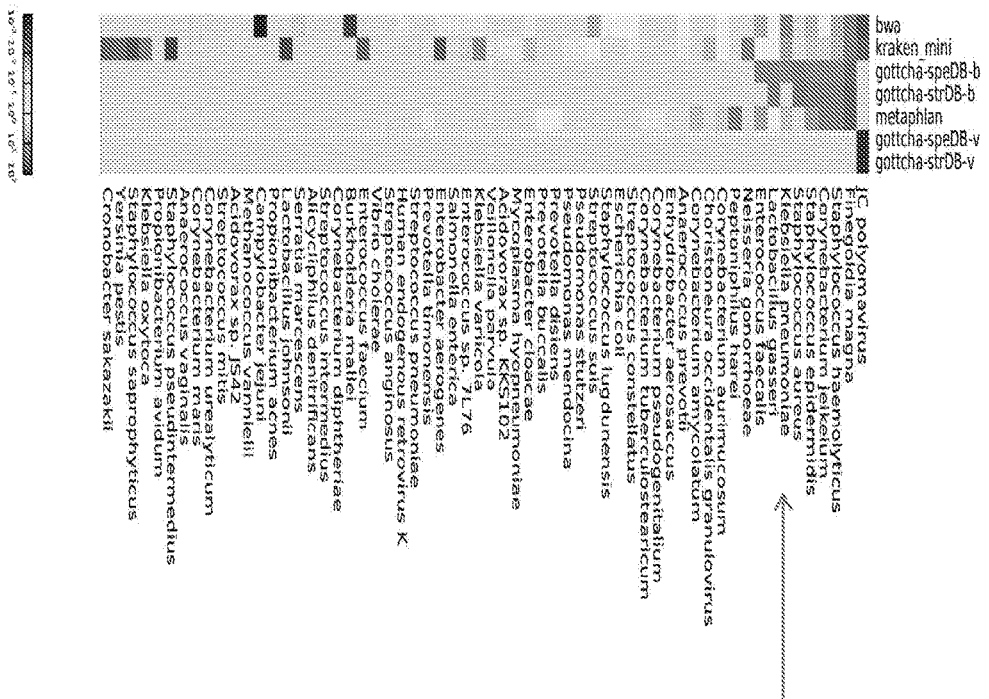

According to embodiments of the present invention, data analysis may be performed with any algorithm that can identify microorganisms, including pathogens. FIG. 9 outlines the data analysis according to embodiments of the present invention for identifying unique signature sequences in the analyzed sample. In some embodiments of the present invention, to achieve maximum sensitivity, while allowing some false positive results, BWA (Burrows-Wheeler Aligner) may be used to map the reads to RefSeq database genomes. An analysis tool called GOTTCHA (Genomic Origin Through Taxonomic CHAllenge) was also used. This GOTTCHA application runs on the Empowering the Development of Genomics Expertise (EDGE) platform. GOTTCHA is not as sensitive as BWA, but is exquisitely specific.

Species level taxonomic classification of sequencing reads are shown in FIGS. 10A-10E. Each figure is a heat map (blue—least abundant, red—most abundant) of the organisms found in the sample. The rows display the results for each read classification tool. All tools are read aligners, but differ in the database they use. BWA uses the entire RefSeq, while Kraken and Metaphlan use their own specialized databases of organisms. GOTTCHA uses databases that contain species (speDB) and strain (strDB) information for bacteria (-b) and viruses (-v). These databases are pre-computed (once a month) for faster data analysis. The columns in each figure show the organisms found in each sample.

System and Methods for Identifying Microbial Nucleic Acids in a Sample.

According to embodiments of the present invention, using the methods and techniques disclosed herein, a system for identifying microbial nucleic acids in a sample from a subject includes treating and preparing the sample, purifying the nucleic acids (RNA and/or DNA); "decluttering" or removing the non-informative RNA (RNR) of the purified nucleic acids; preparing a library of DNA fragments from the RNR-processed nucleic acids; barcoding the DNA fragments for demultiplexing sequence analysis; sequencing the barcoded DNA fragments; and analyzing the sequence data by mapping the sequences reads using BWA, Kraken, and/or Metaphlan together with the GOTTCHA analysis application using the EDGE platform.

Figure 11:
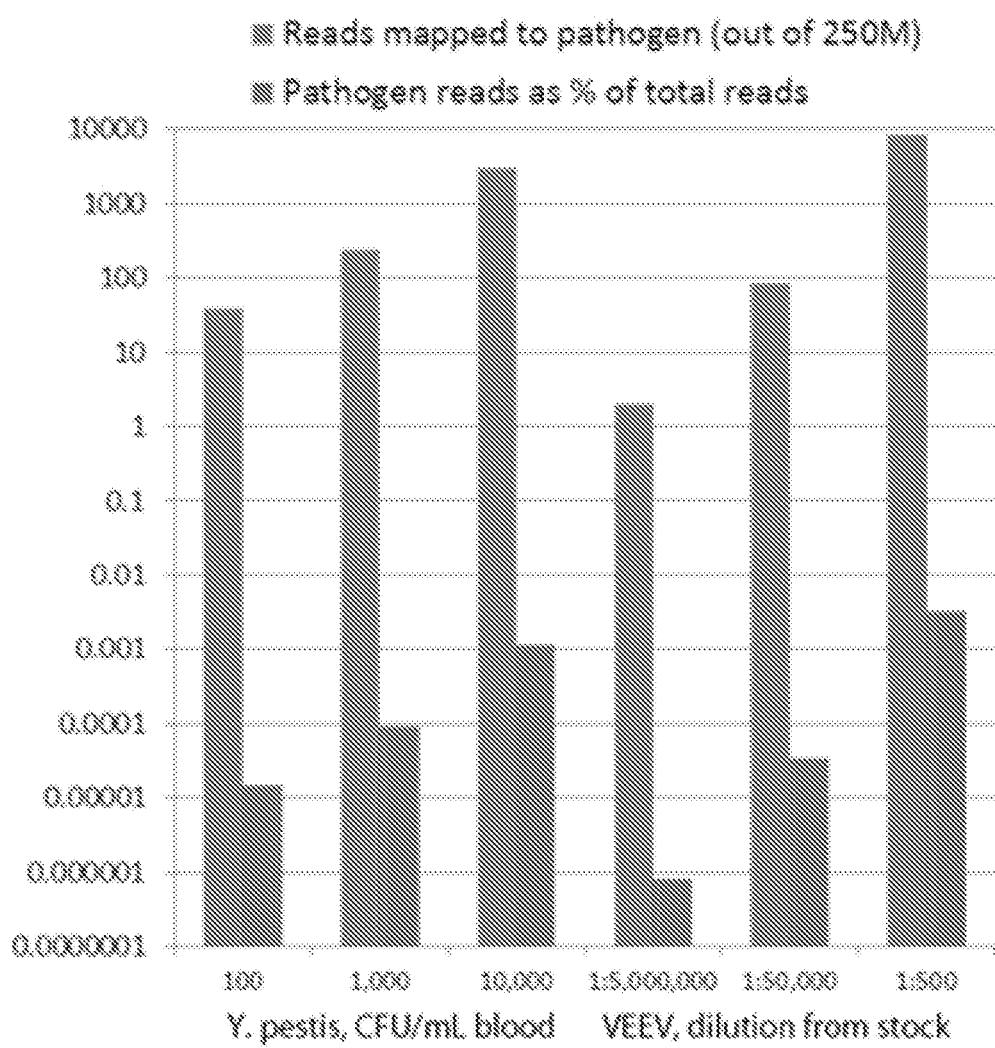
FIG. 11 is a graph of sequencing reads from RNA processed according to embodiments of the present invention from a human blood sample spiked with bacterial (*Yersinia pestis*) or viral (Venezuelan equine encephalitis virus, VEEV) pathogens as indicated at clinically relevant concentrations. Out of 250,000,000 sequencing reads obtained for each of the six samples, very few mapped to the spiked-in pathogen (blue bars), and these reads made up an extremely small percentage of total reads (red bars).

Using the system according to embodiments of the present disclosure, bacterial (*Yersinia pestis*) and viral (Venezuelan equine encephalitis virus, VEEV) pathogens were spiked into human blood at clinically relevant concentrations. As shown in FIG. 11, a graph of the sequencing reads from RNA processed from these spiked blood samples show that out of 250,000,000 sequencing reads obtained for each of the six samples, very few mapped to the spiked-in pathogen (blue bars), and these reads made up an extremely small percentage of total reads (red bars).

Figure 12:
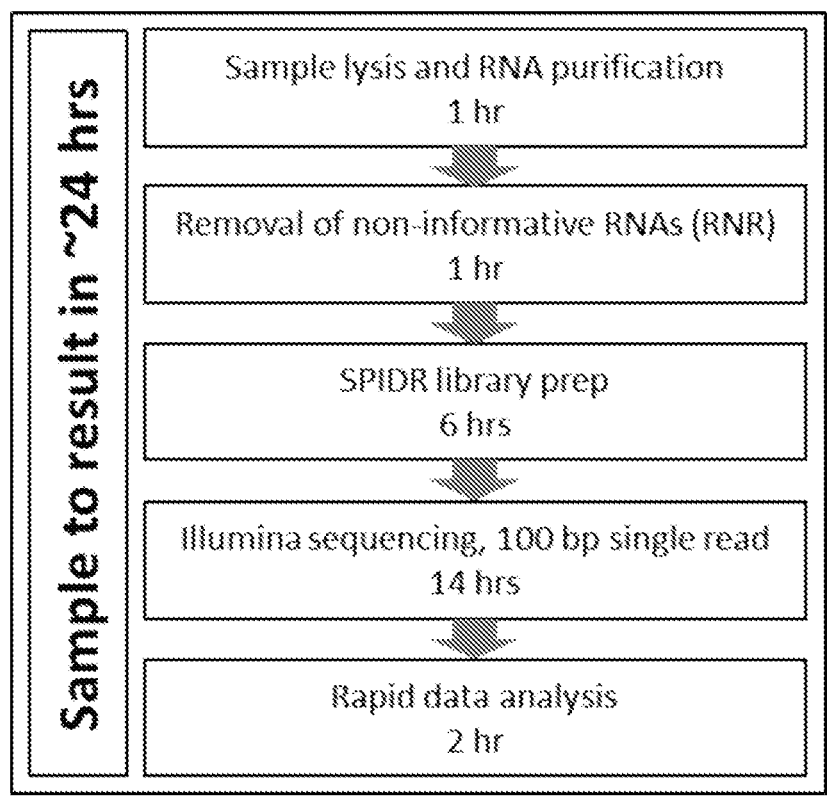
FIG. 12 is a flow chart depicting the system and approximate duration of time according to embodiments of the present invention including sample lysis and RNA purification, removal of non-informative RNA (RNR), library preparation with barcoding, sequencing using an Illumina sequencer, and data analysis of the sequencing reads.
Figure 13:
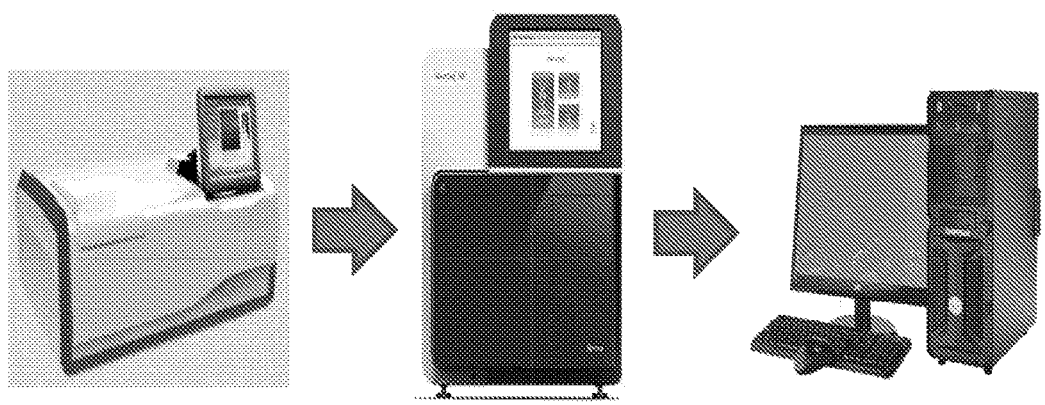
FIG. 13 depicts advantages of the compositions, methods, and systems according to embodiments of the present invention.

A flow chart depicting the system according to embodiments of the present invention and approximate duration of time for the system process is shown in FIG. 12, including sample lysis and RNA purification, removal of non-informative RNA (RNR), library preparation with barcoding, sequencing using an Illumina® sequencer, and data analysis of the sequencing reads.

Applications of the System According to Embodiments of the Present Invention.

Advantages of the compositions, methods, and systems according to embodiments of the present invention include, without limitation, detection of emerging animal and zoonotic diseases, bio-surveillance (wild animals, insects, and environment); screening of blood banks (includes emerging pathogens); food safety; identification of unknown substances; bioforensics; study of host-pathogen interactions; the ability to sequence pathogens directly in vectors without culturing; improve vaccine development (e.g., cheaper, better, faster); gut microbiome analysis; and identification of predictive biomarkers (e.g., disease severity and outcome).

Nucleic Acid Quantification

The methods, compositions and systems described herein can also be used to quantify a characteristic in a heterogeneous sample. In one aspect, provided herein are methods for quantifying nucleic acids in a sample. In another aspect, provided herein are method for quantifying microorganisms in a sample. Alternatively or in addition, provided herein are methods for quantifying a particular biochemical activity associated with a heterogeneous microbial sample or a microorganism contained therein.

Quantification of abundance can be done by computer by summing up the non-overlapping length of profiles found for a particular sequence (Linear Length or L), then determining the read coverage across that sequence (Linear Depth of Coverage or DOC).

Normalizing over the sum of all DOCs for a specific length of sequence allows one to arrive at the relative abundance (RA) of that nucleic acid in the sample. In one embodiment, normalization comprises: determining the number of base pairs contained in a particular sequence, such as an open reading frame (ORF), determining an average depth of coverage for the entire length of the sequence using the number nucleotides contained in sequence reads corresponding to the sequence and the length of the sequence, and determining the proportion of all sequence reads that correspond to the sequence.

The output of this process can be a report that indicates for a subject sample the quantities or relative amounts of nucleic acids in the sample. The report can also indicate quantitative information about the sample this can include, for example, the relative amounts of different microorganisms in the sample. It can also indicate relative activity of microorganisms in the sample based on relative gene expression. This can include, for example, types of genes that are either expressed in high amounts or alternatively, in low amounts. Alternatively or in addition, the report can indicate the identity and relative amounts of biochemical activities in the sample. The report can indicate changes as to biochemical activity in the sample over time, such as during a time course. The report can indicate differences between samples, including samples collected from the same source at different times. The source can be a subject, such as a human subject.

Reports can sometimes be output to paper, a screen, or a database. Reports can also be stored for later analysis or viewing. Reports can be sent to third parties, such as subjects, healthcare professionals, customers, collaborators, etc.

Samples

The methods described herein can be used to assess heterogeneous microbial populations. Typically, the heterogeneous microbial populations are assessed as a sample. Exemplary samples include samples from a subject, a plant, soil, a water source, an air filter, a surface, a container, a food, and other samples capable of containing or harboring heterogeneous microbial samples.

Computer Systems

The methods described herein may be used in the context of a computer system or as part of software or computer-executable instructions that are stored in a computer-readable storage medium.

In some embodiments, a system (e.g., a computer system) may be used to implement certain features of some of the embodiments of the invention. For example, in certain embodiments, a system (e.g., a computer system) for large scale metagenomic analysis of heterogeneous microbial populations in a sample is provided. The analysis performed by the system may be used in accordance with the features of the embodiments described above.

In certain embodiments, the system may include one or more memory and/or storage devices. The memory and storage devices may be one or more computer-readable storage media that may store computer-executable instructions that implement at least portions of the various embodiments of the invention. In one embodiment, the system may include a computer-readable storage medium which stores computer-executable instructions that include, but are not limited to, one or both of the following: instructions for generating a database comprising sequence signatures for at least one organism from at least one taxon; instructions for analyzing sequence reads obtained from a sample for sequence signatures informative of taxonomic information; and instructions for analyzing sequence reads obtained from a sample for determining the presence of a biochemical activity present in the sample. Such instructions may be carried out in accordance with the methods described in the embodiments above.

In certain embodiments, the system may include a processor configured to perform one or more steps including, but not limited to, (i) receiving at least one input file or accessing at least one database and (ii) executing the computer-executable instructions stored in the computer-readable storage medium. The set of input files may include, but is not limited to, a file that includes a set of reads generated by sequencing nucleic acids from a sample comprising a heterogeneous population of microbes. The steps may be performed in accordance with the methods described in the embodiments above.

The computer system may be a server computer, a client computer, a personal computer (PC), a user device, a tablet PC, a laptop computer, a personal digital assistant (PDA), a cellular telephone, an iPhone, an iPad, a Blackberry, a processor, a telephone, a web appliance, a network router, switch or bridge, a console, a hand-held console, a (hand-held) gaming device, a music player, any portable, mobile, hand-held device, wearable device, or any machine capable of executing a set of instructions, sequential or otherwise, that specify actions to be taken by that machine.

The computing system may include one or more central processing units ("processors"), memory, input/output devices, e.g. keyboard and pointing devices, touch devices, display devices, storage devices, e.g. disk drives, and network adapters, e.g. network interfaces, that are connected to an interconnect.

According to some aspects, the interconnect is an abstraction that represents any one or more separate physical buses, point-to-point connections, or both, connected by appropriate bridges, adapters, or controllers. The interconnect, therefore, may include, for example a system bus, a peripheral component interconnect (PCI) bus or PCI-Express bus, a HyperTransport or industry standard architecture (ISA) bus, a small computer system interface (SCSI) bus, a universal serial bus (USB), IIC (12C) bus, or an Institute of Electrical and Electronics Engineers (IEEE) standard 1394 bus, also referred to as Firewire.

In addition, data structures and message structures may be stored or transmitted via a data transmission medium, e.g. a signal on a communications link. Various communications links may be used, e.g. the Internet, a local area network, a wide area network, or a point-to-point dial-up connection. Thus, computer readable media can include computer-readable storage media, e.g. non-transitory media, and computer-readable transmission media.

The instructions stored in memory can be implemented as software and/or firmware to program one or more processors to carry out the actions described above. In some embodiments of the invention, such software or firmware may be initially provided to the processing system by downloading it from a remote system through the computing system, e.g. via the network adapter.

The various embodiments of the disclosure introduced herein can be implemented by, for example, programmable circuitry, e.g. one or more microprocessors, programmed with software and/or firmware, entirely in special-purpose hardwired, e.g. non-programmable, circuitry, or in a combination of such forms. Special purpose hardwired circuitry may be in the form of, for example, one or more ASICs, PLDs, FPGAs, etc.

Some portions of the detailed description may be presented in terms of algorithms, which may be symbolic representations of operations on data bits within a computer memory. These algorithmic descriptions and representations are those methods used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Figure 14:
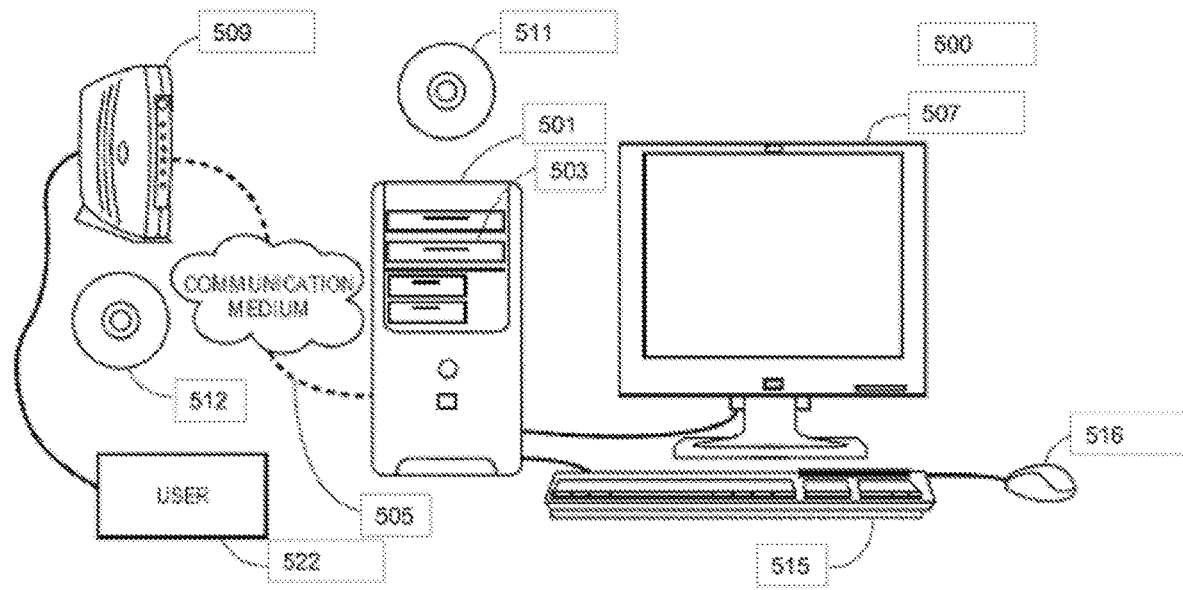
FIG. 14 illustrates various components of an exemplary computer system that can be programmed or configured to implement the methods provided herein.

Exemplary systems are provided herein. The computer system 500 illustrated in FIG. 14 may be understood as a logical apparatus that can read instructions from media 511 and/or a network port 505, which is optionally connected to server 509 having fixed media 512. In some cases, the system, such as shown in FIG. 14 includes a CPU 501, disk drives 503, optional input devices such as keyboard 515 and/or mouse 516 and optional monitor 507. In certain cases, data communication is achieved through the indicated communication medium to a server at a local or a remote location. In further cases, the communication medium includes any means of transmitting and/or receiving data. In some cases, the communication medium is a network connection, a wireless connection or an internet connection. In certain examples, such a connection provides for communication over the World Wide Web. It is envisioned that data relating to the present disclosure can be transmitted over such networks or connections for reception and/or review by a party 522 as illustrated in FIG. 14.

Figure 15:
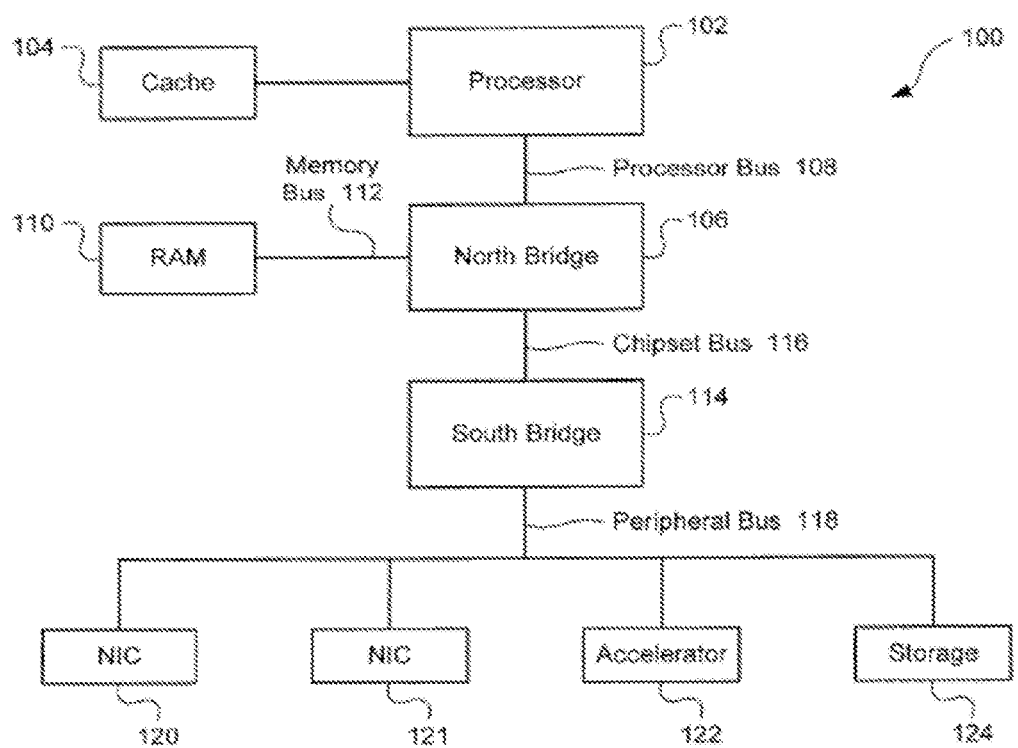
FIG. 15 is a block diagram illustrating the architecture of an exemplary computer system that can be programmed or configured to implement the methods provided herein.

FIG. 15 is a block diagram illustrating a first example architecture of a computer system 100 that can be used in connection with example embodiments of the present disclosure. In certain cases, as depicted in FIG. 15, the example computer system includes a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores are used, whether in a single computer system, in a cluster, or distributed across systems over a network comprising a plurality of computers, cell phones, and/or personal data assistant devices.

In various cases, as illustrated in FIG. 15, a high speed cache 104 is connected to, or incorporated in, the processor 102 to provide a high speed memory for instructions or data that have been used recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 includes an accelerator card 122 attached to the peripheral bus 118. In some cases, the accelerator includes field programmable gate arrays (FPGAs) or other hardware for accelerating certain processing. In further examples, an accelerator is used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, (OS™, Android™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 16:
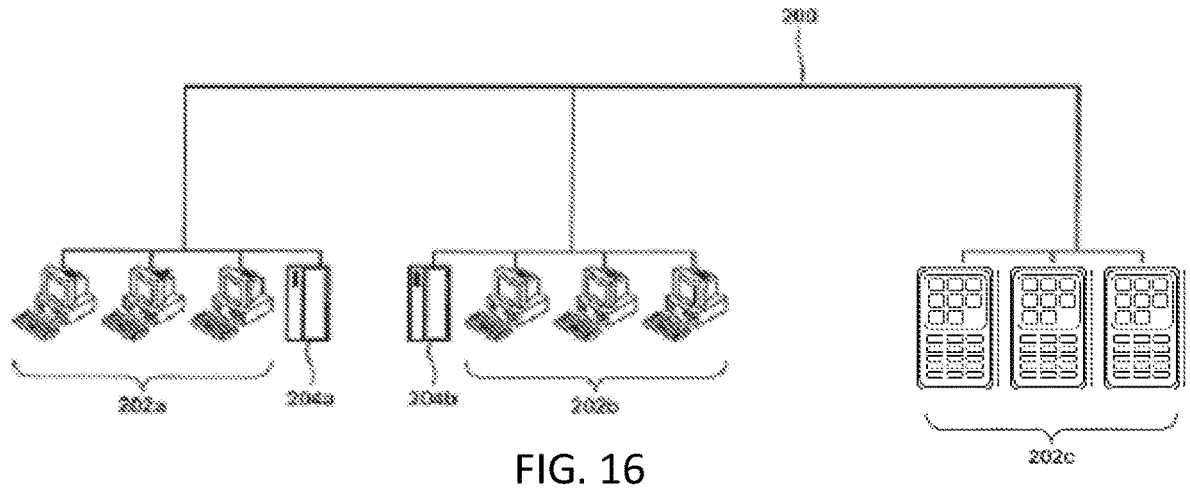
FIG. 16 is a diagram illustrating an exemplary computer network that can be configured to implement the methods provided herein.

FIG. 16 is a diagram showing a network 200 with a plurality of computer systems 202a, and 202b, a plurality of cell phones and personal data assistants 202c, and Network Attached Storage (NAS) 204a, and 204b. In certain examples, systems 202a, 202b, and 202c manage data storage and optimize data access for data stored in Network Attached Storage (NAS) 204a and 204b. In some cases, a mathematical model is used for the data and evaluated using distributed parallel processing across computer systems 202a, and 202b, and cell phone and personal data assistant systems 202c. In certain cases, computer systems 202a, and 202b, and cell phone and personal data assistant systems 202c also provide parallel processing for adaptive data restructuring of the data stored in Network Attached Storage (NAS) 204a and 204b. FIG. 16 illustrates an example only, and a wide variety of other computer architectures and systems are used in conjunction with the various embodiments of the present disclosure. In some cases, a blade server is used to provide parallel processing. In further examples, processor blades are connected through a back plane to provide parallel processing. In certain examples, storage is connected to the back plane or as Network Attached Storage (NAS) through a separate network interface.

In some cases, processors maintain separate memory spaces and transmit data through network interfaces, back plane or other connectors for parallel processing by other processors. In other embodiments, some or all of the processors use a shared virtual address memory space.

Figure 17:
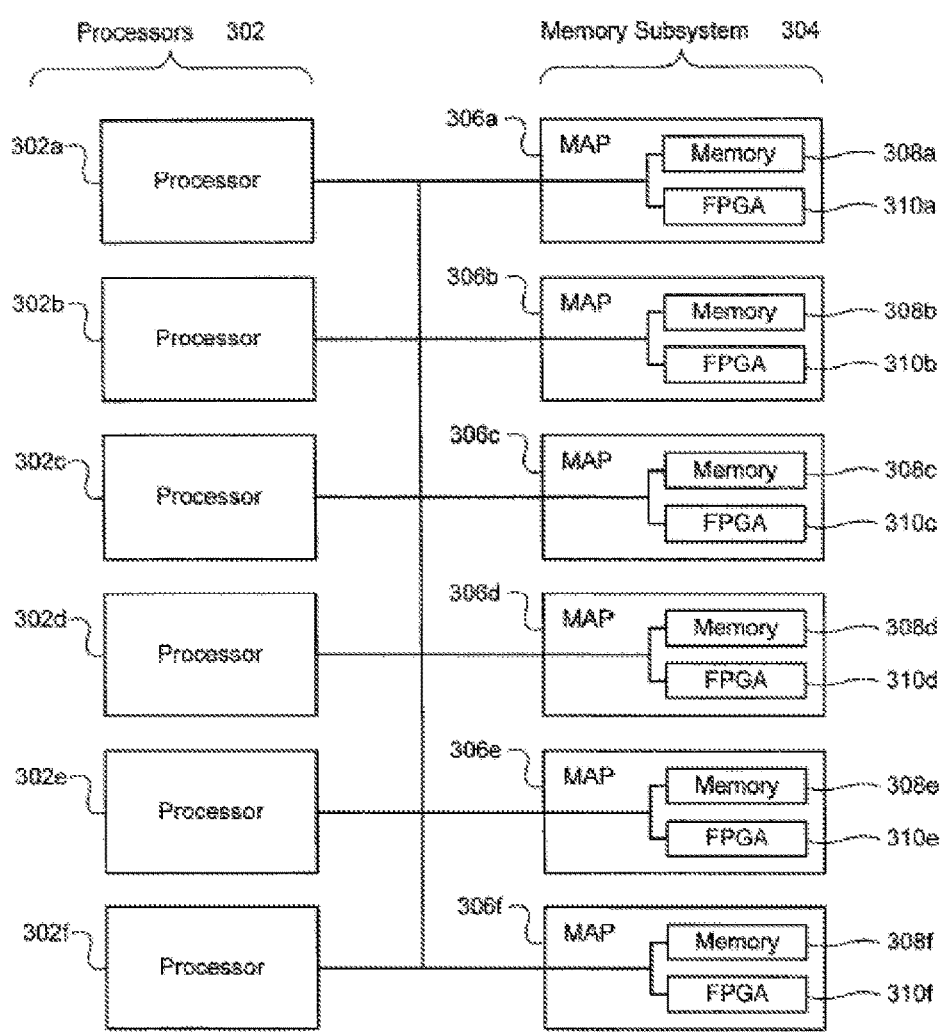
FIG. 17 is a block diagram illustrating the architecture of another exemplary computer system that can be programmed or configured to implement the methods provided herein.

FIG. 17 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. In some cases, each MAP 306a-f comprises a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. In some cases, the MAPs are used to evaluate algebraic expressions regarding the data model and to perform adaptive data restructuring in example embodiments. In this example, each MAP is globally accessible by all of the processors for these purposes. In one configuration, each MAP uses Direct Memory Access (DMA) to access an associated memory 308a-f, allowing it to execute tasks independently of, and asynchronously from, the respective microprocessor 302a-f. In this configuration, a MAP feeds results directly to another MAP for pipelining and parallel execution of algorithms.

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the platforms, systems, media, and methods disclosed herein include one or more databases, or use of the same. In view of the disclosure provided herein, those of skill in the art will recognize that many databases are suitable for storage and retrieval of sequencing, sequence signature, genomic, and taxonomic information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

The above computer architectures and systems are examples only, and a wide variety of other computer, cell phone, and personal data assistant architectures and systems can be used in connection with exemplary embodiments, including systems using any combination of general processors, co-processors, FPGAs and other programmable logic devices, system on chips (SOCs), application specific integrated circuits (ASICs), and other processing and logic elements. In some embodiments, all or part of the computer system is implemented in software or hardware. In certain cases, any variety of data storage media is used in connection with example embodiments, including random access memory, hard drives, flash memory, tape drives, disk arrays, Network Attached Storage (NAS) and other local or distributed data storage devices and systems.

In some cases, the computer system is implemented using software or hardware modules executing on any of the above or other computer architectures and systems. In other embodiments, the functions of the system are implemented partially or completely in firmware, programmable logic devices such as field programmable gate arrays (FPGAs) as referenced in FIG. 17, system on chips (SOCs), application specific integrated circuits (ASICs), or other processing and logic elements. In some cases, the Set Processor and Optimizer is implemented with hardware acceleration through the use of a hardware accelerator card, such as accelerator card 122 illustrated in FIG. 15.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

The RNA includes, but is not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs (miRNAs), siRNAs, piRNAs and long nc RNAs.

The nucleic acid molecules are often contained within at least one biological cell. Alternately, the nucleic acid molecules are contained within a noncellular biological entity, such as, for example, a virus or viral particle. Nucleic acid molecules are often constituents of a lysate of a biological cell or entity. Nucleic acid molecules are often profiled within a single biological cell or a single biological entity. Alternately, nucleic acid molecules are profiled in a lysate obtained from a single biological cell or a single biological entity. The source of nucleic acid for use in the methods and compositions described herein are often a sample comprising the nucleic acid.

As used herein, the term "about" a number refers to a range spanning that number plus or minus 10% of that number. The term "about" a range refers to that range minus 10% of its lowest value and plus 10% of its greatest value.

As used here, the terms "comprise," "comprises," "comprising," "include," "includes," and "including" are interchangeable and not intended to be limiting, and refer to the nonexclusive presence of the recited element, leaving open the possibility that additional elements are present.

As used herein, the term "comparable to" a number refers to that number plus or minus 50% of that number. The term "comparable to" a range refers to that range minus 50% of its lowest value and plus 50% of its greatest value.

As used herein, the term "subject", refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

As used herein, "obtaining" a nucleic acid sample is given a broad meaning in some cases, such that it refers to receiving an isolated nucleic acid sample, as well as receiving a raw human or environmental sample, for example, and isolating nucleic acids therefrom.

Exemplary Embodiments

1. A method of analyzing nucleic acids in a plurality of samples, the method comprising:
purifying nucleic acids from a plurality of samples;
attaching instrument-specific barcode oligonucleotides to the nucleic acids to form a barcoded library of nucleic acid, wherein nucleic acids in a sample receive instrument-specific barcode oligonucleotides sharing a common sequence and wherein different samples receive instrument-specific barcode oligonucleotide with different sequences;
sequencing the barcoded library of nucleic acids with the instrument to obtain sequence data; and
analyzing the sequence data and assigning sequences to samples according to the common instrument-specific barcode sequences.

2. The method of embodiment 1, wherein analyzing the sequence data further comprises using at least one algorithm or database for microorganisms genomic classification to identify and/or quantify and/or characterize microbes in the sample.

3. The method of embodiment 1 or embodiment 2, wherein the sample from a subject is selected from stool, blood, throat swab, nasopharyngeal swab, sputum, cerebral spinal fluid, serum, plasma, and/or urine.

4. The method of any one of embodiments 1-3, wherein attaching instrument-specific barcode oligonucleotides to the nucleic acids further comprises fragmenting the nucleic acids.

5. The method of any one of embodiments 1-4, further comprising removing non-informative RNA (RNR) from the purified nucleic acids using a sample-specific set of oligonucleotides to form RNR-processed nucleic acids.

6. The method of embodiment 5, wherein non-informative RNA comprises at least one of ribosomal RNA and transfer RNA.

7. The method of any one of embodiments 5-6, wherein removing the non-informative RNA comprises removing mRNA species that account for at least 50%, at least 75%, at least 90%, at least 95%, or at least 99% of mRNA in the sample.

8. The method of any one of embodiments 1-7, further comprising quantifying sample-to-sample contamination.

9. The method of embodiment 8, wherein quantifying sample to sample contamination comprises using synthetic DNA or RNA oligonucleotides (SDROs).

10. A method of analyzing nucleic acids in one or more samples from one or more subjects, the method comprising:
   purifying nucleic acids from a sample;
   removing non-informative RNA (RNR) from the purified nucleic acids using a sample-specific set of oligonucleotides to form RNR-processed nucleic acids;
   preparing a library of nucleic acid fragments from the RNR-processed nucleic acids;
   attaching sequence instrument-specific barcode oligonucleotides to the nucleic acid fragments in the library to form a barcoded library of nucleic acid fragments;
   sequencing the barcoded library of nucleic acid fragments to obtain sequence data; and
   analyzing the sequence data using at least one algorithm or database for microorganisms genomic classification to identify and/or quantify and/or characterize microbes in the sample.

11. The method of embodiment 10, wherein the sample from a subject is selected from stool, blood, throat swab, nasopharyngeal swab, sputum, cerebral spinal fluid, serum, plasma, and/or urine.

12. The method of embodiment 10, wherein preparing the library of nucleic acid fragments and attaching barcode oligonucleotides to the nucleic acid fragments comprises one amplification reaction.

13. The method of embodiment 10, wherein the subject is a human.

14. The method of embodiment 10, wherein non-informative RNA includes ribosomal RNA and/or transfer RNA.

15. The method of embodiment 10, wherein removing the non-informative RNA comprises removing mRNA species that account for at least 50%, at least 75%, at least 90%, at least 95%, or at least 99% of mRNA species in the sample.

16. The method of embodiment 10, comprising analyzing a plurality of samples, wherein each different sample is provided with a different sequence instrument-specific nucleotide barcode sequence.

17. The method of embodiment 16, further comprising quantifying sample-to-sample contamination.

18. The method of embodiment 17, wherein quantifying sample to sample contamination comprises using synthetic DNA or RNA oligonucleotides (SDROs).

19. A method for generating a plurality of barcodes comprising:
   generating, by a processor, a set of possible sequences of length N;
   selecting a first barcode sequence from the set of possible sequences;
   adding the first barcode sequence to a barcode candidate pool;
   identifying a second barcode sequence in the set of possible sequences, wherein, upon sequencing a nucleic acid molecule comprising the second sequence, the second sequence has a reduced likelihood of being incorrectly identified as a different barcode in the barcode candidate pool compared to a threshold value;
   adding the second sequence to the barcode candidate pool; and
   synthesizing an oligonucleotide library comprising barcodes in the barcode candidate pool.

20. The method of embodiment 19, wherein the set comprises at least 4N-15, 4N-14, 4N-13, 4N-12, 4N-11, 4N-10, 4N-9, 4N-8, 4N-7, 4N-6, 4N-5, 4N-3, 4N-2, 4N-1, or 4N sequences.

21. The method of embodiment 19, further comprising, prior to step (f):
   (i) identifying an additional barcode sequence in the set of possible sequences, wherein, upon sequencing a nucleic acid molecule comprising the additional sequence, the additional sequence has a reduced likelihood of being incorrectly identified as a different barcode in the barcode candidate pool compared to the threshold value;
   (ii) adding the additional sequence to the barcode candidate pool; and
   (iii) repeating steps (i) and (ii) until the barcode candidate pool comprises M sequences, wherein M is at least five, at least 10, at least 20, at least 40, at least 50, at least 75, or at least 100.

22. The method of any one of embodiments 19-21, wherein the threshold value is an error tolerance rate, wherein sequence reads of the barcode candidate pool comprising a single error are still correctly identified as a corresponding barcode in the barcode candidate pool.

23. The method of any one of embodiments 19-21, wherein the threshold value is an error tolerance rate, wherein sequence reads of the barcode candidate pool comprising two errors are still correctly identified as a corresponding barcode in the barcode candidate pool.

24. The method of embodiment 22 or embodiment 23, wherein the error is a mutation in a template molecule.

25. The method of embodiment 22 or embodiment 23, wherein the error is a mutation introduced during an amplification step prior to sequencing the molecule.

26. The method of embodiment 22 or embodiment 23, wherein the error is a read error made by a sequencer.

27. The method of any one of embodiments 19-22, wherein the threshold value is the average likelihood of barcode sequences in the set of possible sequences being incorrectly identified as a different barcode in the barcode candidate pool.

28. The method of any one of embodiments 19-27, wherein the threshold value is at least 2× lower than the average likelihood of barcode sequences in the set of possible sequences being incorrectly identified as a different barcode in the barcode candidate pool.

29. The method of any one of embodiments 19-28, wherein the threshold value is the lowest likelihood of barcode sequences in the set of possible sequences being incorrectly identified as a different barcode in the barcode candidate pool.

30. The method of any one of embodiments 19-29, wherein (f) is computed in accordance with an error model associated with the sequencer.

31. The method of embodiment 30, wherein the error model associated with the sequencer is determined by sequencing a plurality of training barcode sequences of length N using the sequencer to generate a plurality of sequenced reads; and
   for each position in the training barcode sequences of length N,
   counting the number of times each nucleic acid base (A, T, G, C) is observed at a particular position in the plurality of sequence reads; and
   generating an error model associated with the sequencer by calculating the probability that a nucleotide observed at a position in a sequence read is accurate.

32. The method of embodiment 31, wherein the error model calculates the probability that a pair of nucleotides observed at a pair of positions in a sequence read are accurate.

33. The method of embodiment 31, wherein the error model comprises an objective function $$\Theta = \sum_{i=0}^{M-1} \sum_{j=i+1}^{M-1} \rho(\sigma_i | \sigma_j),$$

wherein $$\rho(\sigma_i | \sigma_j) = \sum_{k=0}^{N-1} \ln[P(\sigma_{ik} | \sigma_{ik}, k)],$$

and
  wherein $\rho(\sigma_i|\sigma_j)$ is the natural log of the probability of observing sequence $\sigma_i$ when the actual barcode sequence supplied to the sequencer is $\sigma_j$, M is the number of barcodes, $\sigma_{ik}$ refers to the nucleotide at the kth position in the ith barcode sequence, and $P(\sigma_{ik}|\sigma_{jk}, k)$ is the error model associated with the sequencer.

34. A method for generating a plurality of barcodes comprising:
  (a) generating, by a processor, a set of possible sequences of length N;
  (b) selecting a first barcode sequence from the set of possible sequences;
  (c) adding the first barcode sequence to a barcode candidate pool;
  (d) adding an additional barcode sequence from the set of barcode sequences to the candidate pool, wherein the candidate pool comprising the additional barcode sequence has been identified as having a reduced likelihood that, upon sequencing nucleic acid molecules comprising barcode sequences from the candidate pool, a first member of the barcode candidate pool will be incorrectly identified as a different barcode in the barcode candidate pool compared to the addition of other barcode sequences remaining in the set of possible sequences;
  (e) repeating step j until the barcode candidate pool comprises a target number of barcodes M; and
  (f) synthesizing an oligonucleotide library comprising barcodes in the barcode candidate pool.

35. The method of embodiment 34, wherein M is at least five, at least 10, at least 20, at least 40, at least 50, at least 75, or at least 100.

36. The method of any one of embodiments 34-35, wherein (d) is computed in accordance with an error model associated with the sequencer.

37. The method of embodiment 36, wherein the error model associated with the sequencer is determined by sequencing a plurality of training barcode sequences of length N using the sequencer to generate a plurality of sequenced reads; and
  for each position in the training barcode sequences of length N,
  counting the number of times each nucleic acid base (A, T, G, C) is observed at a particular position in the plurality of sequence reads; and
  generating an error model associated with the sequencer by calculating the probability that a nucleotide observed at a position in a sequence read is accurate.

38. The method of embodiment 37, wherein the error model calculates the probability that a pair of nucleotides observed at a pair of positions in a sequence read are accurate.

39. The method of embodiment 37, wherein the error model comprises an objective function $$\Theta = \sum_{i=0}^{M-1} \sum_{j=i+1}^{M-1} \rho(\sigma_i | \sigma_j),$$

wherein $$\rho(\sigma_i | \sigma_j) = \sum_{k=0}^{N-1} \ln[P(\sigma_{ik} | \sigma_{ik}, k)],$$

and
  wherein $\rho(\sigma_i|\sigma_j)$ is the natural log of the probability of observing sequence $\sigma_i$ when the actual barcode sequence supplied to the sequencer is $\sigma_j$, M is the number of barcodes, $\sigma_{ik}$ refers to the nucleotide at the kth position in the ith barcode sequence, and $P(\sigma_{ik}|\sigma_{jk}, k)$ is the error model associated with the sequencer.

40. A method for generating a plurality of barcodes comprising:
  (a) generating, by a processor, a set of possible sequences of length N;
  (b) selecting a first barcode sequence from the set of possible sequences;
  (c) adding the first barcode sequence to a barcode candidate pool;
  (d) adding an additional barcode sequence from the set of barcode sequences to the candidate pool, wherein upon sequencing nucleic acid molecules comprising barcode sequences from the candidate pool, a first barcode of the barcode candidate pool will not be incorrectly identified as a different barcode in the barcode candidate pool when a sequence read of the first barcode differs from a corresponding barcode sequence from the candidate pool by one nucleotide;
  (e) repeating step j until the barcode candidate pool comprises a target number of barcodes M; and
  (f) synthesizing an oligonucleotide library comprising barcodes in the barcode candidate pool.

41. The method of embodiment 40, wherein M is at least five, at least 10, at least 20, at least 40, at least 50, at least 75, or at least 100.

42. The method of any one of embodiments 40-41, wherein (d) is computed in accordance with an error model associated with the sequencer.

43. The method of embodiment 42, wherein the error model associated with the sequencer is determined by sequencing a plurality of training barcode sequences of length N using the sequencer to generate a plurality of sequenced reads; and
  for each position in the training barcode sequences of length N,
  counting the number of times each nucleic acid base (A, T, G, C) is observed at a particular position in the plurality of sequence reads; and
  generating an error model associated with the sequencer by calculating the probability that a nucleotide observed at a position in a sequence read is accurate.

44. The method of embodiment 43, wherein the error model calculates the probability that a pair of nucleotides observed at a pair of positions in a sequence read are accurate.

45. The method of embodiment 43, wherein the error model comprises an objective function $$\Theta = \sum_{i=0}^{M-1} \sum_{j=i+1}^{M-1} \rho(\sigma_i | \sigma_j),$$

wherein $$\rho(\sigma_i | \sigma_j) = \sum_{k=0}^{N-1} \ln[P(\sigma_{ik} | \sigma_{ik}, k)],$$

and wherein $\rho(\sigma_i|\sigma_j)$ is the natural log of the probability of observing sequence $\sigma_i$ when the actual barcode sequence supplied to the sequencer is $\sigma_j$, M is the number of barcodes, $\sigma_{ik}$ refers to the nucleotide at the kth position in the ith barcode sequence, and $P(\sigma_{ik}|\sigma_{jk}, k)$ is the error model associated with the sequencer.

46. A group of oligonucleotides made by the method of any one of embodiments 19-45.

47. A library of nucleic acids comprising nucleic acids from a sample fused to oligonucleotides made by the method of any one of embodiments 19-45 by a common phosphodiester bond.

48. The library of nucleic acids of embodiment 47, wherein the oligonucleotides comprise sequences that differ from the nucleic acids from the sample at the same somatic position.

49. A plurality of samples comprising the oligonucleotides of embodiment 46.

50. A method of sequencing a plurality of nucleic acid samples comprising:
attaching oligonucleotides made by the method of any one of embodiments 40-45 to nucleic acids in the plurality of nucleic acid samples, wherein the oligonucleotides added to a sample comprise a same sequence and oligonucleotides added to different samples comprise different sequences;
sequencing the plurality of nucleic acid samples to produce a plurality of sequence reads; and
assigning the sequence reads to a sample corresponding to the attached barcode, wherein a sequence read comprising a single error is still correctly assigned to the sample corresponding to the attached barcode.

51. The method of embodiment 50, wherein the error is a mutation in a template molecule.

52. The method of embodiment 50, wherein the error is a mutation introduced during an amplification step prior to sequencing the molecule.

53. The method of embodiment 50, wherein the error is a read error made by a sequencer.

54. The method of any one of embodiments 50-53, wherein attaching oligonucleotides comprises ligating the oligonucleotides to the nucleic acids in the plurality of nucleic acid samples.

55. The method of any one of embodiments 50-53, wherein attaching oligonucleotides comprises PCR amplifying the nucleic acids in the plurality of nucleic acid samples using primers comprising the oligonucleotides.

56. The method of any one of embodiments 50-55, wherein attaching oligonucleotides comprises attaching oligonucleotides comprising two copies of the barcodes.

57. The method of embodiment 56, wherein assigning the sequence reads to a samples corresponding to the attached barcode further comprises comparing a first copy of the barcode to a second copy of the barcode.

58. A method for generating a plurality of barcode sequences of length N, comprising:
generating, by a processor, a set of possible sequences of length N;
for a starting barcode sequence in the set of possible sequences:
adding the starting barcode to a candidate pool of barcode sequences;
identifying a candidate sequence in the set of possible sequences that minimizes an objective function $\Theta$ representing the probability of observing any sequence in the candidate pool when the actual sequence is the candidate sequence;
adding the candidate sequence to the candidate pool; and
comparing the computed $\Theta$ to the $\Theta$ computed for the candidate pool; and
outputting the candidate pool having a computed $\Theta$ at or below a threshold level, e.g., the candidate pool having the lowest computed $\Theta$.

59. The method of embodiment 58, wherein the set comprises at least 4N-15, 4N-14, 4N-13, 4N-12, 4N-11, 4N-10, 4N-9, 4N-8, 4N-7, 4N-6, 4N-5, 4N-3, 4N-2, 4N-1, or 4N sequences.

60. The method of embodiment 58, wherein the barcode sequences are customized to a sequencer, and
wherein the objective function is computed in accordance with an error model associated with the sequencer.

61. The method of embodiment 60, wherein the error model is computed by:
sequencing a plurality of training barcode sequences of length N using the sequencer to generate a plurality of sequenced reads; and
for each position in the training barcode sequences of length N and for each actual nucleotide in the training barcode sequences, counting the number of occurrences of each nucleotide in the sequenced reads.

62. The method of embodiment 61, wherein the objective function is:

$$\Theta = \sum_{i=0}^{M-1} \sum_{j=i+1}^{M-1} \rho(\sigma_i | \sigma_j),$$

wherein $$\rho(\sigma_i | \sigma_j) = \sum_{k=0}^{N-1} \ln[P(\sigma_{ik} | \sigma_{ik}, k)],$$

and
wherein $\rho(\sigma_i|\sigma_j)$ is the natural log of the probability of observing sequence $\sigma_i$ when the actual barcode sequence supplied to the sequencer is $\sigma_j$, M is the number of barcodes, $\sigma_{ik}$ refers to the nucleotide at the kth position in the ith barcode sequence, and $P(\sigma_{ik}|\sigma_{jk}, k)$ is the error model associated with the sequencer.

63. A method of generating an instrument-specific DNA sequencing error model comprising:
providing a training set of barcode oligonucleotides, wherein barcode oligonucleotides of the training set comprise a barcode N nucleotides in length, wherein N is at least 5, at least 6, is at least 7, at least 8, at least 9, at least 10, at least 11, at least 11, at least 12, at least 13, at least 14, or at least 15, and wherein, throughout the training set, each nucleotide (A, T, G, C) appears at least once in each position in at least one barcode;
sequencing, together or separately, the members of the training set on a DNA sequencing instrument to generate an output comprising sequence reads; and generating an instrument-specific sequencing error model from the sequencing instrument output, wherein the model comprises, for each position in the barcode, a likelihood that a particular nucleotide (A, T, G, or C) will be correctly/incorrectly identified as a different, nucleotide.

64. The method of embodiment 63, wherein N is selected from the group consisting of 5, 6, 7, 8, 9, 10, 11, 12, 13, 14, or 15.

65. The method of embodiment 63, wherein the set comprises at least 4N-15, 4N-14, 4N-13, 4N-12, 4N-11, 4N-10, 4N-9, 4N-8, 4N-7, 4N-6, 4N-5, 4N-3, 4N-2, 4N-1, or 4N sequences.

66. The method of embodiment 63, wherein sequencing comprises generating a plurality of sequence reads for each member of the training set.

67. The method of embodiment 63, wherein, throughout the set, each nucleotide pair (AA, AT, AG, AC, TA, TT, TG, TC, GA, GT, GG, GC, CA, CT, CG, CC,) appears at least once in each pair of positions of the barcode in at least one barcode.

68. The method of embodiment 63, wherein the training set comprises no more than 4, 8, 16, 32, 64 or 128 different members.

69. The method of embodiment 63, wherein the training barcode sequences are sequenced together and sequence reads are sorted into groups by identifying the closest matching training barcode sequence in the training set.

70. The method of embodiment 63, wherein the sequencing instrument uses massively parallel signature sequencing (MPSS), DNA cluster sequencing (e.g., Illumina), polony sequencing (e.g., Church), pyrosequencing (e.g., Roche), sequencing by ligation (e.g., SOLiD sequencing, Thermo) semiconductor sequencing (e.g., DNA nanoball sequencing (e.g., Complete Genomics), single molecule sequencing (e.g., Helicos), single molecule real time (SMRT) sequencing, or nanopore DNA sequencing (e.g., PacBio).

71. A method of preparing oligonucleotides for use with a DNA sequencing instrument, wherein the oligonucleotides comprise M different nucleotide barcode sequences of at least N nucleotides in length, wherein M is at least five, at least 10, at least 20, at least 40, at least 50, at least 75, or at least 100, the method comprising:
    generating a set of possible nucleotide sequences of length N, wherein N is at least 5, at least 6, is at least 7, at least 8, at least 9, at least 10, at least 11, at least 11, at least 12, at least 13, at least 14, or at least 15;
    generating a plurality of groups of M nucleotide barcode sequences selected from the set;
    determining for each group, by using a sequencing error model for the DNA sequencing instrument, a probability of sequencing error for the nucleotide barcode sequences;
    selecting a group from the plurality of groups having a probability of sequencing error in the lowest 50%, lowest 25%, lowest 10%, lowest 5%, lowest 1%, or absolute lowest of the groups; and
    synthesizing oligonucleotides comprising the nucleotide barcode sequences of the selected group.

72. The method of embodiment 71, wherein the set comprises at least $4^{N-15}$, $4^{N-14}$, $4^{N-13}$, $4^{N-12}$, $4^{N-11}$, $4^{N-10}$, $4^{N-9}$, $4^{N-8}$, $4^{N-7}$, $4^{N-6}$, $4^{N-5}$, $4^{N-3}$, $4^{N-2}$, $4^{N-1}$, or $4^N$ sequences.

73. The method of embodiment 71, wherein the oligonucleotides further comprise an amplification primer sequence.

74. The method of embodiment 71, further comprising attaching the synthesized oligonucleotides to polynucleotide molecules in a plurality of different samples, wherein polynucleotides in a sample comprise a same oligonucleotide barcode and polynucleotides in different samples comprise different oligonucleotide barcodes.

75. A plurality of oligonucleotides synthesized using the barcode sequences of the selected group of embodiments 10-74.

76. A method comprising:
    a) generating an initial set of possible nucleotide sequences of length N ($4^N$ sequences);
    b) in a first iteration, performing a selection process comprising:
    i) partitioning the initial set into a first subset comprising one or more sequences selected from the initial set and a second subset comprising remainder sequences of the initial set;
    ii) generating pairs of candidate pools and remainder pools, wherein:
        1) each candidate pool comprises polynucleotide(s) having the sequence(s) in the first subset and a polynucleotide having the sequence of a different member of the second subset,
        2) each remainder pool comprises polynucleotides having sequences of the second subset less the different member added to the candidate pool;
    iii) synthesizing oligonucleotides comprising the sequences in the candidate pools;
    Iv) sequencing the oligonucleotides comprising the sequences in the candidate pools;
    v) determining, for each sequenced candidate pool, a sequencing error rate; and
    vi) selecting a sequenced candidate pool having an acceptably low error rate or the lowest error rate.

77. The method of embodiment 76, further comprising
    c) in X subsequent iterations, wherein X<=N-1, performing a selection process comprising:
    i) providing the selected sequenced candidate pool and its paired remainder pool from the previous iteration as a first subset and a second subset, respectively;
    ii) generating pairs of candidate pools and remainder pools, wherein:
        1) each candidate pool comprises the sequences in the first subset and a different member of the second subset,
        2) each remainder pool comprises sequences of the second subset less the different member added to the candidate pool;
    iii) synthesizing oligonucleotides comprising the sequences in the candidate pools;
    iv) sequencing the oligonucleotides comprising the sequences in the candidate pools;
    v) determining, for each sequenced candidate pool, a sequencing error rate; and
    vi) selecting a sequenced candidate pool having an acceptably low error rate or the lowest error rate.

78. The method of embodiment 76, wherein the set comprises at least 4N-15, 4N-14, 4N-13, 4N-12, 4N-11, 4N-10, 4N-9, 4N-8, 4N-7, 4N-6, 4N-5, 4N-3, 4N-2, 4N-1, or 4N sequences.

79. A method of generating a candidate barcode pool comprising:
    a) synthesizing a set of polynucleotides comprising barcodes comprising N nucleic acids;
    b) selecting a first subset of polynucleotides from the set of polynucleotides;
    c) generating a plurality of first candidate pools, wherein the first candidate pools comprise the first subset of polynucleotides and at least one additional polynucleotide from the set of polynucleotides that was not selected for the first subset of polynucleotides;
d) sequencing the plurality of first candidate pools;
e) determining a sequencing error rate for the first candidate pools; and
f) selecting a first candidate pool having an error rate less than a threshold error rate.

80. The method of embodiment 79, wherein the set comprises at least 4N-15, 4N-14, 4N-13, 4N-12, 4N-11, 4N-10, 4N-9, 4N-8, 4N-7, 4N-6, 4N-5, 4N-3, 4N-2, 4N-1, or 4N sequences.

81. The method of embodiment 79, further comprising:
g) generating a plurality of second candidate pools, wherein the second candidate pools comprise the first candidate pool selected in step f) and at least one additional polynucleotide from the set of polynucleotides that was not selected for the first candidate pool selected in step f);
h) sequencing the plurality of first candidate pools;
i) determining a sequencing error rate for the second candidate pools; and
j) selecting a second candidate pool having an error rate less than a threshold error rate.

82. A kit comprising a plurality of M containers, each container comprising an ensemble of oligonucleotide molecules comprising nucleotide barcode sequences of length N, wherein:
the predominant nucleotide barcode sequences in each ensemble is different from the other ensembles; and
the nucleotide barcode sequences in the kit have a probability of sequencing error, when sequenced by a selected DNA sequencing instrument, that is below a designated error threshold.

83. The kit of embodiment 82, wherein the probability of sequencing error is determined by the error model of embodiment 63.

84. The kit of embodiment 82, wherein the designated threshold is less than a probability sequencing error for the selected DNA sequencing instrument of a set of M control nucleotide sequences of length N having collective edit distance of at least one, at least two, at least three, at least four or at least five.

85. A method for determining sample-to-sample cross-contamination comprising:
introducing a different sample comprising polynucleotides into each of a plurality of containers, wherein one or more of the samples each comprise a polynucleotide having a nucleotide sequence unique to that sample;
sequencing the polynucleotides in each of the containers to produce sequence reads;
determining from the sequence reads, the presence and/or amount of each of the unique nucleotide sequences in containers into which the polynucleotide having the unique nucleotide sequence was not originally introduced.

86. The method of embodiment 85, wherein the containers are comprised as individual tubes, tubes in a strip, or wells in a multi-well plate.

87. The method of embodiment 85, further comprising, before sequencing, processing the samples, in parallel, to perform at least one of biochemical reaction on polynucleotides in the containers.

88. The method of embodiment 87, wherein at least one of biochemical reaction comprises DNA primer extension or DNA application.

89. The method of embodiment 85, wherein the unique nucleotide sequence is a non-natural sequence that is not natural to organisms for polynucleotides in the other containers originated.

90. The method of embodiment 85, wherein a plurality of the samples each comprise a polynucleotide having a nucleotide sequence unique to that sample.

91. A method comprising:
attaching a different barcode from a set of barcodes to polynucleotides in each different sample of a plurality of different samples to create tagged polynucleotides, wherein the barcode set comprises barcodes synthesized according to any one of the methods of embodiments 19-33, 34-39, or 58-62;
sequencing the tagged polynucleotides to produce sequence reads; and
assigning the sequence reads to one of the different samples based on the attached barcode.

92. The method of embodiment 91, comprising mixing polynucleotides from the different samples before sequencing.

93. A method comprising:
sequencing a set of polynucleotides tagged with sample-specific nucleotide barcode sequences according to any one of the methods of embodiments 19-33, 34-39, or 58-62, to produce a set of sequence reads of polynucleotides;
assigning, by executing a computer program, the sequence reads into different groups representing different samples using a plurality of different stringencies to assign barcode to a sample;
generating a receiver operating curve indicating a read at a different stringencies; and
selecting a stringency that provides a selected level of sensitivity and specificity.

94. A method of reducing cross-contamination in a collection comprising a collection of oligonucleotide samples, the method comprising:
a) providing a set of different nucleotide sequences;
b) performing a plurality of oligonucleotide synthesis reactions, each reaction in the plurality producing a synthesis product in which oligonucleotides having a selected nucleotide sequence from the set of nucleotide sequences comprise a predominant oligonucleotide species, wherein:
(1) different synthesis reactions are performed in parallel, wherein reactants and products in each different synthesis reaction travel along different flow paths, or
(2) different synthesis reactions are performed in series, wherein reactants and products in a synthesis reaction follow a flow path and wherein, for each synthesis reaction in the series, conduits in the flow path are replaced or cleaned with a nucleic acid destroying agent; and
c) assembling a collection comprising a plurality of samples, each sample containing a different synthesis product.

95. The method of embodiment 94, wherein each sample is comprised in a different container.

96. The method of embodiment 94, wherein the containers are contained together in a package as a kit.

97. The method of embodiment 94, wherein nucleotide coupling efficiency in each synthesis reaction is greater than 99.5%, 99.6% 99.7% 99.8% 99.9% or 99.97%.

98. The method of embodiment, 97 wherein each synthesis reaction comprises nucleotide double coupling reactions.

99. A method of creating a collection of double stranded polynucleotides comprising:
   a) for each of a plurality of different nucleotide sequences, preparing a sample comprising double-stranded polynucleotides in which one of the nucleotide sequences is a predominant sequence, wherein the double-stranded polynucleotides in each sample are synthesized from a set of partially overlapping oligonucleotides that tile across the nucleotide sequence and that hybridize at overlapping regions;
   b) assembling the samples into a collection.

100. The method of embodiment 99, wherein the collection comprises a package containing a plurality of containers, each container containing one of the samples.

101. The method of embodiment 99, wherein the collection comprises at least 12 samples, at least 24 samples, at least 48 samples or at least 96 samples.

102. The method of embodiment 99, wherein the nucleotide sequences are not natural nucleotide sequences.

103. The method of embodiment 99, wherein the nucleotide sequences are between 4 nucleotides and 1500 nucleotides in length, between 100 nucleotides and 800 nucleotides in length, or between 250 nucleotides and 500 in length.

104. The method of embodiment 99, wherein the oligonucleotides, when hybridize to one another, span the nucleotide sequence with gaps between oligonucleotides on the same street, and wherein synthesizing comprises filling in gaps between oligonucleotides (e.g., by klenow or PCR).

105. The method of embodiment 99, comprising ligating the overlapping oligonucleotides to produce the double stranded polynucleotide.

106. A method of determining cross-contamination of barcode oligonucleotides between different oligonucleotide samples, comprising:
   a) providing a plurality of control samples, each control sample comprising one or more predominant control polynucleotide species and having a polynucleotide contamination rate between samples of less than one part per 10,000, one part per 100,000, or one part per 1 million (e.g., prepared by the method of embodiment 99);
   b) providing a collection of oligonucleotide barcode samples, each sample comprising one or more predominant barcode oligonucleotides and contaminating barcode oligonucleotides, wherein the one or more predominant barcodes define a barcode tag;
   c) pairing each barcode sample with a different control sample, and attaching the barcode oligonucleotides to control polynucleotides in each pairing to produce sets of barcoded control polynucleotides;
   d) pooling the sets of barcoded control polynucleotides;
   e) sequencing the barcoded control polynucleotides in the pool to produce sequence information;
   f) using the sequence information, quantifying combinations of each barcode tag with each control polynucleotide in a barcoded control polynucleotide, wherein quantities of barcodes mismatched with control polynucleotides indicates cross-contamination.

107. The method of embodiment 106, wherein the number of sets is at least 12, at least 24, at least 48 or at 96.

108. The method of embodiment 106, further comprising determining, for each of one or more barcode samples, a probability that, in a plurality of barcoding reactions in which the oligonucleotide barcode samples are each paired with a different test sample, a control polynucleotide barcoded with the predominant barcode tag in the barcode sample represents a contaminant.

109. A sample comprising a collection of polynucleotides, each polynucleotide comprising a nucleotide barcode sequence, wherein the collection comprises a predominant nucleotide barcode sequence and contaminant nucleotide barcode sequences, wherein the contaminants are present in an amount less than one part per 10,000, less than one part per 100,000, less than one part per 1 million or less than one part per 10 million.

110. A kit comprising a plurality of containers, each container comprising a collection of polynucleotides, each polynucleotide comprising a nucleotide barcode sequence, wherein the collection comprises a predominant nucleotide barcode sequence and contaminant nucleotide barcode sequences, wherein the contaminants are present in an amount less than one part per 10,000, less than one part per 100,000, less than one part per 1 million or less than one part per 10 million and wherein a plurality of the containers comprise a different predominant nucleotide barcode sequence.

111. A non-transitory computer-readable storage media encoded with a computer program including instructions executable by a processor to generate a plurality of barcode sequences comprising:
   a module for generating a set of possible sequences of length N;
   a module for selecting a first barcode sequence from the set of possible sequences;
      a module for adding the first barcode sequence to a barcode candidate pool;
      a module for identifying a second barcode sequence in the set of possible sequences, wherein, upon sequencing a nucleic acid molecule comprising the second sequence, the second sequence has a reduced likelihood of being incorrectly identified as a different barcode in the barcode candidate pool compared to a threshold value;
      a module for adding the second sequence to the barcode candidate pool; and
      a module for outputting a report comprising barcodes in the barcode candidate pool.

112. A non-transitory computer-readable storage media encoded with a computer program including instructions executable by a processor to generate a plurality of barcode sequences comprising:
   a module for generating a set of possible sequences of length N;
   a module for selecting a first barcode sequence from the set of possible sequences;
   a module for adding the first barcode sequence to a barcode candidate pool;
   a module for adding an additional barcode sequence from the set of barcode sequences to the candidate pool, wherein the candidate pool comprising the additional barcode sequence has been identified as having a reduced likelihood that, upon sequencing nucleic acid molecules comprising barcode sequences from the candidate pool, a first member of the barcode candidate pool will be incorrectly identified as a different barcode in the barcode candidate pool compared to the addition of other barcode sequences remaining in the set of possible sequences; and
   a module for outputting a report comprising barcodes in the barcode candidate pool.

113. A non-transitory computer-readable storage media encoded with a computer program including instructions executable by a processor to generate a plurality of barcode sequences comprising:

(a) a module configured to generate a set of possible sequences of length N;

(b) a module configured to select a first barcode sequence from the set of possible sequences;

(c) a module configured to add the first barcode sequence to a barcode candidate pool;

(d) a module configured to add an additional barcodes sequences from the set of barcode sequences to the candidate pool until the barcode pool comprises a target number of barcodes M, wherein upon sequencing nucleic acid molecules comprising barcode sequences from the candidate pool, a first barcode of the barcode candidate pool will not be incorrectly identified as a different barcode in the barcode candidate pool when a sequence read of the first barcode differs from a corresponding barcode sequence from the candidate pool by one nucleotide;

(e) a module configured to output a report comprising the sequences for barcodes in the barcode candidate pool.

EXAMPLES

The following examples are provided for illustrative purposes only, and do not limit the scope of the embodiments of the present invention.

Example 1. Preparation and Storing of Samples

Storing and Pre-Treatment of Samples. All samples except urine should be stored at −80° C. until processing. Urine samples should be stored at 4° C. until processing.

Steps for pre-treatment of all clinical samples, except urine. 1. Thaw samples on ice inside a biosafety cabinet (BSC). 2. Add 3 volumes of TRIzol LS or 2 volumes of a DNA/RNA preservative. 3. Vortex sample for 10 seconds. 4. Incubate at room temperature for 3 minutes. 5. Vortex sample for 10 seconds. 6. Store at −80° C. until further processing.

Steps for pre-treatment of urine samples. 1. Bring samples on ice inside a biosafety cabinet. 2. Centrifuge the samples until bacteria are pelleted (>3000 g for >10 min). 3. Remove the supernatant. 4. Resuspend the pellet in 250 uL water. 5. Add 3 volumes of TRIzol LS or 2 volumes of a DNA/RNA preservative. 6. Vortex sample for 10 seconds. 7. Incubate at room temperature for 3 minutes. 8. Vortex sample for 10 seconds. 9. Store at −80° C. until further processing.

Steps for Cell Lysis of Sample. 1. If pre-treated sample is frozen, thaw on ice inside a BSC. 2. Shake and vortex the sample until homogeneous. 3. Transfer 1 mL of the mix to molecular biology grade bead beating tubes containing high density beads (e.g., 0.5 mm Zirconium tubes). 4. Bead beat on MP Biomedicals, LLC Fast Prep instrument. 5. Centrifuge for 60 seconds at 15,000×g, then transfer 750 µl of supernatant to 2 mL tube.

Example 2. Purification of RNA or RNA and DNA

Steps for Nucleic Acid (RNA and/or DNA) Extraction using Zymo Research Purification Kit and Protocol. 1. Add 750 µl ethanol to the 750 µl sample and mix by vortexing or pipetting. 2. Load mixture into a Zymo Research Spin IIC Column and centrifuge at 15,000×g for 1 minute. 3. Transfer the column into a new Collection Tube and discard the Collection Tube containing the flow-through. 4. Add 400 µl RNA Pre-Wash (Zymo Research) to the column and centrifuge at 15,000×g for 1 minute. 5. Transfer the column into a new Collection Tube and discard the Collection Tube containing the flow-through. 6. Add 400 µl RNA Pre-Wash to the column and centrifuge at 15,000×g for 1 minute. 7. Transfer the column into a new Collection Tube and discard the Collection Tube containing the flow-through 8. Add 700 µl RNA Wash Buffer to the column and centrifuge at 15,000×g for 1 minute. 9. Transfer the column into a new Collection Tube and discard the Collection Tube containing the flow-through. 10. Centrifuge at 15,000×g for an additional 2 minutes. 11. Transfer the spin column to an RNase free tube. 12. Wait 1 minute with the cap open. 13. Add 20 µl of DNase/RNase Free Water directly to the center of the column. 14. Wait 1 minute. 15. Spin at maximum speed for 1 minute. 16. Transfer filtrate to LoBind 1.5 mL tube. 17. Qubit RNA HS 1 µl of RNA. 18. Run on RNA BioAnalyzer RNA Pico Chip (Agilent). 19. Store RNA at −70° C.

Example 3. Removal of Non-Informative RNA (RNR)

Steps for Washing of Magnetic Beads. 1 Resuspend streptavidin magnetic beads by rocking and swirling. 2. Pipette beads into 1.5 mL RNase-free tubes. 3. Place the tubes on the magnetic rack for 2 minutes. 4. Draw off and discard the supernatant. 5. Remove the tubes from the magnetic rack. 6. Add 600 µl Solution A (Solution A: 0.1M NaOH, 0.05M NaCl) to each tube and pipette mix. 7. Place tubes on magnetic rack for 2 minutes. 8. Remove supernatant. 9. Resuspend beads in 200 µL of RB1 buffer (RB1 buffer: 1-10 mM Tris, pH=7.5-8.5, 0.1-1 mM EDTA, 50-150 mM NaCl, and 0.05-0.2% Tween) and pipette mix. 10. Place beads on magnetic rack for 2 minutes. 11. Remove supernatant. 12. Remove tube from magnet and resuspend in 10 µL of RB1 buffer. 13. Keep the beads at room temperature until use.

RNA/probe hybridization. Combine biotinylated RNR sample-specific oligonucleotide probes with 10-500 ng of the purified RNA sample and place in a thermal cycler. Incubate at 65-85° C. for 10 minutes, then incubate at 20-30° C. for 5 minutes.

Steps for Magnetic Bead Reaction and removal of hybridized RNA. 1. With thermomixers at 20-30° C., tubes with washed magnetic beads are placed on the thermomixer. 2. Without removing the PCT tube strip (with hybridized RNA and probe) from the thermocycler, the entire RNA/probe reaction volume is transferred to the magnetic beads on the thermomixer and mixed with pipetting. 3. The magnetic beads and RNA/probe mixture is incubated at 20-30° C. for 10 minutes with shaking at 200-1000 rpm. 4. Leaving tubes on the thermomixer, increase temperature to 30-40° C. with shaking at 200-1000 rpm. 5. As soon as temperature reaches 40° C., remove tubes. 6. Place tubes on magnet for at least 2 minutes and transfer the supernatant to PCR tube strips.

Example 4. Library Preparation of RNR Processed RNA or RNR Processed RNA and DNA Fragment RNA and double stranded (ds) copy DNA (ds cDNA) Synthesis. 1. Assemble 0.2 ml PCR reaction tubes on ice. 2. Add RNR processed RNA and RTO/dNTPs/TS buffer mix. RTO is the reverse transcriptase oligonucleotide. dNTPs is a deoxynucleotide mix of dATPs, dCTPs, dGTPs, and dTTPs. TS buffer is Tris saline buffer. 3. Incubate this mix at 65-85° C. for 1-5 minutes (depending on the RNA integrity) and then immediately place on ice. 4. Add master mix and mix well. Master mix comprises TSO (template-switching oligo), RNase inhibitor, and MMLV RT. 5. Incubate all tubes (e.g., in a thermocycler) at 40-50° C. for 10-90 minutes, then 70° C. for 10 minutes, followed by a 4° C. hold. This results in cDNA synthesis product of the RNA sample.

Steps for Pre-PCR Clean-up of the cDNA. 1. Bring SPRI (solid phase reversible immobilization) paramagnetic beads to room temperature (RT). 2. Prepare fresh 80% ethanol (EtOH) (800 µl per sample). 3. Adjust reaction volume of cDNA sample to 50 µl using TLE buffer (10 mM Tris, 0.1 mM EDTA, pH 8). 4. Add 50 µl of well-vortexed SPRI beads. 5. Pipette mix 10 times and incubate at RT for 15 minutes. 6. Put tubes on magnet until supernatant (SN) is clear (approximately 5 minutes). 7. Discard supernatant. 8. Add 200 µL of 80% EtOH, let stand for 30 seconds, discard supernatant. 9. Repeat EtOH wash. 10. Air dry beads with lid open on magnetic rack until they start to crack. 11. Remove tubes from magnet and add 102 µl of TLE buffer and pipette mix. 12. Incubate at RT for 2 minutes. 13. Put tubes back on magnet and wait until SN is clear. 14. Transfer 100 µl of SN to a new 1.5 mL tube. 15. Add 60 µl of SPRI beads and pipette mix 10 times. 16. Incubate tubes at room temperature for 15 minutes. 17. Put tubes onto magnetic rack and wait for solution to become clear. 18. Transfer supernatant to a new tube. 19. Add 20 µl of SPRI beads to the sample and pipette mix. 20. Incubate at RT for 10 minutes. 21. Place tubes onto magnetic rack and wait for solution to become clear. 22. Discard supernatant. 23. Add 200 µl of 80% EtOH, let stand for 30 seconds, discard supernatant. 24. Repeat EtOH wash. 25. Air dry beads with lid open on magnetic rack until they start to crack. 26. Remove tubes from magnet and add 12 µl TLE buffer and pipette mix. 27. Incubate tubes at RT for 2 minutes. 28. Put tubes onto magnetic rack and wait for solution to become clear. 29. Transfer 10 µl of the SN to a PCR tube.

Synthesis of Barcode Oligonucleotides. Barcode oligonucleotides sets for dual indexing of the library fragments for use in the NextSeq 500 Illumina sequencer are used. During synthesis of these barcode oligonucleotides, a double coupling method is used. This means that at each position of the growing DNA oligo, the new nucleotide is added (and reacted) twice, increasing the yield of each coupling reaction. This introduces many fewer phasing (synthesis) errors in the barcodes.

After synthesis, each barcode oligonucleotide is purified. Between purifications, all the lines and columns used for purification are bleached twice with sodium hypochlorite. This treatment chemically destroys DNA structure and prevents barcode-to-barcode contamination, which is essential for high fidelity of demultiplexing.

PCR Amplification of cDNA and Barcode Oligonucleotides 1. Assemble the reactions on ice and add each of the following to the 10 µl of cleaned cDNA synthesis product. 2. Add 2 ul of an index set of barcode oligonucleotides. 3. Add 38 µl of PCR Master Mix and mix well. PCR Master Mix per reaction: 25 µl DNA polymerase 2× Master Mix and 13 nuclease free water. 4. Run reactions in PCR cycling: reaction of 98° C./30 sec, 15×Cycles(98° C./10 sec, 55° C./30 sec, 72° C./30 sec), 72° C./2 min, 4° C. hold.

Post PCR Clean-Up. 1. Bring SPRI-based beads (e.g., Agencourt® AMPure® Xtra Performance (XP) beads) to RT. 2 Prepare fresh 80% EtOH (400 µL per sample). 3 Transfer PCR reactions to 1.5 mL tubes. 4. Add 50 µl (1× volume) of well-vortexed SPRI beads. 5. Pipette mix 10 times and incubate at RT for 15 minutes. 6. Put tubes on magnet until supernatant is clear (approximately 5 minutes). 7. Discard supernatant (SN). 8. Add 200 µl 80% EtOH, and let stand for 30 seconds; discard SN. 9. Wash one more time with EtOH and remove last drops of EtOH. 10. Air-dry the beads until pellet just starts to crack. 11. Remove tubes from the magnet. 12. Add 20 µl of TLE buffer and pipette mix 10 times; then incubate for 2 minutes. 13. Put tubes back on the magnet until supernatant is clear (approximately 5 minutes). 14. Transfer SN to new tubes.

Library Validation. Library concentration may be determined using Qubit™ nucleic acid quantifier (ThermoFisher Scientific). Average size of the DNA library may be determined using Bioanalyzer with High Sensitivity chip. The final library concentration may be determined using quantitative PCR (qPCR).

Example 5. Sequencing of Library DNA

Sequencing may be performed on any Illumina platform. The process may also be customized for a different sequencing technology by changing the adapter sequences.

NextSeq Cstm R1 prmr (Custom Read 1 primer) and NextSeq Cstm i5 prmr (Custom i5 primer) are spiked into the MiSeq cartridge from a 100 µM stock concentration.

Example 6 Removal of Non-informative RNAs (RNR)

This method physically removes unwanted (non-informative) RNA sequences from a mixture of RNAs. This is achieved by in-solution hybridization of biotinylated DNA probes to unwanted RNAs followed by removal of such complexes from the solution using streptavidin-coated surfaces, such as beads.

Step 1:

Combine RNAs with DNA probes. DNA probes are preferably single-stranded, 75-85 nts long. They can be biotinylated at one or multiple sites. In one embodiment, they are biotinylated at both 3' and 5' ends, to maximize the percentage of biotinylated probes and minimize conversion of the probes into library fragments in downstream processes. Absolute probe and RNA concentrations can be adjusted. A stoichiometric excess (preferably 2 or more-fold) of the probes is preferred.

The probe-RNA mixture is combined in a buffer that enables rapid and effective hybridization, while allowing downstream steps without additional RNA purification. The buffer preferably is between pH 7.5-8, has 50-150 mM NaCl, 0.1-1 mM EDTA, and 0.05-0.2% Tween-20 or another non-ionic detergent.

Step 2:

The probe-RNA mixture is heated to 65-85 C for 1-3 min, then cooled to 15-25 C over 1-5 min.

Step 3:

Streptavidin beads pre-equilibrated to 15-25 C are added to the probe-RNA mixture. The amount of beads should be sufficient to capture the probes. The bead suspension is shaken at about 400-1000 rpm for 2-10 min at 15-25 C, then the temperature is raised to 40-50 C.

Step 4:

The bead suspension is placed on a magnet. The unwanted (non-informative) RNAs separate with the beads, while the remaining RNAs remain in the supernatant and are collected for further processing.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method for synthesizing a set of oligonucleotide barcodes, comprising:
   (a) providing a sequencer-specific error model for a high-throughput sequencing system, generated by:
      (1) using the system to sequence a plurality of training barcode sequences of length N, wherein N is at least 5, to generate a plurality of sequence reads; and
      (2) for positions in the training barcode sequences, counting the number of times a nucleic acid base is observed at a particular position in a plurality of the sequence reads; and
   (b) generating one or more sets of barcode sequences by:
      (i) selecting one or more first nucleotide sequences from an initial set of possible nucleotide sequences, wherein the initial set of possible nucleotide sequences comprises all possible nucleotide sequences of length N ($4^N$ sequences), and wherein N is at least 5, to form a candidate pool;
      (ii) for each iteration in a plurality of iterations:
         for each respective nucleotide sequence in the set of possible nucleotide sequences, determining a respective predicted error rate, θ, produced by the sequence-specific error model, for the candidate pool that further includes the respective nucleotide sequence, wherein θ is computed using the objective function:
wherein $$\rho(\sigma_i|\sigma_j) = \Sigma_{k=0}^{N-1} \ln[P(\sigma_{ik}|\sigma_{jk}, k)],$$

$\rho(\sigma_i|\sigma_j)$ is the natural log of the probability of observing sequence $\sigma_i$ when the actual barcode sequence supplied to the sequencer is $\sigma_j$, M is the number of barcodes, $\sigma_{ik}$ refers to the nucleotide at the kth position in the ith barcode sequence, and $P(\sigma_{ik}|\sigma_{jk}, k)$ is the error model associated with the sequencer, and adding, to the candidate pool, the respective nucleotide sequence from the set of possible nucleotide sequences that minimizes the predicted error rate, θ;

(iii) iterating step (ii) to create a final candidate pool having M different nucleotide sequences, wherein M is at least 10;

(c) synthesizing the final candidate pool to produce a pool of barcodes;

(d) attaching different synthesized oligonucleotide barcodes to polynucleotide molecules in a plurality of different samples to produce barcoded samples;

(e) pooling the barcoded samples; and (f) sequencing polynucleotide molecules in the barcoded samples with the sequencing system or a corresponding type thereof.

2. The method of claim 1, wherein N is at least 7.

3. The method of claim 2, wherein M is at least 50.

4. The method of claim 2, wherein M is at least 96.

5. The method of claim 1, wherein N is at least 10.

6. The method of claim 5, wherein M is at least 50.

7. The method of claim 5, wherein M is at least 96.

8. The method of claim 7, further comprising, in each iteration, adding to the candidate pool a respective nucleotide sequence from the set of possible nucleotide sequences when the predicted error rate of the candidate pool with the added sequence is no more than 1/1,000,000.

9. The method of claim 1, wherein N is at least 15.

10. The method of claim 1, wherein the sequencer uses a sequencing method selected from massively parallel signature sequencing (MPSS), DNA cluster sequencing, polony sequencing, pyrosequencing, sequencing by ligation, DNA nanoball sequencing, single molecule sequencing, single molecule real time (SMRT) sequencing, or nanopore DNA sequencing.

11. The method of claim 1, wherein the barcodes further comprise an amplification primer sequence.

12. The method of claim 1, wherein M is at least 50.

13. The method of claim 1, wherein M is at least 100.

14. The method of claim 1, wherein counting comprises, for each position in the training barcode sequences and for each nucleotide in the training barcode sequences, counting the number of occurrences of each nucleotide in the sequenced reads.

15. The method of claim 1, wherein iteratively adding a new sequence comprises adding a sequence such that the sequences of the barcodes in the candidate pool have a minimum edit distance of three.

16. The method of claim 1, wherein iteratively adding a new sequence comprises adding a sequence such that the sequences of the barcodes in the candidate pool have a minimum edit distance of four.

17. The method of claim 1, wherein M is at least 50.

18. The method of claim 1, wherein M is at least 96.

19. The method of claim 1, further comprising, in each iteration, adding to the candidate pool a respective nucleotide sequence from the set of possible nucleotide sequences when the predicted error rate of the candidate pool with the added sequence is no more than 1/1000.

20. The method of claim 1, further comprising, in each iteration, adding to the candidate pool a respective nucleotide sequence from the set of possible nucleotide sequences when the predicted error rate of the candidate pool with the added sequence is no more than 1/10,000.

21. The method of claim 1, further comprising, in each iteration, adding to the candidate pool a respective nucleotide sequence from the set of possible nucleotide sequences when the predicted error rate of the candidate pool with the added sequence is no more than 1/100,000.

22. The method of claim 1, further comprising, in each iteration, adding to the candidate pool a respective nucleotide sequence from the set of possible nucleotide sequences when the predicted error rate of the candidate pool with the added sequence is no more than 1/1,000,000.

23. The method of claim 1, further comprising, in each iteration, adding to the candidate pool a respective nucleotide sequence from the set of possible nucleotide sequences when the predicted error rate of the candidate pool with the added sequence is no more than 1/10,000,000.

24. The method of claim 1, further comprising, in each iteration, adding to the candidate pool a respective nucleotide sequence from the set of possible nucleotide sequences when the predicted error rate of the candidate pool with the added sequence is no more than 1/100,000,000.

25. The method of claim 1, comprising generating a plurality of sets of barcode sequences in step (b), and selecting for synthesis a final candidate pool having a predicted error rate that is in the lowest 10% of the predicted error rates of the plurality of final candidate pools.

26. The method of claim 1, comprising generating a plurality of sets of barcode sequences in step (b), and selecting for synthesis a final candidate pool having a predicted error rate that is in the lowest 1% of the predicted error rates of the plurality of final candidate pools.

27. The method of claim 1, comprising generating a plurality of sets of barcode sequences in step (b), and selecting for synthesis a final candidate pool having a predicted error rate that is the lowest of the predicted error rates of the plurality of final candidate pools.

28. The method of claim 1, further comprising (g) assigning one or more sequence reads of the sequenced polynucleotide molecules to one of the samples in the plurality of different samples based on one or more corresponding barcodes of the one or more sequence reads.

29. The method of claim 1, wherein the system uses DNA cluster sequencing.

30. A method for synthesizing a set of oligonucleotide barcodes, comprising:
(a) providing a sequencer-specific error model for a high-throughput sequencing system, generated by:
(1) using the system to sequence a plurality of training barcode sequences of length N, wherein N is at least 5, to generate a plurality of sequence reads; and
(2) for positions in the training barcode sequences, counting the number of times a nucleic acid base is observed at a particular position in a plurality of the sequence reads; and (b) generating one or more sets of barcode sequences by:
  (i) selecting one or more first nucleotide sequences from an initial set of possible nucleotide sequences of length N ($4^N$ sequences), wherein N is at least 5, to form a candidate pool;
  (ii) iteratively adding a new sequence from the set of possible nucleotide sequences to the candidate pool such that, in each iteration, a candidate pool with the added sequence produces a predicted error rate, θ, in the sequencer-specific error model, that is below a threshold value, wherein θ is computed using the objective function:

$$\Theta = \sum_{i=0}^{M-1} \sum_{j=i+1}^{M-1} \rho(\sigma_i | \sigma_j),$$

wherein $$\rho(\sigma_i | \sigma_j) = \sum_{k=0}^{N-1} \ln[P(\sigma_{ik} | \sigma_{jk}, k)],$$

and wherein $$\rho(\sigma_i|\sigma_j) = \sum_{k=0}^{N-1} \ln[P(\sigma_{ik}|\sigma_{jk}, k)],$$

and wherein
  $\rho(\sigma_i|\sigma_j)$ is the natural log of the probability of observing sequence $\sigma_i$ when the actual barcode sequence supplied to the sequencer is $\sigma_j$,
  M is the number of barcodes,
  $\sigma_{ik}$ refers to the nucleotide at the kth position in the ith barcode sequence, and
  $P(\alpha_{ik}|\alpha_{jk}, k)$ is the error model associated with the sequencer;
  (iii) iterating step (ii) to create a final candidate pool having M different nucleotide sequences, wherein M is at least 10;
(c) synthesizing the final candidate pool to produce a pool of barcodes;
(d) attaching different synthesized oligonucleotide barcodes to polynucleotide molecules in a plurality of different samples to produce barcoded samples;
(e) pooling the barcoded samples; and
(f) sequencing polynucleotide molecules in the barcoded samples with the sequencing system or a corresponding type thereof.

* * * * *

SEQUENCE LISTING

<160> NUMBER OF SEQ ID NOS: 3

<210> SEQ ID NO 1
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
acgatgcgat gccgcgtata gacgatcgat gctagtcgat gtgctagcgt agtcgacggc        60
gatagcgctt taaatcgcgc tagccgcgat agttagccgc gcgatacgac tatcgtagct       120
agcgag                                                                 126

<210> SEQ ID NO 2
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
acgcgatatg aagagctcga accggatcgg ctaatatcgg atcggatcgg cgctatatta        60
tccattcggc ttcttcgcgc gcttctgata tgctcgcgct agctacggct aggatcggct       120
atagct                                                                 126

<210> SEQ ID NO 3
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
cgaggcgcgc gatatagcta aagatatgcg cgatatgcgc tagctttaaa tatccgaaga        60
accgttatgc tagatagcta gctacgatat gcgctatagc gctatcctta ggctcggata       120
ggctct                                                                 126